(12) United States Patent
Tran

(10) Patent No.: US 11,357,426 B2
(45) Date of Patent: Jun. 14, 2022

(54) GLUCOSE MANAGEMENT

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 379 days.

(21) Appl. No.: 16/743,539

(22) Filed: Jan. 15, 2020

(65) Prior Publication Data

US 2021/0212606 A1    Jul. 15, 2021

(51) Int. Cl.
*A61B 5/145* (2006.01)
*A61B 5/0255* (2006.01)
*A61B 5/00* (2006.01)

(52) U.S. Cl.
CPC ........ *A61B 5/14532* (2013.01); *A61B 5/0006* (2013.01); *A61B 5/0017* (2013.01); *A61B 5/0024* (2013.01); *A61B 5/0075* (2013.01); *A61B 5/0255* (2013.01); *A61B 5/6801* (2013.01); *A61B 2562/0238* (2013.01)

(58) Field of Classification Search
CPC ......... A61B 5/145; A61B 5/00; A61B 5/0255; A61B 5/0024; A61B 5/0017; A61B 5/0075; A61B 5/6801; A61B 5/0006; A61B 5/14532; A61B 2562/0238
See application file for complete search history.

(56) References Cited

U.S. PATENT DOCUMENTS

| | | | |
|---|---|---|---|
| 4,014,321 A | 3/1977 | March | |
| 6,043,492 A | 3/2000 | Lee | |
| 8,747,336 B2 | 6/2014 | Tran | |
| 9,445,759 B1 | 9/2016 | Lamego | |
| 9,699,859 B1 | 7/2017 | Li | |
| 9,820,658 B2 | 11/2017 | Tran | |
| 10,350,454 B1 | 7/2019 | Li | |
| 2010/0168537 A1 | 7/2010 | Ueda | |
| 2010/0280838 A1 | 11/2010 | Bosworth | |
| 2013/0178335 A1 | 7/2013 | Lin | |
| 2016/0058133 A1 | 3/2016 | Fournier | |
| 2017/0344726 A1 | 11/2017 | Duffy | |
| 2018/0035930 A1 | 2/2018 | Sokolov | |
| 2018/0074069 A1 | 4/2018 | Sokolov | |
| 2019/0180855 A1 | 6/2019 | Sysko | |
| 2020/0203012 A1* | 6/2020 | Kamath | A61B 5/1455 |
| 2021/0275061 A1* | 9/2021 | McKinney | A61B 5/14532 |

FOREIGN PATENT DOCUMENTS

CN    110575181 A  * 12/2019

OTHER PUBLICATIONS

Atkinson, F. S., Foster-Powell, K., & Brand-Miller, J. C. (2008). International tables of glycemic index and glycemic load values: 2008. Diabetes care, 31(12), 2281-2283. doi:10.2337/dc08-1239.

(Continued)

*Primary Examiner* — Eric J Messersmith
(74) *Attorney, Agent, or Firm* — PatentPC www.patentpc.com; Bao Tran

(57) ABSTRACT

Systems and methods are disclosed for monitoring a user by calibrating one or more noninvasive sensors to track a user glucose level at one or more user physical activity conditions; generating a calibration based on the one or more user conditions; and in real time detecting a current user condition and applying the calibration to accurately estimate the user glucose or insulin level.

22 Claims, 18 Drawing Sheets

(56) References Cited

OTHER PUBLICATIONS

Dungan K, Verma N. Monitoring Technologies—Continuous Glucose Monitoring, Mobile Technology, Biomarkers of Glycemic Control. [Updated Jan. 10, 2018]. In: Feingold KR, Anawalt B, Boyce A, et al., editors. Endotext [Internet], South Dartmouth (MA): MDText.com, Inc.; 2000-. Available from: https://www.ncbi.nlm.nih.gov/books/NBK279046/.

Jennie Brand-Miller et al., "Moreover, Glycemic index, postprandial glycemia, and the shape of the curve in healthy subjects: analysis of a database of more than 1000 foods ", Am J Clin Nutr 2009;89:97-105.

\* cited by examiner

Using an invasive glucose system to generate medical grade data to calibrate a mobile device with noninvasive sensor(s) tracking the user's glucose level Generating/finetuning a calibration curve based on a variety of user conditions (sleep, exercise, rest, sit, walk) using best fit approach, statistical approach, or learning machine approach In real time detecting the user condition with the non-invasive sensor(s) and applying the calibration curve to accurately estimate the glucose level

FIG. 1A

Using an invasive glucose system to generate medical grade data to calibrate a mobile device with noninvasive sensor(s) tracking the user's glucose level (for example the noninvasive sensors include at least a near-infrared light and a bioimpedance sensor)

Training a system to estimate glucose based on a variety of user conditions (sleep, exercise, rest, sit, walk) using best fit approach, statistical approach, or learning machine approach In real time detecting the user condition with the non-invasive sensor(s) and applying the trained system to accurately and non-invasively estimate the glucose level

FIG. 1B

Using an invasive glucose system to generate medical grade data to calibrate a mobile device with one or more noninvasive sensor(s) tracking the user's glycemic index (GI) level (for example the noninvasive sensors include at least a near-infrared light and a bioimpedance sensor)

Training a system to estimate glucose based on a variety of user conditions (sleep, exercise, rest, sit, walk) using best fit approach, statistical approach, or learning machine approach In real time applying the trained system to accurately and non-invasively estimate the GI for food consumption and optionally estimating calorie consumption

FIG. 1C

Using a non-invasive system with one or more noninvasive sensor(s) tracking the user's glycemic index (GI) level (for example the noninvasive sensors include at least a near-infrared light and a bioimpedance sensor)

Training a system to estimate GI that may take into consideration a variety of user conditions (sleep, exercise, rest, sit, walk) using best fit approach, statistical approach, or learning machine approach In real time applying the trained system to accurately and non-invasively estimate the GI for food consumption and optionally estimating calorie consumption

FIG. 1D

Training a calorie estimator from a food database including images, food ingredient, calorie data using best fit approach, statistical approach, or learning machine approach Taking images of a food about to be consumed and matching the images to an entry in the food database with corresponding calorie data using image processing and the calorie estimator and determining quantity/type of food from the images In real time applying the calorie estimator for estimating calorie consumption

FIG. 1E

Training a calorie estimator from a food database including images, food ingredient, calorie data using best fit approach, statistical approach, or learning machine approach Taking images of a food about to be consumed and matching the images to an entry in the food database with corresponding calorie data using image processing and the calorie estimator and determining quantity/type of food from the images In real time applying the calorie estimator for estimating calorie consumption and GI based on the food ingredient

FIG. 1F

Train a calorie estimator from a food database including images, food ingredient, calorie data using best fit approach, statistical approach, or learning machine approach Taking images of a food about to be consumed and determining quantity/type of food from the images using image processing and the calorie estimator Using one or more noninvasive sensors (such as a near-infrared light, a bioimpedance sensor, a cornea based sensor, or suitable noninvasive sensor combinations) to determine the user's glycemic index (GI) level Applying the calorie estimator and the non-invasive sensor(s) to accurately and non-invasively estimate the GI for food consumption and/or estimating calorie consumption

FIG. 1G

Using an invasive glucose system to generate medical grade data to calibrate a mobile device with noninvasive sensor(s) tracking the user's glucose level Using a gold standard heart monitoring system to generate medical grade data to calibrate a mobile device with noninvasive sensor(s) tracking the user's heart data Generating/finetuning calibration curve(s) based on a variety of user conditions (sleep, exercise, rest, sit, walk) using best fit approach, statistical approach, or learning machine approach In real time detecting the user condition with the non-invasive sensor(s) and applying the calibration curve to accurately estimate the glucose level

FIG. 2A

Using an invasive glucose system to generate medical grade data to calibrate a mobile device with noninvasive sensor(s) tracking the user's glucose level (for example the noninvasive sensors include at least a near-infrared light and a bioimpedance sensor)

Using a gold standard heart monitoring system to generate medical grade data to calibrate a mobile device with noninvasive sensor(s) tracking the user's heart data (ECG or blood pressure)

Training a system to estimate glucose and/or BP based on a variety of user conditions (sleep, exercise, rest, sit, walk) using best fit approach, statistical approach, or learning machine approach In real time detecting the user condition with the non-invasive sensor(s) and applying the trained system to accurately and non-invasively estimate the glucose level

FIG. 2B

Using an invasive glucose system to generate medical grade data to calibrate a mobile device with one or more noninvasive sensor(s) tracking the user's glycemic index (GI) level (for example the noninvasive sensors include at least a near-infrared light and a bioimpedance sensor), and using a gold standard heart monitoring system to calibrate a mobile device with noninvasive sensor(s) tracking the user's heart data (ECG or blood pressure)

Training a system to estimate glucose and/or BP based on a variety of user conditions (sleep, exercise, rest, sit, walk) using best fit approach, statistical approach, or learning machine approach In real time applying the trained system to accurately and non-invasively estimate the GI for food consumption and optionally estimating calorie consumption

FIG. 2C

Using a non-invasive system with one or more noninvasive sensor(s) tracking the user's glycemic index (GI) level (for example the noninvasive sensors include at least a near-infrared light and a bioimpedance sensor), and using a gold standard heart monitoring system to calibrate a mobile device with noninvasive sensor(s) tracking the user's heart data (ECG or blood pressure)

Training a system to estimate GI, glucose, BP that may take into consideration a variety of user conditions (sleep, exercise, rest, sit, walk) using best fit approach, statistical approach, or learning machine approach In real time applying the trained system to accurately and non-invasively estimate the GI for food consumption and optionally estimating calorie consumption

FIG. 2D

Training a calorie estimator from a food database including images, food ingredient, calorie data using best fit approach, statistical approach, or learning machine approach Taking images of a food about to be consumed and matching the images to an entry in the food database with corresponding calorie data using image processing and the calorie estimator Determining quantity/type of food from the images In real time applying the calorie estimator for estimating calorie consumption Training a system to estimate GI, glucose, BP that may take into consideration a variety of user conditions (sleep, exercise, rest, sit, walk) using best fit approach, statistical approach, or learning machine approach

FIG. 2E

Training a calorie estimator from a food database including images, food ingredient, calorie data using best fit approach, statistical approach, or learning machine approach Taking images of a food about to be consumed and matching the images to an entry in the food database with corresponding calorie data using image processing and the calorie estimator Determining quantity/type of food from the images In real time applying the calorie estimator for estimating calorie consumption and GI based on the food ingredient Training a system to estimate GI, glucose, BP that may take into consideration a variety of user conditions (sleep, exercise, rest, sit, walk) using best fit approach, statistical approach, or learning machine approach

FIG. 2F

Train a calorie estimator from a food database including images, food ingredient, calorie data using best fit approach, statistical approach, or learning machine approach Taking images of a food about to be consumed and determining quantity/type of food from the images using image processing and the calorie estimator Using one or more noninvasive sensors (such as a near-infrared light, a bioimpedance sensor, a cornea based sensor, or suitable noninvasive sensor combinations) to determine the user's glycemic index (GI) level Applying the calorie estimator and the non-invasive sensor(s) to accurately and non-invasively estimate the GI, glucose, and BP for food consumption and/or estimating calorie consumption

FIG. 2G

| |
|---|
| Place a calibration sheet with known dots at a known distance and perpendicular to a camera view |
| Take snap shot of the sheet, and correlate the position of the dots to the camera image |
| Place a different calibration sheet that contains known dots at another different known distance and perpendicular to camera view. |
| Take snap shot of the sheet and correlate the position of the dots to the camera image |
| Smooth the dots to the pixels to minimize digitization errors |
| For each pixel, draw a line from Dot1(x,y,z) to Dot2 (x, y, z) defining a cone center where the camera can view |

| |
|---|
| Set up mesh network appliances (1000) |
| Determine patient position using in-door positioning system (1002) |
| Determine patient movement using accelerometer output (1004) |
| Determine vital parameter including patient heart rate (1006) |
| Determine if patient needs assistance based on in-door position, fall detection and vital parameter (1008) |
| Confirm prior to calling third party (1010) |
| If confirmed or non-responsive, make connection with third party and send voice over mesh network to appliance worn by the patient (1012) |
| If needed, call emergency personnel to get medical care (1014) |

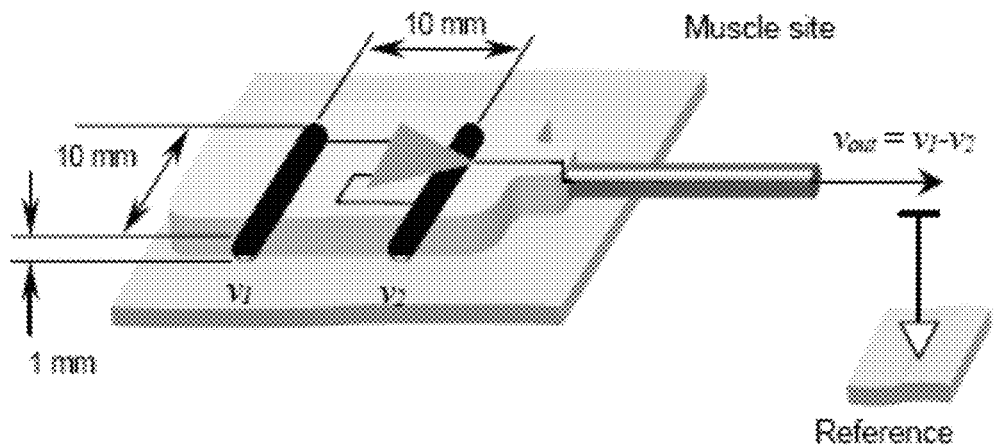
FIG. 15A
HISTORICAL MEASUREMENT
RECENT MEASUREMENT
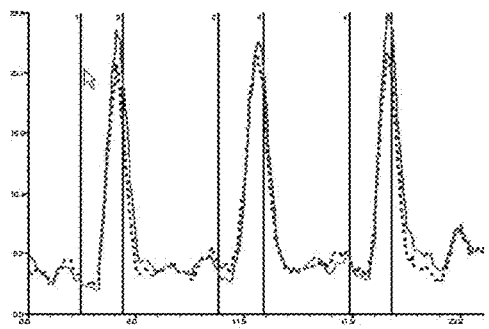
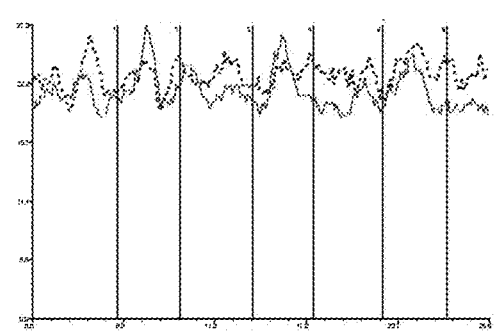
FIG. 15B
FIG. 15C
| Generate a blood pressure model of a patient (2002) |
| --- |
| Determine a blood flow velocity using a piezoelectric transducer (2004) |
| Provide the blood flow velocity to the blood pressure model to continuously estimate blood pressure (2006) |
FIG. 16A

| |
|---|
| Attach monitoring device and calibration device to patient (2010) |
| Determine blood flow velocity from the monitoring device and actual blood pressure from the calibration device (2012) |
| Generate a blood pressure model based on the blood flow velocity and the actual blood pressure (2014) |
| Remove calibration device (2016) |
| Determine blood flow velocity (2018) |
| Provide blood flow velocity to the blood pressure model to estimate blood pressure (2020) |

FIG. 16B

| |
|---|
| Detect weakness in left half and right half of patient body - arms, legs, face (3000) |
| Detect walking pattern for loss of balance or coordination (3002) |
| Ask user to move hands/feet in a predetermined pattern (3004) |
| Read accelerometer output in accordance with predetermined pattern movement (3006) |
| Provide accelerometer output to a pattern classifier (3008) |
| Check whether patient is experiencing dizziness or sudden, severe headache with no known cause (3010) |
| Display a text image and ask the patient to read back the text image, one eye at a time (3012) |
| Use speech recognizer to detect confusion, trouble speaking or understanding (3014) |
| Ask patient if they feel numbness in the body- arms, legs, face (3016) |
| Ask patient to squeeze gauge/force sensor to determine force applied during squeeze (3018) |

FIG. 16C

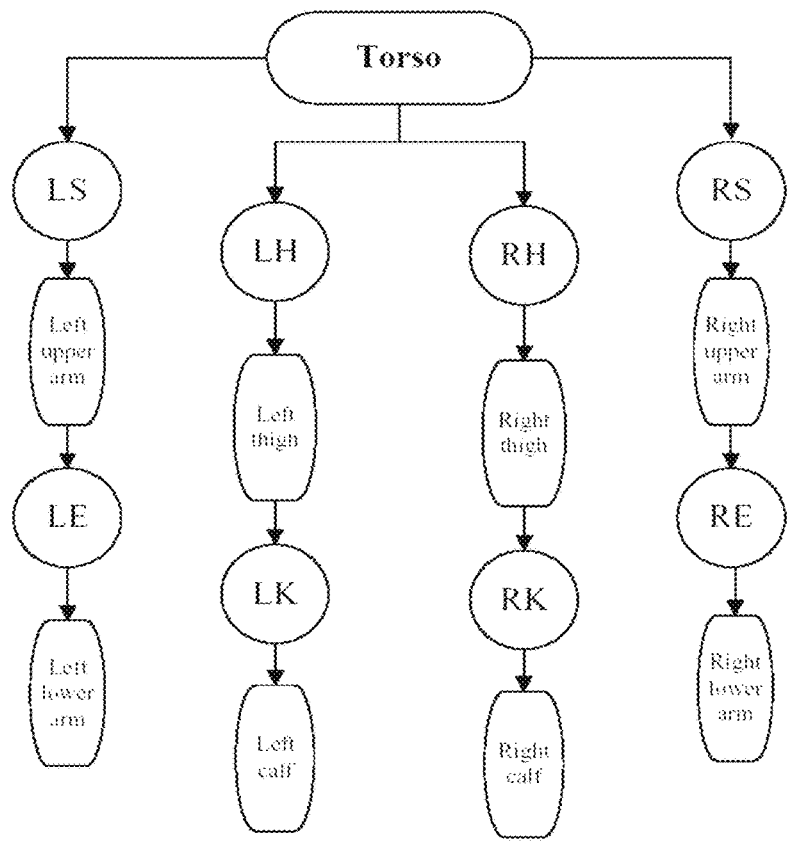

FIG. 16D

| Compare historical left shoulder (LS) strength against current LS strength (3200) |
|---|
| Compare historical right shoulder (RS) strength against current RS strength (3202) |
| Compare historical left hip (LH) strength against current LH strength (3204) |
| Compare historical right hip (RH) strength against current RH strength (3206) |
| If variance between historical and current strength exceeds threshold, generate warning (3208) |

FIG. 16E

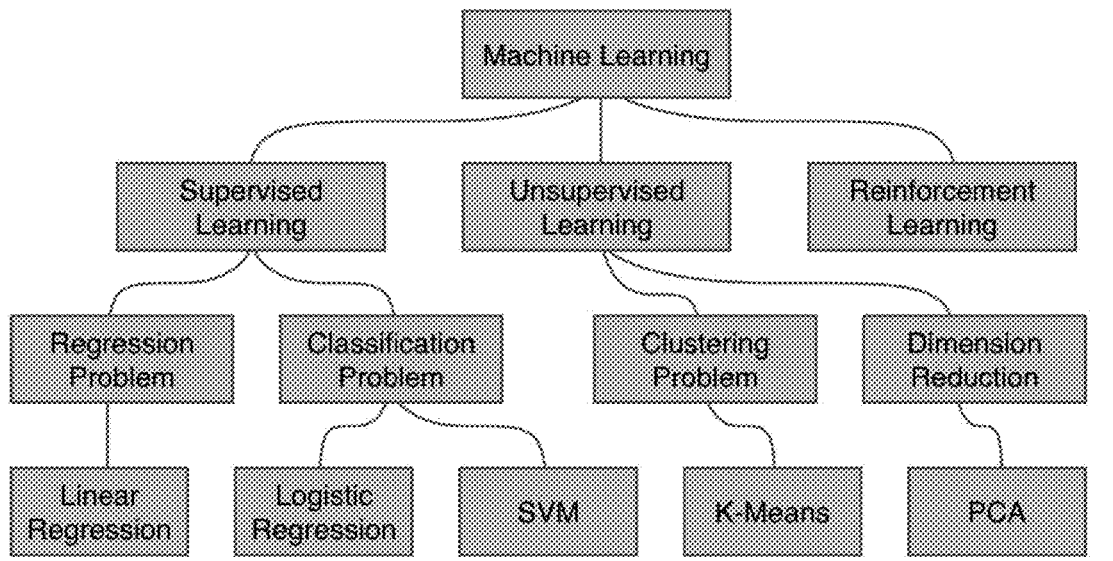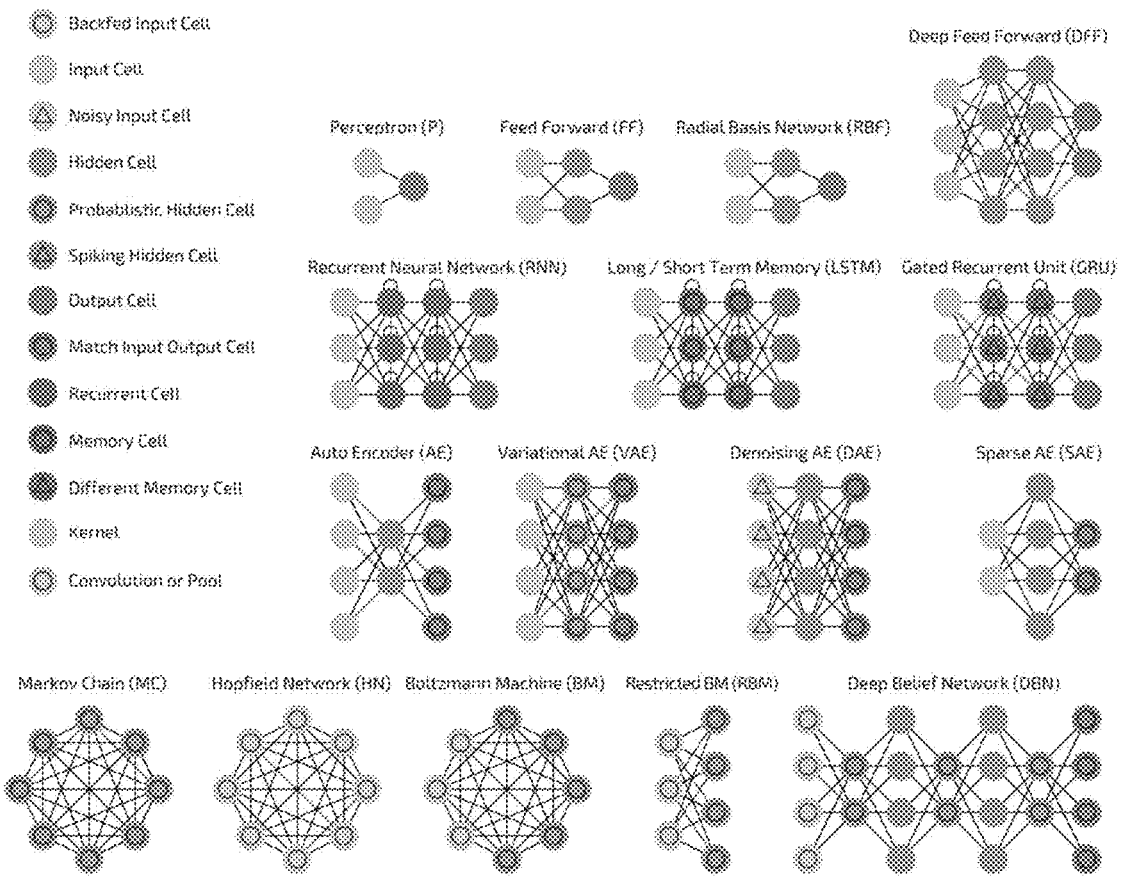
FIG. 18

GLUCOSE MANAGEMENT

This application claims priority to U.S. Application Ser. No. 62/930,305 filed Nov. 4, 2019, the contents of which are incorporated by reference.

BACKGROUND

High blood pressure is twice as likely to strike a person with diabetes than a person without diabetes. Left untreated, high blood pressure can lead to heart disease and stroke. In fact, a person with diabetes and high blood pressure is four times as likely to develop heart disease than someone who does not have either of the conditions. About two-thirds of adults with diabetes have blood pressure greater than 130/80 mm Hg or use prescription medications for hypertension.

SUMMARY

In a first aspect, systems and methods are disclosed for monitoring a user by using an invasive glucose monitor to generate medical grade data; calibrating one or more non-invasive sensors to track a user glucose level at one or more user conditions; generating a calibration curve based on the one or more user conditions; and in real time detecting a current user condition and applying the calibration curve to accurately estimate the user glucose level.

Advantages of glucose monitoring, singly or with cardiovascular monitoring, may include one or more of the following. The system reduces unnecessary blood sampling with an invasive blood glucose sensor until the measurement accuracy of the estimated blood glucose level from the non-invasive sensor reaches its accuracy, and this reduces pain and inconvenience on the part of the user and lowers the risk of infection, among others. The system eliminates pain and decreases the risk of infection as it relates to multiple finger pricks per day with a lancet, which is currently the state-of-the-art technology. Even minimally invasive patch-based glucose monitoring devices that take measurements at the same site for up to two weeks have drawbacks compared to non-invasive methods because they can cause skin irritation from the adhesive or the tissue has an inflammatory response to the temporary implanted sensor. The system enables convenient CGM management, without the invasive aspects of existing CGM. The data available through CGM permits significantly more fine-tuned adjustments in insulin dosing and other therapies than spot testing from self-monitoring of blood glucose (SMBG) can provide. The system can be used for Closed loop control (CLC). Also known as an "artificial" or "bionic" pancreas, this technology will link CGM with automatically controlled insulin delivery, using non-living components made of silicon, plastic, and metal. The first steps toward CLC are now available. Connectivity between glucose monitoring technologies and mobile devices facilitates ongoing improvements in self-care and communication of data. The system also detects alternate markers of Glucose Control and the use of additional analytes besides glucose for diabetic control. Continuous blood glucose monitoring can improve HbA1c levels (average level of blood sugar over a longer period of time) in diabetics and reduce long-term effects such as diabetic foot ulcers, diabetic retinopathy, and kidney damage. The system provides real time (RT-CGM) which not only display the current glucose every few minutes, but may also alert the patient for impending (projected alert) or actual (threshold alert) hyperglycemia or hypoglycemia or rate of change in glucose. Current and recent glucose levels, trend information, and a visual alarm are all presented so that a patient can predict future low or high glucose excursions. Using this information will allow the patient to take actions to spend more time in the euglycemic range and less time in the hypoglycemic or hyperglycemic ranges. Personalized treatments thanks to online measurements of the actual amount of glucose in the blood, as well as another step towards an artificial pancreas are added benefits of this method. This also facilitates continuous patient monitoring in the intensive care unit because it eliminates the need for staff to check blood sugar levels intermittently several times a day. Continuous blood glucose monitoring allows many conclusions about the patient's metabolism. The temperature, water content or the analysis of body fluids on the skin surface—such as sweat—are also measurement parameters that play an important role in endurance sports. The system can predict the glycemic index of a mixed food assimilated by a healthy human and can be used for developing various devices and systems for automatic monitoring of carbohydrate content of human food. Moreover, the system can provide virtual medication to treat diabetes without chemicals and drugs when it applies a learning system to adjust user behavior (such as spatial and temporal timing of selected diet and exercise) to keep glucose in a predetermined range.

In another aspect, a system includes a cellular, WiFi, or and Bluetooth transceiver coupled to a processor; and at least two wearable sensors including accelerometer, heart rate sensor, bioimpedance sensor, EMG sensor, or glucose sensor.

In another aspect, a system includes a processor; and at least two wearable sensors including accelerometer, heart rate sensor, bioimpedance sensor. The bioimpedance sensor measures high and low frequency signals from the body, while the glucose sensor uses a plurality of LEDs, each individually activated so as to emit corresponding wavelengths in sequence. The accelerometer indicates the sensor orientation and movement and is used by the signal processor in determining valid plethysmographs. A neural network is used to match glucose related composite parameters. Clinical data collection compares invasive blood draw measurements to noninvasive sensor measurements of the same person. Neural networks or statistical analyzers predict composite parameters CPs derived noninvasively from sensor data. The clinical data collection derives an invasive blood panel that generates a myriad of blood constituents such as blood urea nitrogen (BUN), high-density lipoprotein (HDL), low-density lipoprotein (LDL), total hemoglobin (THB), creatine (CRE) to name just a few. In various embodiments, the parameters are trained with invasively-measured glucose over a general population of interest; the highest correlation with invasively-measured glucose over a specific population matching a patient of interest; or the lowest error in the measurement of glucose, for example. The neural network derives glucose estimates based on the average glucose across a population of individuals according to the measured parameters. The population-based glucose estimate can also be refined by receiving an individually-calibrated glucose from a blood glucose sensor and noninvasive sensor estimate.

In another aspect, a mobile system, comprising: a transceiver to communicate data via a personal area network (PAN); an accelerometer and a gyroscope; a processor coupled to the transceiver, the accelerometer and the gyroscope, the processor executing one or more applications to record user speech and to record data regarding movement detected by the accelerometer and the gyroscope; two or more sensors in communication with the processor to detect user vital sign data; and a health application executed by the processor to generate a health analysis using the vital sign data and the data regarding movement detected by the accelerometer and the gyroscope, wherein the transceiver communicates the analysis to another computer via the PAN.

In yet another aspect, a system includes a processor; a cellular, WiFi, or Bluetooth transceiver coupled to the processor; at least two wearable sensors including accelerometer, heart rate sensor, bioimpedance sensor, EMG sensor, or glucose sensor. The heart sensor may be an ECG circuit or an SPO2 circuit (such as multiple LEDs at different wavelengths and optical receivers)

In another aspect, a system includes an accelerometer to detect movement or fitness; a sensor coupled to a wrist, hand or finger to detect blood-oxygen levels or heart rate or pulse rate and mounted on a wristwatch wearable device and a voice communication device having a wireless transceiver adapted to receive blood-oxygen level or heart rate or pulse rate from the sensor over a wireless personal area network (PAN).

In yet another aspect, a system includes a cellular telephone having a vital sign sensor thereon to detect heart rate, pulse rate or blood-oxygen levels; and a wristwatch wearable device in wireless communication with the cellular telephone, including at least two wearable sensors including accelerometer, heart rate sensor, bioimpedance sensor, EMG sensor, or glucose sensor; a wireless transceiver adapted to communicate with the cellular telephone over a wireless personal area network (PAN); and a processor coupled to the sensor and the transceiver to send pulse rate to the cellular telephone.

In a further aspect, a health care monitoring system for a person includes one or more wireless nodes forming a wireless network to communicate data over the wireless network to detect a health problem. Implementations can include watches that capture fitness data (activity, heart rate, glucose, blood pressure, walking rate, dietary or calorie consumption, among others) and sending the data to a hospital database where medical and fitness data is used to treat the patient. Other implementations include collecting data from different devices with different communication protocols such as blood pressure measurement devices, scales, glucose meters, among others, and upload the data to a computer which converts the data into an intermediate format that is compatible with different protocols for interoperability purposes.

In another aspect, a heart monitoring system for a person includes one or more wireless nodes forming a wireless network; at least two wearable sensors including accelerometer, heart rate sensor, bioimpedance sensor, EMG sensor, or glucose sensor, wherein the sensors communicate with a wireless transceiver adapted to communicate with the one or more wireless nodes; and a software module receiving data from the wireless nodes to detect changes in patient vital signs.

In another aspect, a monitoring system includes one or more wireless nodes forming a wireless network coupled to at least two wearable sensors including accelerometer, heart rate sensor, bioimpedance sensor, EMG sensor, or glucose sensor; and a software module receiving data from the wireless nodes to detect deteriorations in patient vital signs.

In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network.

In another aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

In yet another aspect, a monitoring system for a person includes one or more wireless nodes forming a wireless network; and a wearable device including: a processor; a transceiver coupled to the processor to communicate with the one or more wireless nodes; a wearable sensor on a patch or bandage secured to the person's skin and coupled to the processor; an accelerometer coupled to the processor; and a thumb sensor coupled to the processor.

In another aspect, a health monitoring system for a person includes a mobile telephone case including a cellular transceiver to provide wireless data and voice communication; a sensor including one or more electrodes mounted on the mobile telephone case to contact the person's skin and capture bio-electrical signals therefrom; an amplifier coupled to the electrodes; a processor coupled to the amplifier; and a screen coupled to the processor to display medical data such as images of the bio-electrical signals.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In a further aspect, a treatment method includes:
providing a non-invasive sensor to monitor a biomarker
calibrating the non-invasive sensor with a medical grade sensor;
detecting an oral intake and estimating a biomarker level from the oral intake;
performing a physical activity to keep the biomarker level at a range.

Implementation can include one or more of the following:
training a learning machine to estimate a glucose level from the food intake.
the oral intake comprises food intake, further comprising manually entering each food type or estimating a content of each food type from an image of the food type.
applying a learning machine to estimate the food type or calories from the food type.
the biomarker comprises glucose and the medical grade sensor comprises a blood-bases glucose monitor.
applying a food digestion curve to estimate the biomarker level. Can also include performing the physical activity before a peak of the food digestion curve.
training a learning machine to estimate a glucose level from the food intake.
the physical activity can be exercise, running, walking, jogging, swimming, light sport.
detecting a biomarker response to an individual oral intake.
detecting a biomarker response to variations of an individual oral intake by adding one or more ingredients to the oral intake.
the oral intake comprises a cannabinoid (CB) intake, further comprising manually entering each CB type or estimating a content of each CB type from an image of the CB.
applying a CB absorption curve to estimate the biomarker level.
applying a learning machine to estimate CB absorption.
the biomarker comprises and the medical grade sensor comprises a blood-based glucose monitor.
the oral intake comprises food intake, further comprising manually entering each food type or estimating a content of each food type from an image of the food type.
applying a food digestion curve to estimate the biomarker level.
applying a learning machine to estimate the food type or calories from the food type.
the biomarker comprises glucose and the medical grade sensor comprises a blood-bases glucose monitor.

In one aspect, systems and methods include one or more entities including a sensor configured to provide data in at least a first information standard from a first manufacturer and a second information standard from a second manufacturer; and an electronic health record database configured to: capture information from the one or more entities, normalize the captured information from first and second manufacturers in a common format, and add metadata for the captured information.

In another aspect, an interoperable health-care system includes a network; one or more medical data collection appliances coupled to the network, each appliance transmitting data conforming to an interoperable format; and a computer coupled to the network to store data for each individual in accordance with the interoperable format.

The user can take his/her weight, blood pressure, and cholesterol measurement daily, and the data is sent from a health base station to a monitoring service at his doctor's office. Periodically, the user gets an automated health summary generated by a service at his doctor's office as well as information to help him maintain a healthy lifestyle. The health information can be stored in an external HIPAA compliant health storage database so that the user and his doctor can access his health information over the web. The system extends health care system into the home and can record personal health data on a systematic periodic basis. Appointments can be automatically scheduled with providers. Long-term data for medical baseline can be collected. The system can also provide predictive alerts for high-risk conditions. The system can perform initial triage utilizing biosensors, images, e-mail/chat/video.

Advantages of the system may include one or more of the following. The system empowers people with the information they need to better manage their health and the health of their loved ones. The interoperability enables disparate industries to work together to combine their products and services through connectivity standards and provide millions of people with the tools they need to better manage their health and the health of their families. The system can perform chronic disease management, monitoring the health and healthcare needs of aging people and proactive health and fitness. The interoperable system can address the data storage requirements for health and wellness management, chronic disease management or patient recovery, medication management, and fitness and workout tracking. For example, using a blood pressure sensor, a weight scale or a cholesterol monitor, the user regularly collects health data that is then reviewed by the patient's caregiver for remote monitoring and health management of the patient. The system can provide remote monitoring of multiple patients, seamless device replacement and support for clinical trials. The Medical Device Profile will be compliant with the US Health Insurance Portability and Accountability Act (HIPAA) and other international data privacy requirements.

By enabling a network of readily connected health and medical devices, people with diabetes or other chronic diseases will be able to share vital sign information such as blood pressure and glucose level with their doctors. Adult children will be able to remotely watch over their aging parents and proactively help them manage safely in their own homes. Diet and fitness conscious individuals will also be able to seamlessly share their weight and exercise data with fitness consultants through the Internet.

The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format. The appliances can communicate data conforming to the interoperable format over one of: cellular protocol, ZigBee protocol, Bluetooth protocol, WiFi protocol, WiMAX protocol, USB protocol, ultrawideband protocol.

In another aspect, a monitoring system for a person includes one or more wireless nodes and a stroke sensor and glucose sensor coupled to the person and the wireless nodes to determine a medical problem, for example a stroke attack in conjunction with low or high glucose levels. The stroke monitoring system is interoperable with emergency vehicle and/or hospital systems and provides information to quickly treat stroke once the patient reaches the treatment center.

In one aspect, a monitoring system for a person includes one or more wireless nodes and an electromyography (EMG) sensor coupled to the person and the wireless nodes to determine a medical issue such as a stroke attack or out of control glucose level.

In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network.

In a further aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth.

In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected.

In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected.

Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected.

In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected.

In yet another aspect, a monitoring system includes one or more cameras to determine a three dimensional (3D) model of a person; means to detect a dangerous condition based on the 3D model; and means to generate a warning when the dangerous condition is detected.

In another aspect, a method to detect a dangerous condition for an infant includes placing a pad with one or more sensors in the infant's diaper; collecting infant vital parameters; processing the vital parameter to detect SIDS onset; and generating a warning.

Advantages of the system may include one or more of the following. The system detects the warning signs of stroke and/or uncontrolled glucose level and prompts the user to reach a health care provider within 2 hours of symptom onset. The system enables patent to properly manage acute stroke/glucose problem, and the resulting early treatment might reduce the degree of morbidity that is associated strokes and glucose problems.

Other advantages of the invention may include one or more of the following. The system for non-invasively and continually monitors a subject's arterial blood pressure, with reduced susceptibility to noise and subject movement, and relative insensitivity to placement of the apparatus on the subject. The system does not need frequent recalibration of the system while in use on the subject.

In particular, it allows patients to conduct a low-cost, comprehensive, real-time monitoring of their vital parameters including blood pressure and glucose level, singly or in combination. Using the web services software interface, the invention then avails this information to hospitals, home-health care organizations, insurance companies, pharmaceutical agencies conducting clinical trials and other organizations. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An onboard or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's cardiac condition. Certain cardiac conditions can be controlled, and in some cases predicted, before they actually occur. Moreover, data from the patient can be collected and analyzed while the patient participates in their normal, day-to-day activities.

In cases where the device has fall detection in addition to blood pressure measurement, other advantages of the invention may include one or more of the following. The system provides timely assistance and enables elderly and disabled individuals to live relatively independent lives. The system monitors physical activity patterns, detects the occurrence of falls, and recognizes body motion patterns leading to falls. Continuous monitoring of patients is done in an accurate, convenient, unobtrusive, private and socially acceptable manner since a computer monitors the images and human involvement is allowed only under pre-designated events. The patient's privacy is preserved since human access to videos of the patient is restricted: the system only allows human viewing under emergency or other highly controlled conditions designated in advance by the user. When the patient is healthy, people cannot view the patient's video without the patient's consent. Only when the patient's safety is threatened would the system provide patient information to authorized medical providers to assist the patient. When an emergency occurs, images of the patient and related medical data can be compiled and sent to paramedics or hospital for proper preparation for pick up and check into emergency room.

The system allows certain designated people such as a family member, a friend, or a neighbor to informally check on the well-being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely.

Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well being of the individual can be compiled for the remote healthcare provider. Feedback reports can be sent to monitored subjects, their designated informal caregiver and their remote healthcare provider. Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. For example, the system can perform patient behavior analysis such as eating/drinking/smoke habits and medication compliance, among others.

The patient's home equipment is simple to use and modular to allow for the accommodation of the monitoring device to the specific needs of each patient. Moreover, the system is simple to install. Regular monitoring of the basic wellness parameters provides significant benefits in helping to capture adverse events sooner, reduce hospital admissions, and improve the effectiveness of medications, hence, lowering patient care costs and improving the overall quality of care. Suitable users for such systems are disease management companies, health insurance companies, self-insured employers, medical device manufacturers and pharmaceutical firms.

The system reduces costs by automating data collection and compliance monitoring, and hence reduce the cost of nurses for hospital and nursing home applications. At-home vital signs monitoring enables reduced hospital admissions and lower emergency room visits of chronic patients. Operators in the call centers or emergency response units get high quality information to identify patients that need urgent care so that they can be treated quickly, safely, and cost effectively. The Web based tools allow easy access to patient information for authorized parties such as family members, neighbors, physicians, nurses, pharmacists, caregivers, and other affiliated parties to improve the Quality of Care for the patient.

In an on-line pharmacy aspect, a method for providing patient access to medication includes collecting patient medical information from a patient computer; securing the patient medical information and sending the secured patient medical information from the patient computer to a remote computer; remotely examining the patient and reviewing the patient medical information; generating a prescription for the patient and sending the prescription to a pharmacy; and performing a drug interaction analysis on the prescription.

Implementations of the on-line pharmacy aspect may include one or more of the following. The medical information can include temperature, EKG, blood pressure, weight, sugar level, image of the patient, or sound of the patient. Responses from the patient to a patient medical questionnaire can be captured. The doctor can listen to the patient's organ with a digital stethoscope, scanning a video of the patient, running a diagnostic test on the patient, verbally communicating with the patient. The digital stethoscope can be a microphone or piezoelectric transducer coupled to the Zigbee network to relay the sound. A plurality of medical rules can be applied to the medical information to arrive at a diagnosis. Genetic tests or pharmacogenetic tests can be run on the patient to check compatibility with the prescription. Approval for the prescription can come from one of: a doctor, a physician, a physician assistant, a nurse. The system can monitor drug compliance, and can automatically ordering a medication refill from the pharmacy.

For pharmacy applications, advantages of the pharmacy system may include one or more of the following. The system shares the patient's medical history and can be updated by a remote physician and the remote dispensing pharmacy. As the doctor and the pharmacy have the same access to the patient medical history database, patient data is updated in real time, and is as current and complete as possible. The patient, doctor, pharmacy, and third-party testing entities benefit from a uniform pricing structure that is based on the diagnosis and treatment. The patient only pays for standard medical treatments for his or her illness. The physician is paid a standard fee which covers the average work spent with a patient with the specific type of medical situation. The dispensing pharmacy is able to provide the highest level of service, since it is able to double check all medications dispensed to each patient along with the optimal way to detect anticipated negative drug interactions. The pricing structure is competitive as physicians do not need to be distributed physically, and those with specialty areas may remain centrally located and yet be able to interact electronically with patients. The system still provides physical access to specialists since the patients which are evaluated can be directed to visit a specialist physically, when remote review and contact is ineffectual. The on-line pharmacy tracks the specific needs and medical history of each patient and can provide an expert system to advise the patient on proper drug usage and potential drug interactions. The system automates the purchasing of drugs, pricing the prescription or submission of the claims to a third party for pricing, entering the complete prescription in their computer system, and auditing from third parties which provide payment. The on-line pharmacy provides detailed multimedia guidance or assistance to the patient regarding the filled prescription. The patient can freely search for answers regarding the use of the filled prescription, its possible side effects, possible interactions with other drugs, possible alternative treatments, etc. The patient can communicate using video or VOIP with a remote pharmacist regarding any number of questions, and be counseled by the local pharmacist on the use of the filled prescription. Thus, the system minimizes the danger from harmful side effects or drug interactions by providing patients with full access to information. The system allows a patient to enjoy the selection and price of a mail-order pharmacy without subjecting the patient to dangerous interactions or side effects which may occur in unsupervised prescription purchases. The on-line pharmacy offers the selection and benefits of a "central fill" pharmacy method without requiring the local pharmacy to purchase drugs to fill each prescription, price each prescription, or be subjected to audits from third parties who provide payment.

In yet another embodiment, a wireless housing provides one or more bioelectric contacts conveniently positioned to collect bioelectric patient data. The housing can be a patch, a wristwatch, a band, a wristband, a chest band, a leg band, a sock, a glove, a foot pad, a head-band, an ear-clip, an ear phone, a shower-cap, an armband, an ear-ring, eye-glasses, sun-glasses, a belt, a sock, a shirt, a garment, a jewelry, a bed spread, a pillow cover, a pillow, a mattress, a blanket or a sleeping garment such as a pajama. The bed spread, pillow cover, pillow, mattress, blanket or pajama can have bioelectrically conductive contacts in an array so that the patient can enjoy his/her sleep while vital parameters can be captured. In one embodiment, an array of parallel conductive lines can be formed on the housing side that faces the patient and the electrical signal can be picked up. The data captured by the contacts are transmitted over the mesh network such as ZigBee or Bluetooth to a base station.

BRIEF DESCRIPTION OF THE DRAWINGS

FIGS. 1A-1G illustrates exemplary processes and systems for monitoring glucose, while FIGS. 2A-2G illustrates exemplary processes and systems for monitoring glucose and a second disease state such as cardiovascular/heart related issues.

FIGS. 3A-3C show exemplary glucose charts from OGTT initial characterization of the user, a non-invasive sensor using bioimpedance sensors, and from a CGM (Dexcom 4), while

FIG. 5A illustrates a process for three dimensional (3D) detection of the user.

FIG. 5B illustrates an exemplary process for determining and getting assistance for a patient or user.

FIG. 6A shows an exemplary wrist-watch based assistance device while

FIG. 15A shows an exemplary EMG sensor while FIGS. 15B-C show exemplary EMG graphs of a patient.

FIGS. 16A-16B show exemplary blood pressure determination processes while FIGS. 16C-E shows exemplary stroke determination processes.

FIG. 18 shows exemplary learning machines to monitor a patient health condition.

DESCRIPTION

Figure 3A:
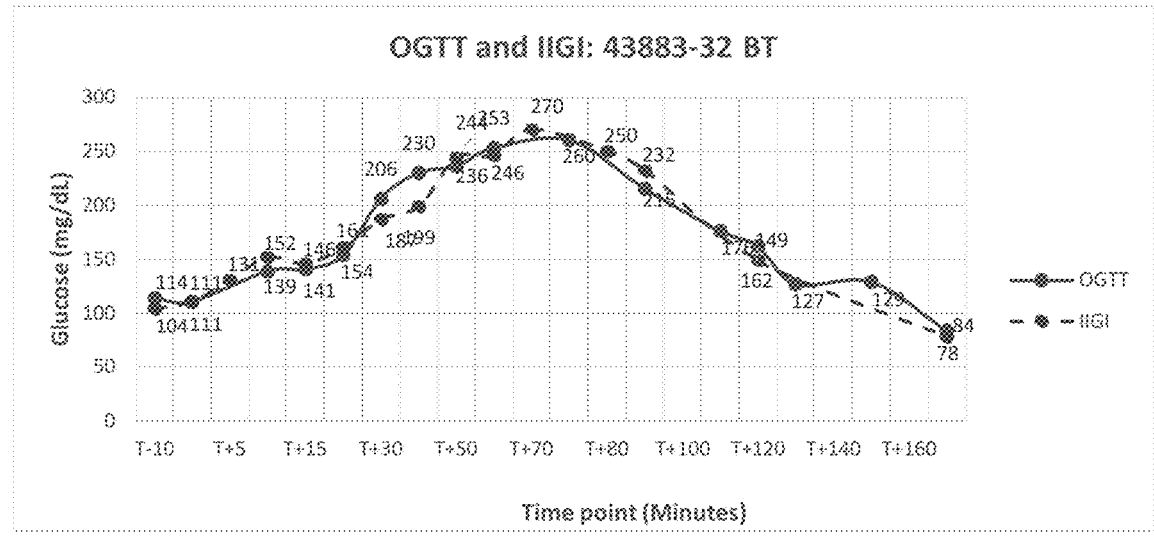

FIGS. 1A-1G show various exemplary processes to capture and process glucose data while FIGS. 2A-2G show various exemplary processes to capture and process glucose data together with cardiovascular data (from ECG/blood pressure sensors, for example). FIG. 1A shows an exemplary method to conveniently measure blood glucose level. The method includes using an invasive glucose system to generate medical grade data to calibrate a mobile device with noninvasive sensors tracking the user's glucose level. The most accurate reading of a blood sugar level is measured directly from blood, using a glucose meter. The data from the glucose meter is provided to calibrate the non-invasive system. The method then includes generating a calibration curve based on a variety of user conditions (sleep, exercise, rest, sit, walk); and in real time detecting the user condition and applying the calibration curve to accurately estimate the glucose level.

The system guides the user in timing of calibration. Calibration, where necessary, are avoided when trend arrows indicate rapid swings in glucose. While systems are becoming more reliable, patients should be instructed when to verify sensor readings before taking action such as meal boluses or treatment of hypoglycemia. Moreover, while FIGS. 1A-1G describe glucose monitoring detail, as there is a link between high blood pressure and glucose, all systems in FIGS. 1A-1G can include heart rate monitoring, ECG monitoring, and blood pressure monitoring (which is detailed after the description of FIGS. 1A-1B).

In FIG. 1B, the process includes: using an invasive glucose system to generate medical grade data to calibrate a mobile device with noninvasive sensor(s) tracking the user's glucose level (for example the noninvasive sensors include at least a near-infrared light and a bioimpedance sensor); training a system to estimate glucose based on a variety of user conditions (sleep, exercise, rest, sit, walk) using best fit approach, statistical approach, or learning machine approach; in real time detecting the user condition with the non-invasive sensor(s) and applying the trained system to accurately and non-invasively estimate the glucose level.

In FIG. 1C, the process includes: using an invasive glucose system to generate medical grade data to calibrate a mobile device with one or more noninvasive sensor(s) tracking the user's glycemic index (GI) level (for example the noninvasive sensors include at least a near-infrared light and a bioimpedance sensor); training a system to estimate glucose based on a variety of user conditions (sleep, exercise, rest, sit, walk) using best fit approach, statistical approach, or learning machine approach; in real time applying the trained system to accurately and non-invasively estimate the GI for food consumption and optionally estimating calorie consumption.

In FIG. 1D, the process includes: using a non-invasive system with one or more noninvasive sensor(s) tracking the user's glycemic index (GI) level (for example the noninvasive sensors include at least a near-infrared light and a bioimpedance sensor); training a system to estimate GI that may take into consideration a variety of user conditions (sleep, exercise, rest, sit, walk) using best fit approach, statistical approach, or learning machine approach; in real time applying the trained system to accurately and non-invasively estimate the GI for food consumption and optionally estimating calorie consumption.

In FIG. 1E, the process includes: train a calorie estimator from a food database including images, food ingredient, calorie data using best fit approach, statistical approach, or learning machine approach; taking images of a food about to be consumed and matching the images to an entry in the food database with corresponding calorie data using image processing and the calorie estimator; determining quantity/type of food from the images; in real time applying the calorie estimator for estimating calorie consumption.

In FIG. 1F, the process includes: train a calorie estimator from a food database including images, food ingredient, calorie data using best fit approach, statistical approach, or learning machine approach; taking images of a food about to be consumed and matching the images to an entry in the food database with corresponding calorie data using image processing and the calorie estimator; determining quantity/type of food from the images; in real time applying the calorie estimator for estimating calorie consumption and GI based on the food ingredient.

In FIG. 1G, the process includes: train a calorie estimator from a food database including images, food ingredient, calorie data using best fit approach, statistical approach, or learning machine approach; taking images of a food about to be consumed and determining quantity/type of food from the images using image processing and the calorie estimator; using one or more noninvasive sensors (such as a near-infrared light, a bioimpedance sensor, a cornea based sensor, or suitable noninvasive sensor combinations) to determine the user's glycemic index (GI) level; applying the calorie estimator and the non-invasive sensor(s) to accurately and non-invasively estimate the GI for food consumption and/or estimating calorie consumption.

In one embodiment, a partially-invasive glucose sensor such as a continuous glucose monitoring (CGM) system from IF sampling (for example a Dexcom 4) can be used. The CGM unit needs to be calibrated with a validated starting glucose value. The blood sugar level measured directly from blood with the glucose meter is provided to calibrate the CGM system. The Dexcom CGM utilizes a glucose oxidase sensor at the tip of a wire that is implanted in the subcutaneous space. The G4 sensor is inserted via a dedicated applicator by the user or clinician just under the skin where it is held in place by an adhesive to the skin. The transmitter is snapped into a platform located on top of the sensor. The data are transmitted wirelessly and are displayed on a separate receiver. This device is FDA approved to provide glucose readings for 168 hours or 7 days. The device is calibrated every 12 hours.

In other embodiments, minimally-invasive sensors harvest interstitial fluid from the body to measure with an external non-implanted sensor are being developed that disrupt the skin barrier and trap the fluid that rises to the surface (reverse iontophoresis). A patch can be placed on the abdomen or extremity that passes a small electric current through the skin to draw a measurable amount of interstitial fluid. These embodiments then analyze the interstitial fluid in the same manner as the Dexcom 4 units discussed above.

In non-invasive embodiments, glucose sensors utilizing near infrared, impedance, occlusion, Raman or radio wave spectroscopy on the wrist, finger, abdomen, or earlobe are completely noninvasive. Noninvasive glucose monitoring depends either upon on the application of optical energy into tissue followed by measurement of the interaction of the optical energy with glucose in the intravascular, interstitial fluid, and intracellular compartments, or else measurement of a physiologic phenomenon which is proportionate to the blood glucose level. The optical energy is typically applied to an appendage, such as a fingertip, an earlobe, or a forearm.

One noninvasive embodiment uses infrared light spectroscopy to measure reflection of infrared light from the skin in proportion to the glucose concentration, and distinguishes the signal of water from that of glucose which is much smaller, as well as other potential interferents in the skin. Another embodiment applies optical energy to the buccal mucosa within the mouth because this region contains no stratum corneum, the outermost dead layer of skin, to absorb the optical energy. Yet another embodiment applies to the anterior chamber of the eye various types of optical energy. Another noninvasive embodiment applies ultrasonic, electromagnetic, and thermal methods to detect glucose-related shifts in earlobe tissue. Another embodiment determines glucose from analysis of acetone and other metabolites in the breath, a process that would potentially bypass the interfering effects of skin components and microcirculation present with other methods.

In one embodiment, a plurality of LEDs can be used, each individually activated so as to emit corresponding wavelengths in sequence. In a particular embodiment, the temperature sensors measure the temperature of the LEDs, the body temperature, and the temperature of the photodiode detectors. The accelerometer indicates the sensor orientation and movement and is used by the signal processor in determining valid plethysmographs. A neural network is used to match glucose related composite parameters. Clinical data collection compares invasive blood draw measurements to noninvasive sensor measurements of the same person. Neural networks or statistical analyzers predict composite parameters CPs derived noninvasively from sensor data. The clinical data collection derives an invasive blood panel that generates a myriad of blood constituents such as blood urea nitrogen (BUN), high-density lipoprotein (HDL), low-density lipoprotein (LDL), total hemoglobin (THB), creatine (CRE) to name just a few. Data collection then assembles parameter combinations from the blood constituents so as to derive composite parameters which are then tested with the predicted composite parameters. In the neural network, the particular weights for a selected parameter is stored in weights of the network, and for statistical analyzers, the parameter weights can be stored in a look-up table. A range of composite parameters of interest is selected so as to calculate a particular blood constituent, such as blood glucose. This multi-LED system can be used on the back of a watch (FIG. 6) as a non-invasive glucose sensor. In various embodiments, the parameters are trained with invasively-measured glucose over a general population of interest; the highest correlation with invasively-measured glucose over a specific population matching a patient of interest; or the lowest error in the measurement of glucose, for example. The neural network derives glucose estimates based on the average glucose across a population of individuals according to the measured parameters. The population-based glucose estimate can also be refined by receiving an individually-calibrated glucose from a blood glucose sensor and noninvasive sensor estimate.

In yet another embodiment, glucose is detected by high-frequency radio waves around the 65 GHz range, such as those generated by ultrawide band or 5G transceivers. These waves are large enough to allow penetration through the tissue, yet simultaneously small enough to provide sufficient resolution of the blood regions inside the tissue and the blood glucose concentration can be measured at the capillary level instead at the IF. The RF waves pass through one side of a finger or ear lobe and sensed on the other side of the finger or lobe in one implementation. In another implementation, the RF waves are reflected or back-scattered from the wrist or mouth using a tooth mounted transceiver aimed at the mucosa, for example.

In other embodiments, a non-invasive sensor from a wearable device, a mobile phone or watch can act as a spectrometer which generates a spectrum of light in the visible and near infrared regions. The light is first modulated to provide light signals which can be processed to minimize background noise resulting from ambient light and other stray signals and directed to the source of the analyte, i.e. glucose, to be measured. The glucose source is blood within the tissue of an ear lobe, finger, or wrist region suitable for watch-based monitoring. The light may be transmitted through the ear lobe or may be caused to impinge on the skin surface of the tissue (such as a patient's wrist) at an angle where it is absorbed by tissue material near the surface and reflected as diffuse radiation. In either case, the light is spectrally-modified as a result of infrared absorption by the blood and tissue components, including glucose. The light can be directly beam/retrieved from the skin or can be communicated using fiber optics, among others. In the embodiment utilizing diffuse reflectance, a near infrared bandwidth in the range of 1800 to 3400 nm is preferred. Glucose is strongly absorbing in this range but, because of the similar high absorbance by water in this region, transmissive measurements are not practical. Human skin layers act as a natural filter that allow smaller glucose molecules to move to the surface, but restrict movement thereto of the larger protein molecules. Therefore, reflective skin surface measurements are less subject to protein interference than are transmissive measurements. Furthermore, a correlation between skin surface glucose and serum glucose has been established and direct measurement of the former can be converted into the latter. The intensities of the reflected light are detected by photosensor(s). For the infrared bandwidth indicated above, a lead sulfide photodetector can be used, but other types also work. The photosensors convert the measured light into signals representative of the light intensities and used to calculate the actual glucose concentration. When utilizing reflective measurements at longer wavelengths (in the range of 2700 to 3400 nm for glucose analysis, sensitivity may be substantially enhanced because of the stronger absorbance by glucose in this range.

In one embodiment an LED is used as a light source with a CMOS camera as the detector. A grating similar to compact disk (CD) grating serves as the dispersive placed about 50 mm away from the LED, and slightly tilted at an incident angle of $\alpha=5°$. The LED light passes through a pinhole with a diameter around 1 mm in front of the LED. The grating tracks are aligned normal to the incident light, and the light is then diffracted from the CD grating on the camera to detect glucose utilizing a bienzymatic cascade assay. Glucose detection can be based on a solution containing 2,2'-azino-bis(3-ethylbenz-thiazoline-6-sulfonic acid) (ABTS), horseradish peroxidase (HRP), and glucose oxidase (GOx). In this assay, glucose is catalytically converted (by GOx) into hydrogen peroxide, which in turn converts ABTS by HRP into its oxidized form (blue). For example, in the presence of 1 mM glucose, ABTS changes the color from colorless to blue and the absorption band appears at about 420 and 650 nm. Fabry-Perot interferometers configurations can also be used.

Capillary blood glucose levels at the fingertip correlate well with systemic arterial blood glucose levels. During times of blood glucose stability, identical glucose levels were demonstrated from alternate sites (e.g., forearm) as compared with finger-tip samples. However, at times of rapid change, mainly due to blood flow variability, levels from alternate sites differ considerably. Capillary blood glucose measured from the forearm is lower than fingertip values at times of rapid increases (>2 mg/dL/min) in systemic blood and higher during rapid decreases. The processor compensates accordingly for blood flow variability based on optical detection of blood flow as applied to a lookup table, a best-fit model, or a learning machine, among others. Further, the affections to the optical signals caused by the heartbeats may be obviated and samplings are not conducted at the peak of the heartbeats.

Embodiments of the glucose sensor can also monitor biomarkers of glycemic control. Hemoglobin A1c (A1C) is the best biomarker indicator of glycemic control over the past 2-3 months due to strong data predicting complications. Hemoglobin A1c refers to the non-enzymatic addition of glucose to the N-terminal valine of the hemoglobin beta chain. Assays are based upon charge and structural differences between hemoglobin molecules. Therefore, variants in hemoglobin molecules may lead to analytic interferences. It should be noted that some homozygous hemoglobin variants (HbC or HbD, or sickle cell disease) also alter erythrocyte life span and therefore, even if the assay does not show analytic interference, other methods of monitoring glycemia should be utilized, as HbA1c will be falsely low. Fructosamine refers to a family of glycated serum proteins and this family is comprised primarily of albumen and to a lesser extent, globulins, and to an even lesser extent, other circulating serum proteins. No product exists for home use that measures serum fructosamine. The largest constituent of fructosamine is glycated albumin. Several investigators and companies are developing portable assays for glycated albumin to assess overall control during periods of rapidly changing glucose levels. In these situations, an A1C test may change too slowly to capture a sudden increase or decrease in mean glycemia. The aforementioned biomarkers for measuring glycemic control, (A1C, fructosamine, and glycated albumin) only reflect mean levels of glycemia. These measures can fail to portray hyperglycemic excursions if they are balanced by hypoglycemic excursions. Plasma 1,5-anhydroglucitol (1,5-AG) is a naturally occurring dietary monosaccharide, with a structure similar to that of glucose. The 1,5-AG levels respond sensitively and rapidly to rises in serum glucose and a fall in the serum level of this analyte can indicate transient elevations of serum glucose occurring over as short a period as a few days. Measurement of 1,5-AG can be useful in assessing the prior 1-2 weeks for: 1) the degree of postprandial hyperglycemia; and 2) the mean short-term level of glycemia. This assay might prove useful in assessing the extent of glycemic variability that is present in an individual with a close-to-normal A1C level, but who is suspected to be alternating between frequent periods of hyperglycemia and hypoglycemia. In such a patient, the 1,5-AG level would be low, which would indicate frequent periods of hyperglycemia, whereas in a patient with little glycemic variability, the 1,5-AG levels would not be particularly depressed because of a lack of frequent hyperglycemic periods.

In another embodiment, the glucose concentration can be detected using a wearable eyeglass or an AV/VR goggle providing LEDs as laser sources. The user's eye is automatically scanned using a dual source of polarized radiation, each transmitting at a different wavelength at one side of the cornea of the patient. A sensor located at the other side of the cornea detects the optical rotation of the radiation that passed through the cornea. The level of glucose in the bloodstream of the patient is a function of the amount of the optical rotation of the radiation detected at the other side of the cornea of the patient. The system performs the following: scan eyes using a dual source of polarized radiation, each transmitting at a different wavelength at one side of the cornea; at the other side of the cornea, detecting the optical rotation of the radiation that passed through the cornea; determine the level of glucose in the bloodstream of the patient as a function of the amount of the optical rotation of the radiation detected at the other side of the cornea of the patient.

The result is transmitted to a remote receiver to provide non-invasive glucose determinations with high specificity and reliability. The outputs of all LEDs are individually calibrated against the gold standard blood-based glucose level, and the output of a neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user is dehydrated, the neural network learns over time to increase the glucose determination based on a deterministic or non-deterministic compensation factor. The eyewear glucose determination can be singly or can be supplemented with a bioimpedance sensor electrically coupled to the user as detailed below.

In another embodiment, a bioimpedance sensor can be operated at a high frequency (ZHF) and a low frequency (ZLF) for detecting glucose level. High frequency HF is chosen from the range from 200 kHz to 2 MHz; low frequency LF is chosen from the range from 20 kHz to 80 kHz. Electrical impedance of components of electrical impedance of body region tissues can be measured by radiating high-frequency oscillations and subsequent measuring the impedance by means of capacitive sensors. Impedance of a human body region is measured at time intervals chosen from the range from 1 sec to 10 min. ZHF is used to obtain the value of the volume of fluid in the tissues of the region. ZLF is used to obtain the value of the volume of extracellular fluid in the tissues. The increase in the metabolic component in the volume of extracellular fluid is determined by the increase of the volume of all of the fluid in comparison with the previous measurement, determining the increase in the volume of extracellular fluid in comparison with the previous measurement and subsequently calculating the difference between the increases in the volume of all of the fluid and the volume of extracellular fluid. The glucose concentration is determined by adding the amount of increase in the glucose concentration and the value of the glucose concentration determined at the previous measuring stage. Thus, knowing the initial value of glucose concentration in human blood GO and periodically taking measurements of impedance of the human body region at high and low frequencies—ZHF(tk) and ZLF(tk), the current value of glucose concentration in human blood is determined. The bioimpedance sensor characterizes changes in volumes of water spaces in human tissues, and the current value of glucose concentration in human blood, including individual physiological features of human being and moments of food intake. The measurements are periodically made and confirmed by the gold standard invasive method such as CGM or blood test strips with blood samples taken every 15 minutes. The results of the discrete measurements were recorded, and curves showing the relation of time t versus blood glucose concentration G can be generated.

In a further embodiment, a combination of sensors along with machine learning is used to accurately and non-invasively detect glucose. In one embodiment, optical sensors such as LEDs used to detect blood flow under the skin is combined with the bioimpedance sensor to improve glucose determination. The outputs of all sensors are individually calibrated against the gold standard blood-based glucose level, and the output of the neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user recently jogged 4 miles, the neural network learns over time to deduct from the glucose determination based on a deterministic or non-deterministic compensation factor.

In another embodiment, the combination of sensors along with machine learning is used to accurately and non-invasively detect glucose, and where a LED spectrometer on the wrist or ear lobe or any suitable body location is combined with the bioimpedance sensor to improve glucose determination. SpO2 or ECG based heart rate sensor(s) can be used to detect activities and calorie consumption. The outputs of all sensors are individually calibrated against the gold standard blood-based glucose level, and the output of the neural network finalizing the glucose level determination is also calibrated against the blood-based glucose level. In addition, the neural work also compensates for glucose level based on temporal activities such as exercise, food type, emotion level as detected through bioimpedance readings, among others. For example, if the user recently jogged 4 miles, the neural network learns over time to deduct from the glucose determination based on a deterministic or non-deterministic compensation factor. Moreover, if the user just ate a food item, the learning machine or neural network projects the digestive time from eating to glucose level and generates the glucose estimation after training with blood-based glucose level from invasive devices. Initially, the user received a predetermined nutritional load consisting of different food products. The blood glucose concentration is measured from the beginning of the meal until the food-related growth of glucose concentration stopped.

The sensor and insulin supply can be combined to form an artificial pancreas. This can be user operated or computer controlled. For user control of the CGM and insulin injection, one embodiment provides tiered recommendations that are based upon the meter glucose and sensor trend where patients increase or decrease the meal+correction bolus by 10-20% based upon the rate of change and provided specific instructions for responding to alarms. Other methods recommended adjustment of only the correction insulin dose by the amount needed to cover a glucose level that is incrementally higher or lower than the current glucose, based upon the trend. Another method adjusts boluses pre-meal and at least 4 hours post-meal in 0.5 unit increments based upon the trend arrow and the patient's sensitivity. A computer-controlled embodiment provides an artificial pancreas with 1) an automatic and continuous glucose monitor; 2) an implanted continuous insulin delivery system; 3) a control processor to link the insulin delivery rate to the glucose level; and 4) a radio to send the glucose level to the body surface for continuous display onto a monitor. The neural network predictive algorithm enhances sensor accuracy and reduces issues such as lag time, inadequate onset and offset of currently available rapid acting insulin analogs, meal challenges, and changes in insulin sensitivity due to circadian rhythms, exercise, menstrual cycles, and intercurrent illness. The system improves glucose control without increasing the complexity of decision-making on the part of the patient. The system can work with open-source software, such as Open Artificial Pancreas System, and Loop, for example.

The system can use single hormone (rapid acting insulin only) or dual hormone (both fast-acting insulin analog and glucagon to imitate normal physiology) as directed by the sensor/processor to provide reduced hypoglycemic events and time in hypoglycemia, as well as better overall mean glucose and glycemic variability. An adaptive meal-priming insulin bolus automatically adjusts the size of breakfast, lunch, and dinner doses by delivering 75% of the average prandial insulin provided for previous meals at that time of day improved glucose control compared to no meal announcement during dual hormone system.

Direct connectivity of blood glucose or CGM levels to cell phones or other devices improves data integrity and may also simplify the assimilation of glucose levels with other data such as insulin use, carbohydrate intake and activity levels for the purpose of facilitating insulin dose adjustments in real time or retrospectively. In one embodiment, smartphone software serves as a bolus calculator, enables self-titration of insulin, and transmits data to health care providers. The system provides immediate personalized feedback to the patient based upon glucose levels, tailored text messages, and access to certified diabetes educators in real time. A patient portal also allows for integration of data from multiple sources including third party nutrition and exercise apps. Providers can easily access dashboard reports for population and telehealth programs. The system can provide patient coaching as well as provider clinical decision support. Patients view data via their mobile device through a web portal and receive automated text messaging responses that are tailored to the data. Diabetes educators or other providers may view the data and send supplemental feedback as well.

One embodiment to guide the user on healthy food determines a glycemic index (GI), a value assigned to foods based on how slowly or how quickly those foods cause increases in blood glucose levels. Blood glucose levels above normal are toxic and can cause blindness, kidney failure, or increase cardiovascular risk. Foods low on the GI scale tend to release glucose slowly and steadily. Foods high on the glycemic index release glucose rapidly. Low GI foods tend to foster weight loss, while foods high on the GI scale help with energy recovery after exercise, or to offset hypo- (or insufficient) glycemia. Long-distance runners would tend to favor foods high on the glycemic index, while people with pre- or full-blown diabetes would need to concentrate on low GI foods as they typically can't produce sufficient quantities of insulin—which helps process blood sugar—which means they are likely to have an excess of blood glucose. The slow and steady release of glucose in low-glycemic foods is helpful in keeping blood glucose under control. A list of the glycemic index and glycemic load for more than 1,000 foods can be found in Table 1 of the article "International tables of glycemic index and glycemic load values: 2008" by Fiona S. Atkinson, Kaye Foster-Powell, and Jennie C. Brand-Miller in the December 2008 issue of Diabetes Care, Vol. 31, number 12, pages 2281-2283, the content of which is incorporated by reference. In one embodiment for GI estimation for specific food products, as well as their combination consumed during a meal, i.e., mixed food load GI estimation. One embodiment determines carbohydrate content (in grams) of the consumed food, and, based thereon, a proportion of carbohydrate content in a given food product in the total nutritional load is determined. Thereafter, the glycemic index of each food product is multiplied by its specific carbohydrate content proportion, with the results are summed up to yield the total glycemic index of the nutritional load GI.

One embodiment estimates GI based on Jennie Brand-Miller et al., "The glucose revolution: the authoritative guide to the glycemic index, the groundbreaking medical discovery" by Marlow & Company, New York, 1999, p. 33, and Jennie Brand-Miller et al., "Moreover, Glycemic index, postprandial glycemia, and the shape of the curve in healthy subjects: analysis of a database of more than 1000 foods", Am J Clin Nutr 2009; 89:97-105, the contents of which are incorporated by reference. A neural network is applied to learn the relationship of glucose and GI using reference glucose from blood glucose testing, noninvasive glucose sensor output, and GI, and after training, the neural network is used to estimate glucose and glycemic index (GI).

To collect training data, in one implementation, personalized food selection for glucose control is done after characterizing the body's reaction to specific food. This is done in 3 cycles. In the first cycle, characterization is done where the user eats 7 different meals which are all designed to contain the exact same amount of the macronutrients (carbohydrates, proteins, and fat). The day before user eats a standardized meal, no any strenuous physical activity producing sweat is performed between noon the day before the meal and 2.5 hours after the consuming the meal. The user should fast for 10-15 hours between dinner the night before and eating the standardized meal (eg. Eat dinner at 6:30 pm, fast for 10-15 hours, eat standardized meal at 7:30 am=13 hour fast). Preferably the day of the standardized meal: eat the standardized meals in the morning, within 30 minutes of waking up; consume the meal in a time span of 10 minutes without drinking a caffeinated beverage on the mornings of the standardized meals. The user should refrain from eating or drinking caffeine or other foods for a minimum of 2.5 hours after the meal (water is fine).

In one implementation, the Standardized Meals are consume in order of the following: #1—Berries—Strawberries 160 gr, Blueberries 100 gr, Raspberries 170 gr; #2—Grape meal—Grape, Red or Green (European Type, such as Thompson Seedless), Adherent Skin, Raw 275 gr; #3—Rice meal—jasmine, cooked, from frozen 155 gr; #4—Bread meal, country white 2.5 slices; #5—Pasta Dry, Enriched 70 gr; #6—Potato meal—Shredded Hash Brown, Frozen 300 gr; #7—Beans—black beans, cuban style, canned 1 can. GI for the food is looked up in a table such as Table 1 of the Atkinson publication, or data from Jennie Brand-Miller publication. GI characterizes foods by using the incremental area under the glycemic response curve relative to a similar amount of oral glucose. In this embodiment, GI characterizes foods by using the incremental area under the glycemic response curve relative to a similar amount of oral glucose. Measurement of blood glucose concentration starts when food intake begins. The measurements are performed continuously or over certain periods of time, which provides a sufficient reliably of evaluating changes in blood glucose concentration over time t. Due to food intake, blood glucose concentration of the consumer reaches a maximum value after a predetermined duration (typically 2.5 hrs) and thereafter, the glucose concentration declines and the measurement is stopped. The shape of the curve in healthy individuals and the GI of individual foods correlates strongly with the incremental and actual peak, incremental and actual glucose concentration at 60 min, and maximum amplitude of glucose excursion.

Another embodiment extends the above cycle into cycles 2 and 3 to identify personalized diet to reduce diabetic problems. For cycle #2 the food that had the strongest glucose response from cycle #1 and the selected food is tested against 3 different supplements (to try in three different days): 1—Boiled egg whites as a source of protein; 2—Fresh cream as a source of fat; and 3—Pea fiber powder as a source of fiber, for example. Cycle 2 tests if any of the supplements would help in attenuating the glucose peak. For cycle #3 the selected "optimal" diet is then tested for glucose efficacy. For the embodiment, an exemplary process to treat an insulin condition includes:
  characterizing body glucose responses to a plurality of standardized meals, each containing a predetermined number of macronutrients;
  selecting the standardized meal with a glucose peak response and further testing the selected standardized meal against supplements of protein, fat, or fiber;
  selecting the supplement best attenuating the glucose peak response for a predetermined diet;
  testing the predetermined diet for glucose efficacy in a selected glucose range.

In another embodiment, an exemplary process to treat an insulin condition includes:
  characterizing body glucose responses to a plurality of standardized conditions;
  detecting a glucose level and when the level is outside of a predetermined boundary, applying one of the standardized conditions to bring the glucose level within the predetermined boundary.

In yet another embodiment, an exemplary process to treat an insulin condition without medication includes:
  characterizing body glucose responses to a plurality of standardized conditions;
  characterizing body glucose responses to a plurality of standardized meals, each containing a predetermined number of macronutrients;
  selecting the standardized meal with a glucose peak response and further testing the selected standardized meal against supplements of protein, fat, or fiber;
  selecting the supplement best attenuating the glucose peak response for a predetermined diet;
  testing the predetermined diet for glucose efficacy in a selected glucose range;
  detecting a glucose level and when the level is outside of a predetermined boundary, applying one of the standardized conditions to bring the glucose level within the predetermined boundary.

The neural network is trained on temporal and/or spatial relationships that affect glucose level. In one embodiment, calibrated glucose data from blood-based glucose monitoring device is added to the data to train the non-invasive glucose determination logic, and such data is captured over time (temporal) and over related markers (spatial). The neural network is then able to accurately estimate glucose level based on the non-invasive sensor output and the markers that are captured by sensors such as accelerometers to detect exercise activity, cameras to detect food quantity/quality, and locality activity of life data from mobile devices (time, temperature), among others. Exemplary markers include:
  Carbohydrate quantity—Of all the three sources of energy from food (carbohydrates, protein, and fat), carbohydrates affect blood glucose the most. Accurately counting carbs is difficult, and getting the number wrong can dramatically affect blood glucose. The type of carbohydrate also matters—higher glycemic index carbs tend to spike blood glucose more rapidly.
  Carbohydrate type—veggies (especially greens), nuts, seeds, chia pudding, berries—tend to have 50%-80% of the carbs from fiber and are very low in sugar. Foods with a high-fiber-to-total-carbs ratio have a lower impact on blood glucose vs. foods with the same amount of total carbs but no fiber. In addition, the more grams of carbs that come from sugar, the higher the impact on blood glucose—even if total carbs are the same. Last, food form also matters—liquid carbs will usually increase blood glucose more quickly than solid carbs, even if the overall carbs are equal.
  Fatty foods tend to make people with diabetes more insulin resistant, meaning more insulin is often needed to cover the same amount of food relative to a similar meal without the fat. The hardest meals are those with lots of fat and lots of carbs. On a pump, using temporary basals or extended boluses (square and dual-wave) can help cover the slow, steady BG rise from high-fat meals.
  Protein—a large protein-only meal with very few carbs (e.g., salad with chicken) may cause a small rise in blood glucose (~20-50 mg/dl). The consumption of a carb-free, protein-only meal requires insulin to cover the slow rise in BG (usually an equivalent of about 10-15 grams of carbs). Pure protein powders (with no carbs) can also increase blood glucose.

Caffeine increases insulin resistance and stimulates the release of adrenaline. A large cup of coffee may cause a 20-40 mg/dl rise in blood glucose. Tea also has a small glucose effect.

Alcohol Normally, the liver releases glucose to maintain blood sugar levels. But when alcohol is consumed, the liver is busy breaking the alcohol down, and it reduces its output of glucose into the bloodstream. This can lead to a drop in blood sugar levels if the alcohol was consumed on an empty stomach. However, alcoholic drinks with carbohydrate-rich mixers (e.g., orange juice) can also raise blood sugar. When drinking alcohol, make sure you check your blood glucose often and that someone responsible nearby knows you have diabetes.

Meal-timing—eating a large late-night dinner often results in high overnight blood sugars (over 180 mg/dl), especially if it's a meal high in carbs and fat. A lighter, earlier dinner seems to improve the overnight numbers.

Dehydration—in a randomized, controlled 2001 study, dehydration raises blood glucose levels for those in a fasted state (Burge et al., Metabolism). The New York Times also reported that dehydration increases levels of the hormone vasopressin, which pushes the liver to produce blood sugar (Anahad O'Connor, January 16).

Personal microbiome—Gut bacteria ("microbiome") can affect blood glucose levels and insulin sensitivity. For example, artificial sweeteners may negatively affect the microbiome and glucose responses (Nature 2014).

Medication dose and Medication timing can also be critical. For instance, taking rapid-acting insulin (Humalog, Novolog, Apidra) 20 minutes before a meal can lead to a lower spike in glucose vs. taking it at the start of the meal or after the meal has concluded. The timing of many type 2 diabetes medications matters too—some can consistently be taken at any time of day (e.g., Januvia, Victoza), while others are most optimally taken at meals (e.g., metformin).

Steroids like prednisone can significantly increase blood glucose levels, in part by telling the liver to increase glucose production. Once prednisone is stopped, blood glucose levels usually return to normal fairly quickly.

Niacin (Vitamin B3)—Studies show niacin does increase blood glucose levels modestly. Niacin is typically prescribed to improve blood lipid levels, including HDL cholesterol and triglycerides (i.e., to improve heart health).

Light exercise activity can have a glucose-lowering effect and light exercise can act as a "dose" when blood glucose is high or trending high, especially after meals.

High intensity & moderate exercise—High-intensity exercise, such as sprinting or weight lifting, can sometimes raise blood glucose. This stems from the adrenaline response, which tells the body to release stored glucose. Often, high-intensity exercise can also drop blood glucose very rapidly (2-3 mg/dl per minute), especially if insulin was taken prior to exercise.

Level of fitness/training can affect glucose—someone starting a new activity (or starting any exercise) may see profound blood glucose drops initially, which may get smaller over time as level of fitness improves.

Time of day can affect glucose. Depending on when the patient is insulin resistant, the glucose may vary, and understanding more about morning sensitivity in exercise is especially possible through CGM.

Food & insulin timing can affect glucose. Eating too close to starting activity can lead to a low BG during activity (food has not been absorbed) followed by a high BG afterwards (food hits the bloodstream once exercise ends and digestion restarts).

Sleep—More insulin may be needed on days following less than seven hours of sleep and glucose is more variable without sufficient sleep and studies have found that not getting enough sleep leads to higher blood sugars, insulin resistance, weight gain, increased food intake, and more carb cravings.

Stress and illness can cause the body to release adrenaline (epinephrine), glucagon, growth hormone, and cortisol. As a result, more glucose is released from the liver (glucagon, adrenaline) and the body can become less sensitive to insulin (growth hormone, cortisol).

Recent hypoglycemia or "hypoglycemia begets hypoglycemia"—recent hypoglycemia impairs the body's defense mechanisms against lows. When another low comes up, it's harder to recognize the symptoms and/or the body has a harder time avoiding it.

During-sleep blood sugars—overnight blood sugars can impact on next-day time-in-range—if patient spends all night high—especially over 180 mg/dl, s/he is more likely to fight high blood sugars the whole next day. Conversely, if glucose of most of the night in range, the next day gets off to a far better start.

"Dawn phenomenon" refers to the body's daily production of hormones around 4:00-5:00 AM. During this time, the body makes less insulin and produces more glucagon, which raises blood glucose. User may need to time the dose to cover this early morning rise in glucose.

Intramuscular insulin delivery—Injecting or pumping insulin into a muscular/low-body-fat area can increase the risk of hypoglycemia—especially if it happens before activity.

Allergies—High glucose levels may occur when they have allergies, possibly due to the stress hormone cortisol.

High BG level (glucotoxicity)—High blood sugars can lead to a state known as "glucotoxicity," which can actually cause insulin resistance on its own.

Periods (menstruation)—Many women report having higher blood sugar levels a few days prior to their period starting, but some women notice a sharp drop in sugar levels.

Puberty—High levels of hormones secreted during puberty—growth hormone, testosterone, estrogen, cortisol—can increase insulin resistance. Adolescents with diabetes may need as much as 30%-50% more insulin than adults to keep their numbers within range.

Celiac disease—Untreated celiac, leading to a damaged small intestine, can increase the risk of hypoglycemia because the small intestine may no longer be able to absorb nutrients properly. Beyond Celiac also notes that untreated celiac may contribute to "irregular blood glucose levels."

Smoking—Studies suggest that smoking can increase insulin resistance, and people with diabetes who smoke are more likely than non-smokers to have trouble with insulin dosing and managing their diabetes. Smokers also have higher risks for serious complications.

Outside Temperature—Cold exposure can improve insulin sensitivity in type 2 diabetes. Some people with diabetes also report that sitting in the sun drops their blood glucose as the blood vessel dilation from heat might be responsible (similar to the effect in a hot shower or hot tub).

Sunburn stresses the body and can increase blood glucose. This is related to the previous factor on "stress/illness."

Altitude can increase insulin resistance and users may need about 20-30% more basal insulin. However, if users go to a high altitude place to do activity (e.g., skiing), less insulin may be needed.

Some embodiments track cardiovascular sensor data with glucose data to provide enhanced glucose determination. IGT may occur with almost as high a frequency as diabetes and is accompanied by an increased frequency of CVD and its risk factors. Estimates indicate that >12.0% of all ECG-indicated CHD in the population occurs in individuals with IGT and NIDDM. Further, heart rate variability (HRV) is a noninvasive measure of the autonomic nervous system, and its dynamic physiological nature provides an alternative means of blood glucose monitoring. In embodiments, Low-frequency (LF) power, high-frequency (HF) power, and total power (TP) of HRV were negatively associated with BGL in participants with DM. Additionally, the ratio of LF to HF was positively correlated with BGL. Duration of DM was also associated with multiple HRV parameters, with negative associations to both LF and HF parameters as well as TP. The neural network automatically learns links between specific HRV variables and BGL. Further, glycemia under 3 mmol/l and over 19 mmol/l is associated with significantly longer QTc interval compare to other blood glucose levels. A moderate correlation was found between a daily insulin dose and QTc duration. Glycemia under 3 mmol/l and over 19 mmol/l can prolong QT interval and, therefore, raise the risk of cardiovascular death in patients with type 1 DM. These relationships are also learned by the neural network in the processes shown in FIGS. 2A-2G that analyze glucose and heart data for health issues. The heart data can include ECG, heart rate, or blood pressure. Both hypertension and diabetes may have some underlying causes in common, and they share some risk factors. They also contribute to a worsening of each other's symptoms. The ways of managing both conditions also overlap. Insulin is the hormone that enables the body to process glucose from food and use it as energy. As a result of insulin problems, glucose cannot enter the cells to provide energy, and it accumulates in the bloodstream instead. As blood with high glucose levels travels through the body, it can cause widespread damage, including to the blood vessels and kidneys. These organs play a key role in maintaining healthy blood pressure. If they experience damage, blood pressure can rise, increasing the risk of further harm and complications. High glucose levels in the blood can increase blood pressure as the blood vessels lose their ability to stretch; the fluid in the body increases, especially if diabetes is already affecting the kidneys; and insulin resistance may involve processes that increase the risk of hypertension. Controlling blood sugar levels and blood pressure in FIGS. 2A-2G can help prevent complications.

Figure 3C:
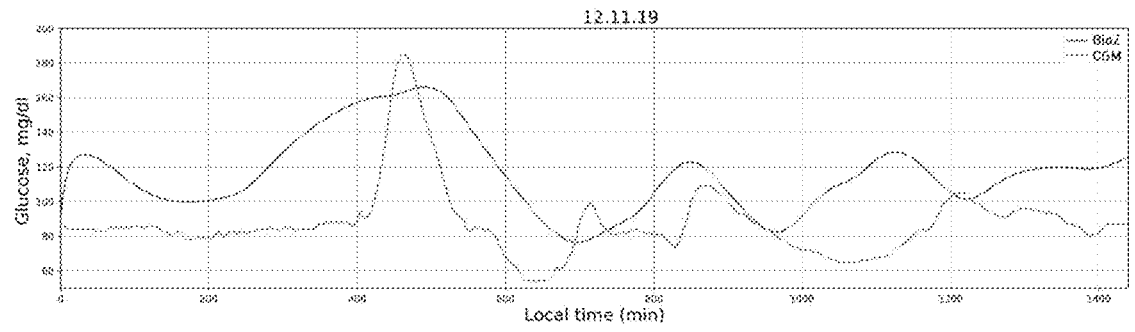
Figure 3D:
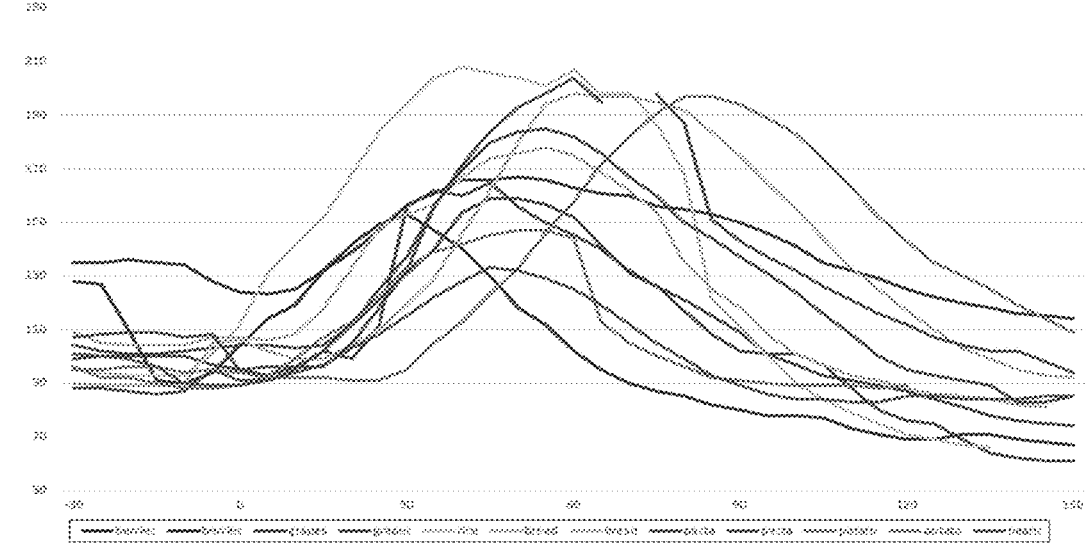
FIG. 3D shows exemplary food glucose response curves for various food items.
Figure 3B:
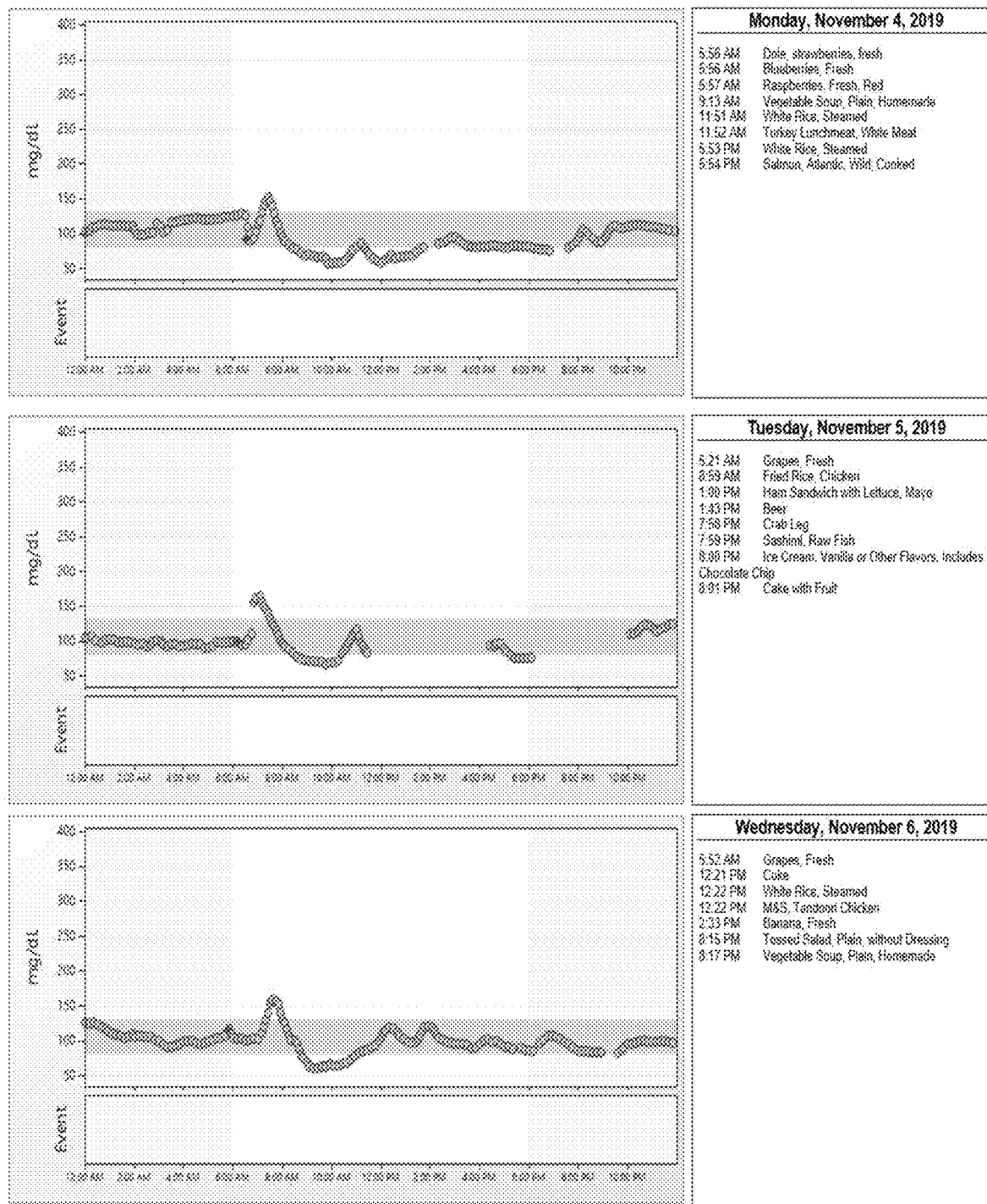

FIG. 3A shows an exemplary result from the oral glucose tolerance test (OGTT) and a corresponding isoglycemic intravenous glucose infusion (IIGI) study. The OGTT and IGI both increase blood sugar, but the OGTT tests a sugar solution drank by the user, versus during the IIGI sugar is injected directed with the IV to analyze the role of the gut hormones secreted during the OGTT, which is completely by-passed during the IIGI. FIG. 3B shows exemplary CGM outputs of a Dexcom 4 with food intake, while FIG. 3C shows an exemplary bioimpedance estimation of glucose level v. CGM output. The user receives a dose of oral glucose (the dose depends upon the length of the test). Blood samples are taken up to four times at different time points after consumption of the sugar to measure the blood glucose. The classic oral glucose tolerance test measures blood glucose levels five times over a period of three hours. Studies have shown that impaired glucose tolerance itself may be a risk factor for the development of heart disease, and impaired glucose tolerance may deserve treatment itself. FIG. 3D shows exemplary food glucose response curves for various food items. The user fasts for 10-12 hrs before digesting each food, and rests for 2.5 hrs before any significant activity is done to isolate the curve to the food digestion. As can be seen, high carb foods such as rice, bread causes higher spikes than berry and beans, for example.

Figure 4:
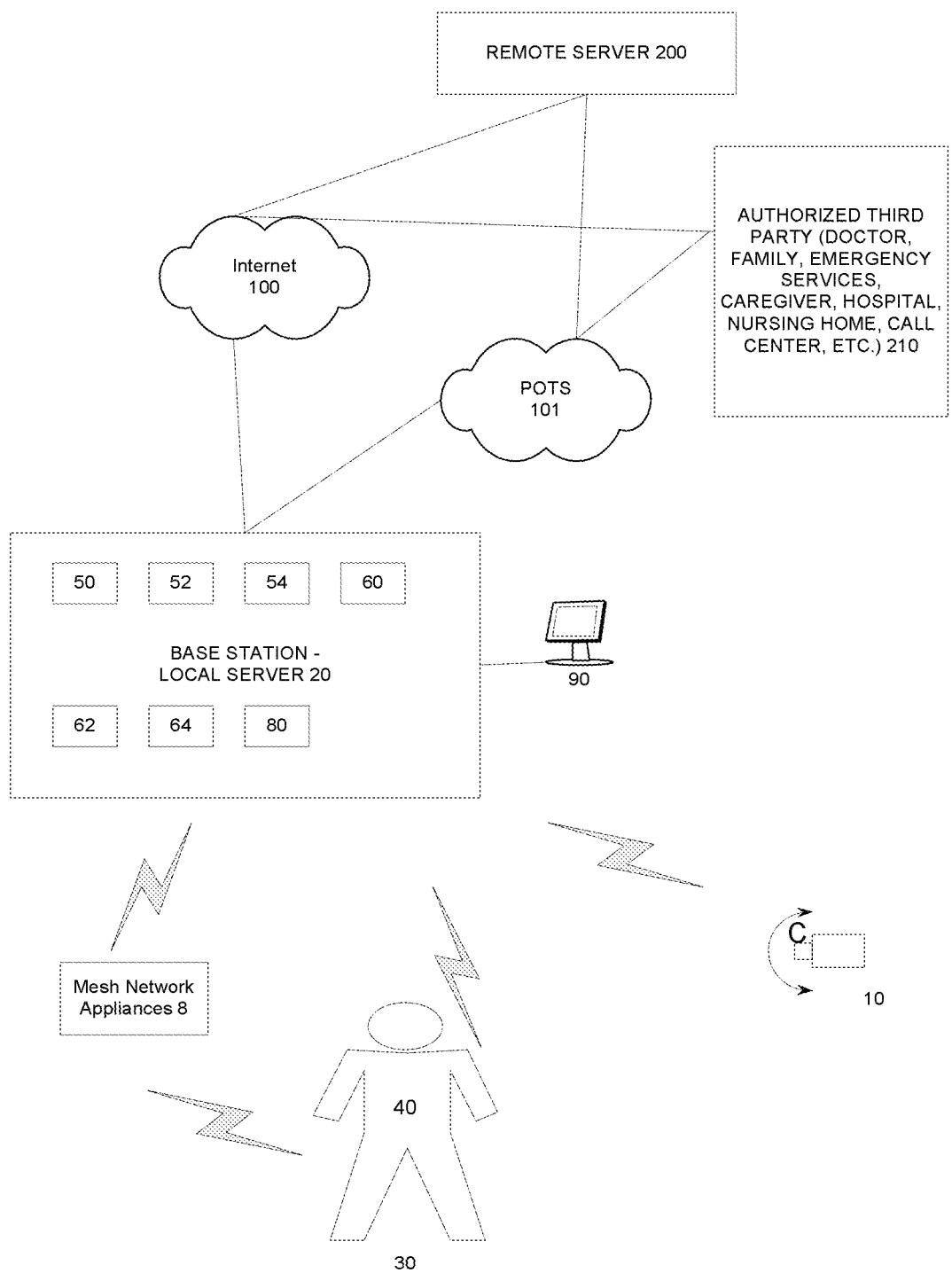
FIG. 4 shows an exemplary system for monitoring the user.
Figure 7:
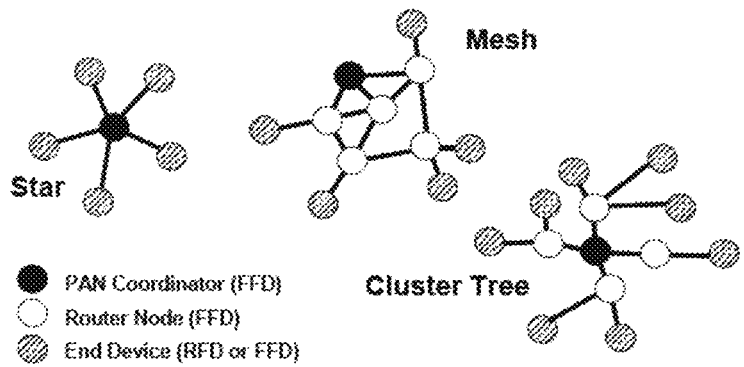
FIG. 7 shows an exemplary mesh network working with the wearable appliance of FIG. 6A-6B.

FIG. 4 shows an exemplary patient monitoring system. The system can operate in a home, a care facility, a nursing home, or a hospital. In this system, one or more mesh network appliances 8 are provided to enable wireless communication in the home monitoring system. Appliances 8 in the mesh network can include home security monitoring devices, door alarm, window alarm, home temperature control devices, fire alarm devices, among others. Appliances 8 in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. As will be discussed in more detail below, one appliance is a patient monitoring device that can be worn by the patient and includes a single or bi-directional wireless communication link, generally identified by the bolt symbol in FIG. 4, for transmitting data from the appliances 8 to the local hub or receiving station or base station server 20 by way of a wireless radio frequency (RF) link using a proprietary or non-proprietary protocol. For example, within a house, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. An individual, such as an ill or elderly grandparent, may have access to a panic transmitter or other alarm transmitter. Other sensors and/or detectors may also be included. The user may register these appliances on a central security network by entering the identification code for each registered appliance/device and/or system. The mesh network can be Zigbee network or 802.15 network. More details of the mesh network is shown in FIG. 7 and discussed in more detail below. An interoperability protocol supports the automatic configuration of an appliance with the base station. When the user operates a new appliance, the appliance announces its presence and the base station detects the presence and queries the device for its identity. If the device is not recognized, the base station determines where to find the needed software, retrieves the software, install the support software for the appliance, and then ran the device's default startup protocol that came in the downloaded installation package. The protocol allows remotely located systems or users to authenticate the identity (and possibly credentials) of the persons or organizations with whom they are interacting and ensures the privacy and authenticity of all data and command flowing between the appliances and any internal or external data storage devices. A public key infrastructure or cryptographic mechanism for facilitating these trusted interactions is used to support a global e-medicine system infrastructure. The protocol allows independently designed and implemented systems to locate each other, explore each other's capabilities (subject to each station's access control rules), to negotiate with each other and with the networks that they will use to determine how a given session will be run (for example, what Quality of Service requirements will be levied and what resources will be leased from each other), and to then conduct collaborative operations. The protocol contains instructions regarding the kinds of components that are needed to support the protocol's operation, the ways in which these components need to be interconnected, and events that are to be monitored during the time that the protocol is active.

A plurality of monitoring cameras 10 may be placed in various predetermined positions in a home of a patient 30. The cameras 10 can be wired or wireless. For example, the cameras can communicate over infrared links or over radio links conforming to the 802X (e.g. 802.11A, 802.11B, 802.11G, 802.15) standard or the Bluetooth standard to a base station/server 20 may communicate over various communication links, such as a direct connection, such a serial connection, USB connection, Firewire connection or may be optically based, such as infrared or wireless based, for example, home RF, IEEE standard 802.11a/b, Bluetooth or the like. In one embodiment, appliances 8 monitor the patient and activates the camera 10 to capture and transmit video to an authorized third party for providing assistance should the appliance 8 detects that the user needs assistance or that an emergency had occurred.

The base station/server 20 stores the patient's ambulation pattern and vital parameters and can be accessed by the patient's family members (sons/daughters), physicians, caretakers, nurses, hospitals, and elderly community. The base station/server 20 may communicate with the remote server 200 by DSL, T-1 connection over a private communication network or a public information network, such as the Internet 100, among others.

The patient 30 may wear one or more wearable patient monitoring appliances such as wrist-watches or clip on devices or electronic jewelry to monitor the patient. One wearable appliance such as a wrist-watch includes sensors 40, for example devices for sensing ECG, EKG, blood pressure, sugar level, among others. The glucose sensors are detailed above in FIGS. 1A-1G. In one embodiment, the sensors 40 are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors 40 can individually transmit data to the server 20 using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor 40 can also include an indoor positioning system or alternatively a global position system (GPS) receiver that relays the position and ambulatory patterns of the patient to the server 20 for mobility tracking.

In one embodiment, the sensors 40 for monitoring vital signs are enclosed in a wrist-watch sized case supported on a wrist band. The sensors can be attached to the back of the case. For example, in one embodiment, Cygnus' AutoSensor (Redwood City, Calif.) is used as a glucose sensor. A low electric current pulls glucose through the skin. Glucose is accumulated in two gel collection discs in the AutoSensor. The AutoSensor measures the glucose and a reading is displayed by the watch.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

The case may be of a number of variations of shape but can be conveniently made a rectangular, approaching a box-like configuration. The wrist-band can be an expansion band or a wristwatch strap of plastic, leather or woven material. The wrist-band further contains an antenna for transmitting or receiving radio frequency signals. The wrist-band and the antenna inside the band are mechanically coupled to the top and bottom sides of the wrist-watch housing. Further, the antenna is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing contains the processor and associated peripherals to provide the human-machine interface. A display is located on the front section of the housing. A speaker, a microphone, and a plurality of push-button switches and are also located on the front section of housing. An infrared LED transmitter and an infrared LED receiver are positioned on the right side of housing to enable the watch to communicate with another computer using infrared transmission.

In another embodiment, the sensors 40 are mounted on the patient's clothing. For example, sensors can be woven into a single-piece garment (an undershirt) on a weaving machine. A plastic optical fiber can be integrated into the structure during the fabric production process without any discontinuities at the armhole or the seams. An interconnection technology transmits information from (and to) sensors mounted at any location on the body thus creating a flexible "bus" structure. T-Connectors—similar to "button clips" used in clothing—are attached to the fibers that serve as a data bus to carry the information from the sensors (e.g., EKG sensors) on the body. The sensors will plug into these connectors and at the other end similar T-Connectors will be used to transmit the information to monitoring equipment or personal status monitor. Since shapes and sizes of humans will be different, sensors can be positioned on the right locations for all patients and without any constraints being imposed by the clothing. Moreover, the clothing can be laundered without any damage to the sensors themselves. In addition to the fiber optic and specialty fibers that serve as sensors and data bus to carry sensory information from the wearer to the monitoring devices, sensors for monitoring the respiration rate can be integrated into the structure.

In another embodiment, instead of being mounted on the patient, the sensors can be mounted on fixed surfaces such as walls or tables, for example. One such sensor is a motion detector. Another sensor is a proximity sensor. The fixed sensors can operate alone or in conjunction with the cameras 10. In one embodiment where the motion detector operates with the cameras 10, the motion detector can be used to trigger camera recording. Thus, as long as motion is sensed, images from the cameras 10 are not saved. However, when motion is not detected, the images are stored and an alarm may be generated. In another embodiment where the motion detector operates stand alone, when no motion is sensed, the system generates an alarm.

The server 20 also executes one or more software modules to analyze data from the patient. A module 50 monitors the patient's vital signs such as ECG/EKG and generates warnings should problems occur. In this module, vital signs can be collected and communicated to the server 20 using wired or wireless transmitters. In one embodiment, the server 20 feeds the data to a statistical analyzer such as a neural network which has been trained to flag potentially dangerous conditions. The neural network can be a back-propagation neural network, for example. In this embodiment, the statistical analyzer is trained with training data where certain signals are determined to be undesirable for the patient, given his age, weight, and physical limitations, among others. For example, the patient's glucose level should be within a well established range, and any value outside of this range is flagged by the statistical analyzer as a dangerous condition. As used herein, the dangerous condition can be specified as an event or a pattern that can cause physiological or psychological damage to the patient. Moreover, interactions between different vital signals can be accounted for so that the statistical analyzer can take into consideration instances where individually the vital signs are acceptable, but in certain combinations, the vital signs can indicate potentially dangerous conditions. Once trained, the data received by the server 20 can be appropriately scaled and processed by the statistical analyzer. In addition to statistical analyzers, the server 20 can process vital signs using rule-based inference engines, fuzzy logic, as well as conventional if-then logic. Additionally, the server can process vital signs using Hidden Markov Models (HMMs), dynamic time warping, or template matching, among others.

Through various software modules, the system reads video sequence and generates a 3D anatomy file out of the sequence. The proper bone and muscle scene structure are created for head and face. A based profile stock phase shape will be created by this scene structure. Every scene will then be normalized to a standardized viewport.

A module monitors the patient ambulatory pattern and generates warnings should the patient's patterns indicate that the patient has fallen or is likely to fall. 3D detection is used to monitor the patient's ambulation. In the 3D detection process, by putting 3 or more known coordinate objects in a scene, camera origin, view direction and up vector can be calculated and the 3D space that each camera views can be defined.

In one embodiment with two or more cameras, camera parameters (e.g. field of view) are preset to fixed numbers. Each pixel from each camera maps to a cone space. The system identifies one or more 3D feature points (such as a birthmark or an identifiable body landmark) on the patient. The 3D feature point can be detected by identifying the same point from two or more different angles. By determining the intersection for the two or more cones, the system determines the position of the feature point. The above process can be extended to certain feature curves and surfaces, e.g. straight lines, arcs; flat surfaces, cylindrical surfaces. Thus, the system can detect curves if a feature curve is known as a straight line or arc. Additionally, the system can detect surfaces if a feature surface is known as a flat or cylindrical surface. The further the patient is from the camera, the lower the accuracy of the feature point determination. Also, the presence of more cameras would lead to more correlation data for increased accuracy in feature point determination. When correlated feature points, curves and surfaces are detected, the remaining surfaces are detected by texture matching and shading changes. Predetermined constraints are applied based on silhouette curves from different views. A different constraint can be applied when one part of the patient is occluded by another object. Further, as the system knows what basic organic shape it is detecting, the basic profile can be applied and adjusted in the process.

In a single camera embodiment, the 3D feature point (e.g. a birth mark) can be detected if the system can identify the same point from two frames. The relative motion from the two frames should be small but detectable. Other features curves and surfaces will be detected correspondingly, but can be tessellated or sampled to generate more feature points. A transformation matrix is calculated between a set of feature points from the first frame to a set of feature points from the second frame. When correlated feature points, curves and surfaces are detected, the rest of the surfaces will be detected by texture matching and shading changes.

Each camera exists in a sphere coordinate system where the sphere origin (0,0,0) is defined as the position of the camera. The system detects theta and phi for each observed object, but not the radius or size of the object. The radius is approximated by detecting the size of known objects and scaling the size of known objects to the object whose size is to be determined. For example, to detect the position of a ball that is 10 cm in radius, the system detects the ball and scales other features based on the known ball size. For human, features that are known in advance include head size and leg length, among others. Surface texture can also be detected, but the light and shade information from different camera views is removed. In either single or multiple camera embodiments, depending on frame rate and picture resolution, certain undetected areas such as holes can exist. For example, if the patient yawns, the patient's mouth can appear as a hole in an image. For 3D modeling purposes, the hole can be filled by blending neighborhood surfaces. The blended surfaces are behind the visible line.

To obtain services from external sources, the base station 20 makes a request based on the information collected from the multiple devices and issues the request to the remote server 200. The remote server 200 acts as a proxy/gateway to request, consume, and/or distribute web services from a variety of content sources. In this regard, the communications between the base station 20 and the server 200 are encrypted to protect patient identifiable information and other private details of the person. Also, a variety of services may be aggregated and cached, thus providing a faster response time and better use of network bandwidth. The server 200 may store information regarding the devices and/or service providers. In this regard, the server 200 may include a user profile database that maintains an updated copy of the user profile and application data so that intelligent content services and synchronization among different devices may be provided. In a wireless network environment, availability may not always be guaranteed so that another mechanism, such as, for example, a queue structure, may be required to save the data, profiles, and results for later retrieval.

The devices 8, 10 and 40 register with the base station 20 and provide information regarding the capabilities of the device, including, for example, device type (EKG, EMG, blood pressure sensor, etc.) memory size, processing capacity, and supported protocols and connectivity. The base station 20 processes service requests from the devices and may enhance the service requests and/or combine them collectively before issuing the requests in response to queries from a requester such as a doctor who polls the server 200 on the status of the patient. Upon receiving the request from the doctor through the server 200, the base station 20 "tailors" the request to suit the proper device capability before relaying it the appropriate device. Hence, the devices 8, 10 and 40, issue requests on behalf of themselves and receive responses individually according to their particular capabilities while the base station 40 customizes and combines requests/responses to simplify and/or improve communication efficiency. Data is automatically synchronized to maintain a consistent state of the devices, regardless, for example, of network availability and/or unreliable networks.

In another embodiment, instead of having the doctor using a thin-client, a remote user such as a patient representative (attorney in fact), family member, or a doctor can be running his/her own computer system that is registered with the server 200 as an authorized user. The server 200 forwards such registration to the base station 20 and the base station registers the doctor's computer as an authorized doctor base station in the network. The doctor base station in turn communicates with devices in the doctor's office such as digital scales, blood pressure measurement devices, digital X-ray machines, glucose measurement devices, digital scanners such as computer aided tomography (CAT) scanners and nuclear magnetic resonance (NMR) scanners, among others. These devices capture patient information through a unique patient identifier and the data is stored in the doctor base station and can also be uploaded to the remote server 200 to store data. Since numerous base stations can exist that provide medical information on a patient (different doctors/specialists, different hospitals and care centers), the server 200 performs data synchronization to ensure that all base stations have access to the latest information.

To allow the remote person such as a physician or a family member to monitor a patient, a plurality of user interface modules enable the remote person to control each appliance and to display the data generated by the appliance. In one example scenario, an EKG sensor wirelessly communicates with the patient base station and outputs a continuous EKG waveform. A pattern recognizer or analyzer positioned at the doctor's station accepts waveform data and generates a variety of statistics that characterize the waveform and can generate alarms or messages to the doctor if certain predefined conditions are met. While it is operating, the EKG sends its waveform data to its subscribing components or modules at the doctor's office and the analyzer processes the data and sends summaries or recommendations to the doctor for viewing. If, during the operation of this network of components, any of these components experience an event that compromises its ability to support the protocol (e.g., the EKG unit is disconnected or deactivated from the base station), then the affected components notify the remote base station of a disconnected appliance. When finished with the EKG data sampling, the user may "deselect" the device on the user interface framework, which results in the EKG user interface module being disabled and terminating data collection by the EKG device. In turn, the protocol instructs each of the leased components to terminate its subscriptions. The protocol then notifies the registry that it is vacating its lease on these components and tells the user interface event handler that it is ending.

The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format.

The appliances can communicate data conforming to the interoperable format over one of: cellular protocol, ZigBee protocol, Bluetooth protocol, WiFi protocol, WiMAX protocol, USB protocol, ultrawideband protocol. The appliances can communicate over two or more protocols. The first medical appliance can transmit the first vital information over a first protocol (such as Bluetooth protocol) to a computer, wherein the computer transmits the first vital information to the second medical appliance over a second protocol (such as ZigBee protocol). The computer can then transmit to a hospital or physician office using broadband such as WiMAX protocol or cellular protocol. The computer can perform the interoperable format conversion for the appliances or devices, or alternatively each appliance or device can perform the format conversion. Regardless of which device performs the protocol conversion and format conversion, the user does not need to know about the underlying format or protocol in order to use the appliances. The user only needs to plug an appliance into the network, the data transfer is done automatically so that the electronic "plumbing" is not apparent to the user. In this way, the user is shielded from the complexity supporting interoperability.

A module 54 monitors patient activity and generates a warning if the patient has fallen. In one implementation, the system detects the speed of center of mass movement. If the center of mass movement is zero for a predetermined period, the patient is either sleeping or unconscious. The system then attempts to signal the patient and receive confirmatory signals indicating that the patient is conscious. If patient does not confirm, then the system generates an alarm. For example, if the patient has fallen, the system would generate an alarm signal that can be sent to friends, relatives or neighbors of the patient. Alternatively, a third party such as a call center can monitor the alarm signal. Besides monitoring for falls, the system performs video analysis of the patient. For example, during a particular day, the system can determine the amount of time for exercise, sleep, and entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the sensor for 13 minutes and don't show up anywhere else in the house, the system infers that patient had taken a bath or a shower. However, if a person falls and remains motionless for a predetermined period, the system would record the event and notify a designated person to get assistance. Details of the fall detection are disclosed in the Tran U.S. Pat. No. 9,820,658.

In one example, once a stroke occurs, the system detects a slow motion of patient as the patient rests or a quick motion as the patient collapses. By adjust the sensitivity threshold, the system detects whether a patient is uncomfortable and ready to rest or collapse.

If the center of mass movement ceases to move for a predetermined period, the system can generate the warning. In another embodiment, before generating the warning, the system can request the patient to confirm that he or she does not need assistance. The confirmation can be in the form of a button that the user can press to override the warning. Alternatively, the confirmation can be in the form of a single utterance that is then detected by a speech recognizer.

In another embodiment, the confirmatory signal is a patient gesture. The patient can nod his or her head to request help and can shake the head to cancel the help request. Alternatively, the patient can use a plurality of hand gestures to signal to the server 20 the actions that the patient desires.

By adding other detecting mechanism such as sweat detection, the system can know whether patient is uncomfortable or not. Other items that can be monitored include chest movement (frequency and amplitude) and rest length when the patient sits still in one area, among others.

Besides monitoring for falls, the system performs video analysis of the patient. For example, during a particular day, the system can determine the amount of time for exercise, sleep, entertainment, among others. The network of sensors in a patient's home can recognize ordinary patterns—such as eating, sleeping, and greeting visitors—and to alert caretakers to out-of-the-ordinary ones—such as prolonged inactivity or absence. For instance, if the patient goes into the bathroom then disappears off the camera 10 view for a predetermined period and does not show up anywhere else in the house, the system infers that patient had taken a bath or a shower. However, if a person falls and remains motionless for a predetermined period, the system would record the event and notify a designated person to get assistance.

In one embodiment, changes in the patient's skin color can be detected by measuring the current light environment, properly calibrating color space between two photos, and then determining global color change between two states. Thus, when the patient's face turn red, based on the redness, a severity level warning is generated.

In another embodiment, changes in the patient's face are detected by analyzing a texture distortion in the images. If the patient perspires heavily, the texture will show small glisters, make-up smudges, or sweat/tear drippings. Another example is, when long stretched face will be detected as texture distortion. Agony will show certain wrinkle texture patterns, among others.

The system can also utilize high light changes. Thus, when the patient sweats or changes facial appearance, different high light areas are shown, glisters reflect light and pop up geometry generates more high light areas.

A module 62 analyzes facial changes such as facial asymmetries. The change will be detected by superimpose a newly acquired 3D anatomy structure to a historical (normal) 3D anatomy structure to detect face/eye sagging or excess stretch of facial muscles.

In one embodiment, the system determines a set of base 3D shapes, which are a set of shapes which can represent extremes of certain facial effects, e.g. frown, open mouth, smiling, among others. The rest of the 3D face shape can be generated by blending/interpolating these base shapes by applied different weight to each base shapes.

The base 3D shape can be captured using 1) a 3D camera such as cameras from Steinbichler, Genex Technology, Minolta 3D, Olympus 3D or 2) one or more 2D camera with preset camera field of view (FOV) parameters. To make it more accurate, one or more special markers can be placed on patient's face. For example, a known dimension square stick can be placed on the forehead for camera calibration purposes.

Using the above 3D detection method, facial shapes are then extracted. The proper features (e.g. a wrinkle) will be detected and attached to each base shape. These features can be animated or blended by changing the weight of different shape(s). The proper features change can be detected and determine what type of facial shape it will be.

Next, the system super-imposes two 3D facial shapes (historical or normal facial shapes and current facial shapes). By matching features and geometry of changing areas on the face, closely blended shapes can be matched and facial shape change detection can be performed. By overlaying the two shapes, the abnormal facial change such as sagging eyes or mouth can be detected.

The above processes are used to determine paralysis of specific regions of the face or disorders in the peripheral or central nervous system (trigeminal paralysis; CVA, among others). The software also detects eyelid positions for evidence of ptosis (incomplete opening of one or both eyelids) as a sign of innervation problems (CVA; Homer syndrome, for example). The software also checks eye movements for pathological conditions, mainly of neurological origin are reflected in aberrations in eye movement. Pupil reaction is also checked for abnormal reaction of the pupil to light (pupil gets smaller the stronger the light) may indicate various pathological conditions mainly of the nervous system. In patients treated for glaucoma pupillary status and motion pattern may be important to the follow-up of adequate treatment. The software also checks for asymmetry in tongue movement, which is usually indicative of neurological problems. Another check is neck veins: Engorgement of the neck veins may be an indication of heart failure or obstruction of normal blood flow from the head and upper extremities to the heart. The software also analyzes the face, which is usually a mirror of the emotional state of the observed subject. Fear, joy, anger, apathy are only some of the emotions that can be readily detected, facial expressions of emotions are relatively uniform regardless of age, sex, race, etc. This relative uniformity allows for the creation of computer programs attempting to automatically diagnose people's emotional states.

Speech recognition is performed to determine a change in the form of speech (slurred speech, difficulties in the formation of words, for example) may indicated neurological problems, such an observation can also indicate some outward effects of various drugs or toxic agents.

In one embodiment shown in FIG. 5A, a facial expression analysis process is done, and depending on where patient is facing, for a side facing view, silhouette edges will provide unique view information because there is a one to one correspondent between the view and silhouette shape.

Once the patient's face has been aligned to the right view, exemplary pseudo code to detect facial expression is as follows:

1. Detect shape change. The shape can be match by superimpose different expression shapes to current shape, and judge by minimum discrepancy. E.g. wide mouth open.
2. Detect occlusion. Sometime the expression can be detected by occlusal of another objects, e.g., teeth show up means mouth is open.
3. Detect texture map change. The expression can relate to certain texture changes, if patient smile, certain wrinkles patents will show up.
4. Detect highlight change. The expression can relate to certain high light changes, if patient sweats or cries, different highlight area will show up.

Speech recognition can be performed in one embodiment to determine a change in the form of speech (slurred speech, difficulties in the formation of words, for example) may indicated neurological problems, such an observation can also indicate some outward effects of various drugs or toxic agents.

A module communicates with a third party such as the police department, a security monitoring center, or a call center. The module operates with a POTS telephone and can use a broadband medium such as DSL or cable network if available. The module 80 requires that at least the telephone is available as a lifeline support. In this embodiment, duplex sound transmission is done using the POTS telephone network. The broadband network, if available, is optional for high resolution video and other advanced services transmission.

Alternatively, the system can ask a confirmatory question to the patient through text to speech software. The patient can be orally instructed by the health practitioner to conduct specific physical activities such as specific arm movements, walking, bending, among others. The examination begins during the initial conversation with the monitored subject. Any changes in the spontaneous gestures of the body, arms and hands during speech as well as the fulfillment of nonspecific tasks are important signs of possible pathological events. The monitoring person can instruct the monitored subject to perform a series of simple tasks which can be used for diagnosis of neurological abnormalities. These observations may yield early indicators of the onset of a disease.

A network 100 such as the Internet receives images from the server 20 and passes the data to one or more remote servers 200. The images are transmitted from the server 200 over a secure communication link such as virtual private network (VPN) to the remote server(s) 200.

In one embodiment where cameras are deployed, the server 200 collects data from a plurality of cameras and uses the 3D images technology to determine if the patient needs help. The system can transmit video (live or archived) to the friend, relative, neighbor, or call center for human review. At each viewer site, after a viewer specifies the correct URL to the client browser computer, a connection with the server 200 is established and user identity authenticated using suitable password or other security mechanisms. The server 200 then retrieves the document from its local disk or cache memory storage and transmits the content over the network. In the typical scenario, the user of a Web browser requests that a media stream file be downloaded, such as sending, in particular, the URL of a media redirection file from a Web server. The media redirection file (MRF) is a type of specialized Hypertext Markup Language (HTML) file that contains instructions for how to locate the multimedia file and in what format the multimedia file is in. The Web server returns the MRF file to the user's browser program. The browser program then reads the MRF file to determine the location of the media server containing one or more multimedia content files. The browser then launches the associated media player application program and passes the MRF file to it. The media player reads the MRF file to obtain the information needed to open a connection to a media server, such as a URL, and the required protocol information, depending upon the type of medial content is in the file. The streaming media content file is then routed from the media server down to the user.

In the camera embodiment, the transactions between the server 200 and one of the remote servers 200 are detailed. The server 200 compares one image frame to the next image frame. If no difference exists, the duplicate frame is deleted to minimize storage space. If a difference exists, only the difference information is stored as described in the JPEG standard. This operation effectively compresses video information so that the camera images can be transmitted even at telephone modem speed of 64$k$ or less. More aggressive compression techniques can be used. For example, patient movements can be clusterized into a group of known motion vectors, and patient movements can be described using a set of vectors. Only the vector data is saved. During view back, each vector is translated into a picture object which is suitably rasterized. The information can also be compressed as motion information.

Next, the server 200 transmits the compressed video to the remote server 200. The server 200 stores and caches the video data so that multiple viewers can view the images at once since the server 200 is connected to a network link such as telephone line modem, cable modem, DSL modem, and ATM transceiver, among others.

The system can also monitor the patient's gait pattern and generate warnings should the patient's gait patterns indicate that the patient is likely to fall. The system will detect patient skeleton structure, stride and frequency; and based on this information to judge whether patient has joint problem, asymmetrical bone structure, among others. The system can store historical gait information, and by overlaying current structure to the historical (normal) gait information, gait changes can be detected. In the camera embodiment, an estimate of the gait pattern is done using the camera. In a camera-less embodiment, the gait can be sensed by providing a sensor on the floor and a sensor near the head and the variance in the two sensor positions are used to estimate gait characteristics.

The system also provides a patient interface 90 to assist the patient in easily accessing information. In one embodiment, the patient interface includes a touch screen; voice-activated text reading; one touch telephone dialing; and video conferencing. The touch screen has large icons that are pre-selected to the patient's needs, such as his or her favorite web sites or application programs. The voice activated text reading allows a user with poor eye-sight to get information from the patient interface 90. Buttons with pre-designated dialing numbers, or video conferencing contact information allow the user to call a friend or a healthcare provider quickly.

In one embodiment, medicine for the patient is tracked using radio frequency identification (RFID) tags. In this embodiment, each drug container is tracked through an RFID tag that is also a drug label. RFID readers communicate directly with the RFID tags and send encrypted usage data over the patient's network to the server 200 and eventually over the Internet 100. The readers can be built directly into the walls or the cabinet doors.

After receiving the medicine container, the patient places the medicine in a medicine cabinet, which is also equipped with a tag reader. This smart cabinet then tracks all medicine stored in it. It can track the medicine taken, how often the medicine is restocked and can let the patient know when a particular medication is about to expire. At this point, the server 200 can order these items automatically. The server 200 also monitors drug compliance, and if the patient does not remove the bottle to dispense medication as prescribed, the server 200 sends a warning to the healthcare provider.

The database tracks typical arm and leg movements to determine whether the user is experiencing muscle weakness reflective of a stroke. If muscle weakness is detected, the system presents the user with additional tests to confirm the likelihood of a stroke attack or out of control glucose level. If the information indicates a stroke attack or out of control glucose level had occurred, the system stores the time of the stroke/extreme glucose detection and calls for emergency assistance to get timely treatment for the stroke. The user's habits and movements can be determined by the system for stroke attack or out of control glucose level detection. This is done by tracking location, ambulatory travel vectors and time in a database. If the user typically sleeps between 10 pm to 6 am, the location would reflect that the user's location maps to the bedroom between 10 pm and 6 am. In one exemplary system, the system builds a schedule of the user's activity as follows:

| Location | Time Start | Time End | Heart Rate |
|---|---|---|---|
| Bed room | 10 pm | 6 am | 60-80 |
| Gym room | 6 am | 7 am | 90-120 |
| Bath room | 7 am | 7:30 am | 85-120 |
| Dining room | 7:30 am | 8:45 am | 80-90 |
| Home Office | 8:45 am | 11:30 am | 85-100 |
| ... | | | |
| ... | | | |

The habit tracking is adaptive in that it gradually adjusts to the user's new habits. If there are sudden changes, the system flags these sudden changes for follow up. For instance, if the user spends three hours in the bathroom, the system prompts the third party (such as a call center) to follow up with the patient to make sure he or she does not need help.

In one embodiment, data driven analyzers may be used to track the patient's habits. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient's habits or ambulation patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's daily activities such as start and stop times of interactions of different interactions are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences.

Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's habits. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm.

Substantially any type of learning system or process may be employed to determine the user's ambulatory and living patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination.

The system allows patients to conduct a low-cost, comprehensive, real-time monitoring of their vital parameters such as ambulation and falls. Information can be viewed using an Internet-based website, a personal computer, or simply by viewing a display on the monitor. Data measured several times each day provide a relatively comprehensive data set compared to that measured during medical appointments separated by several weeks or even months. This allows both the patient and medical professional to observe trends in the data, such as a gradual increase or decrease in blood pressure, which may indicate a medical condition. The invention also minimizes effects of white coat syndrome since the monitor automatically makes measurements with basically no discomfort; measurements are made at the patient's home or work, rather than in a medical office.

The wearable appliance is small, easily worn by the patient during periods of exercise or day-to-day activities, and non-invasively measures blood pressure can be done in a matter of seconds without affecting the patient. An onboard or remote processor can analyze the time-dependent measurements to generate statistics on a patient's blood pressure (e.g., average pressures, standard deviation, beat-to-beat pressure variations) that are not available with conventional devices that only measure systolic and diastolic blood pressure at isolated times.

The wearable appliance provides an in-depth, cost-effective mechanism to evaluate a patient's health condition. Certain cardiac conditions can be controlled, and in some cases predicted, before they actually occur. Moreover, data from the patient can be collected and analyzed while the patient participates in their normal, day-to-day activities.

Software programs associated with the Internet-accessible website, secondary software system, and the personal computer analyze the blood pressure, and heart rate, and pulse oximetry values to characterize the patient's cardiac condition. These programs, for example, may provide a report that features statistical analysis of these data to determine averages, data displayed in a graphical format, trends, and comparisons to doctor-recommended values.

When the appliance cannot communicate with the mesh network, the appliance simply stores information in memory and continues to make measurements. The watch component automatically transmits all the stored information (along with a time/date stamp) when it comes in proximity to the wireless mesh network, which then transmits the information through the wireless network.

In one embodiment, the server provides a web services that communicate with third party software through an interface. To generate vital parameters such as blood pressure information for the web services software interface, the patient continuously wears the blood-pressure monitor for a short period of time, e.g. one to two weeks after visiting a medical professional during a typical check up' or after signing up for a short-term monitoring program through the website. In this case, the wearable device such as the watch measures mobility through the accelerometer and blood pressure in a near-continuous, periodic manner such as every fifteen minutes. This information is then transmitted over the mesh network to a base station that communicates over the Internet to the server.

To view information sent from the blood-pressure monitor and fall detector on the wearable appliance, the patient or an authorized third party such as family members, emergency personnel, or medical professional accesses a patient user interface hosted on the web server 200 through the Internet 100 from a remote computer system. The patient interface displays vital information such as ambulation, blood pressure and related data measured from a single patient. The system may also include a call center, typically staffed with medical professionals such as doctors, nurses, or nurse practioners, whom access a care-provider interface hosted on the same website on the server 200. The care-provider interface displays vital data from multiple patients.

The wearable appliance has an indoor positioning system and processes these signals to determine a location (e.g., latitude, longitude, and altitude) of the monitor and, presumably, the patient. This location could be plotted on a map by the server, and used to locate a patient during an emergency, e.g. to dispatch an ambulance. The server 200 may communicate with a business process outsourcing (BPO) company or a call center to provide central monitoring in an environment where a small number of monitoring agents can cost effectively monitor multiple people 24 hours a day. A call center agent, a clinician or a nursing home manager may monitor a group or a number of users via a summary "dashboard" of their readings data, with ability to drill-down into details for the collected data. A clinician administrator may monitor the data for and otherwise administer a number of users of the system. A summary "dashboard" of readings from all Patients assigned to the Administrator is displayed upon log in to the Portal by the Administrator. Readings may be color coded to visually distinguish normal vs. readings that have generated an alert, along with description of the alert generated. The Administrator may drill down into the details for each Patient to further examine the readings data, view charts etc. in a manner similar to the Patient's own use of the system. The Administrator may also view a summary of all the appliances registered to all assigned Patients, including but not limited to all appliance identification information. The Administrator has access only to information about Patients that have been assigned to the Administrator by a Super Administrator. This allows for segmenting the entire population of monitored Patients amongst multiple Administrators. The Super Administrator may assign, remove and/or reassign Patients amongst a number of Administrators. In one embodiment, a physician, other health care practitioner, or emergency personnel is provided with access to patient medical information through the server 200. In one embodiment, if the wearable appliance detects that the patient needs help, or if the patient decides help is needed, the system can call his or her primary care physician.

FIG. 5C shows an exemplary process to monitor patient. First, the process sets up mesh network appliances (1000). Next, the process determines patient position using in-door positioning system (1002). The process then determines patient movement using accelerometer output (1004). Sharp accelerations may be used to indicate fall. Further, the z axis accelerometer changes can indicate the height of the appliance from the floor and if the height is near zero, the system infers that the patient had fallen. The system can also determine vital parameter including patient heart rate (1006). The system determines if patient needs assistance based on in-door position, fall detection and vital parameter (1008). If a fall is suspected, the system confirms the fall by communicating with the patient prior to calling a third party such as the patient's physician, nurse, family member, 911, 511, 411, or a paid call center to get assistance for the patient (1010). If confirmed or if the patient is non-responsive, the system contacts the third party and sends voice over mesh network to appliance on the patient to allow one or more third parties to talk with the patient (1012). If needed, the system calls and/or conferences emergency personnel into the call (1014).

In one embodiment, if the patient is outside of the mesh network range such as when the user is traveling away from his/her home, the system continuously records information into memory until the home mesh network is reached or until the monitoring appliance reaches an internet access point. While the wearable appliance is outside of the mesh network range, the device searches for a cell phone with an expansion card plugged into a cell phone expansion slot such as the SDIO slot. If the wearable appliance detects a cell phone that is mesh network compatible, the wearable appliance communicates with the cell phone and provides information to the server 200 using the cellular connection. In one embodiment, a Zigbee SDIO card from C-guys, Inc., enables device-to-device communications for PDAs and smart phones. C-guys' ZigBee SDIO card includes the company's CG-100 SDIO application interface controller, which is designed to convert an application signal to an SD signal (or vice versa). The ZigBee card can provide signal ranges of up to 10 m in the 2.4 GHz band and data rates of up to 200 kbps. The card has peer-to-peer communications mode and supports direct application to PDAs or any SD supported hand-held cell phones. In this embodiment, the PDA or cell phone can provide a GPS position information instead of the indoor position information generated by the mesh network appliances 8. The cell phone GPS position information, accelerometer information and vital information such as heart rate information is transmitted using the cellular channel to the server 200 for processing as is normal. In another embodiment where the phone works through WiFi (802.11) or WiMAX (802.16) or ultra-wideband protocol instead of the cellular protocol, the wearable appliance can communicate over these protocols using a suitable mesh network interface to the phone. In instances where the wearable appliance is outside of its home base and a dangerous condition such as a fall is detected, the wearable appliance can initiate a distress call to the authorized third party using cellular, WiFi, WiMAX, or UWB protocols as is available.

Figure 6A:
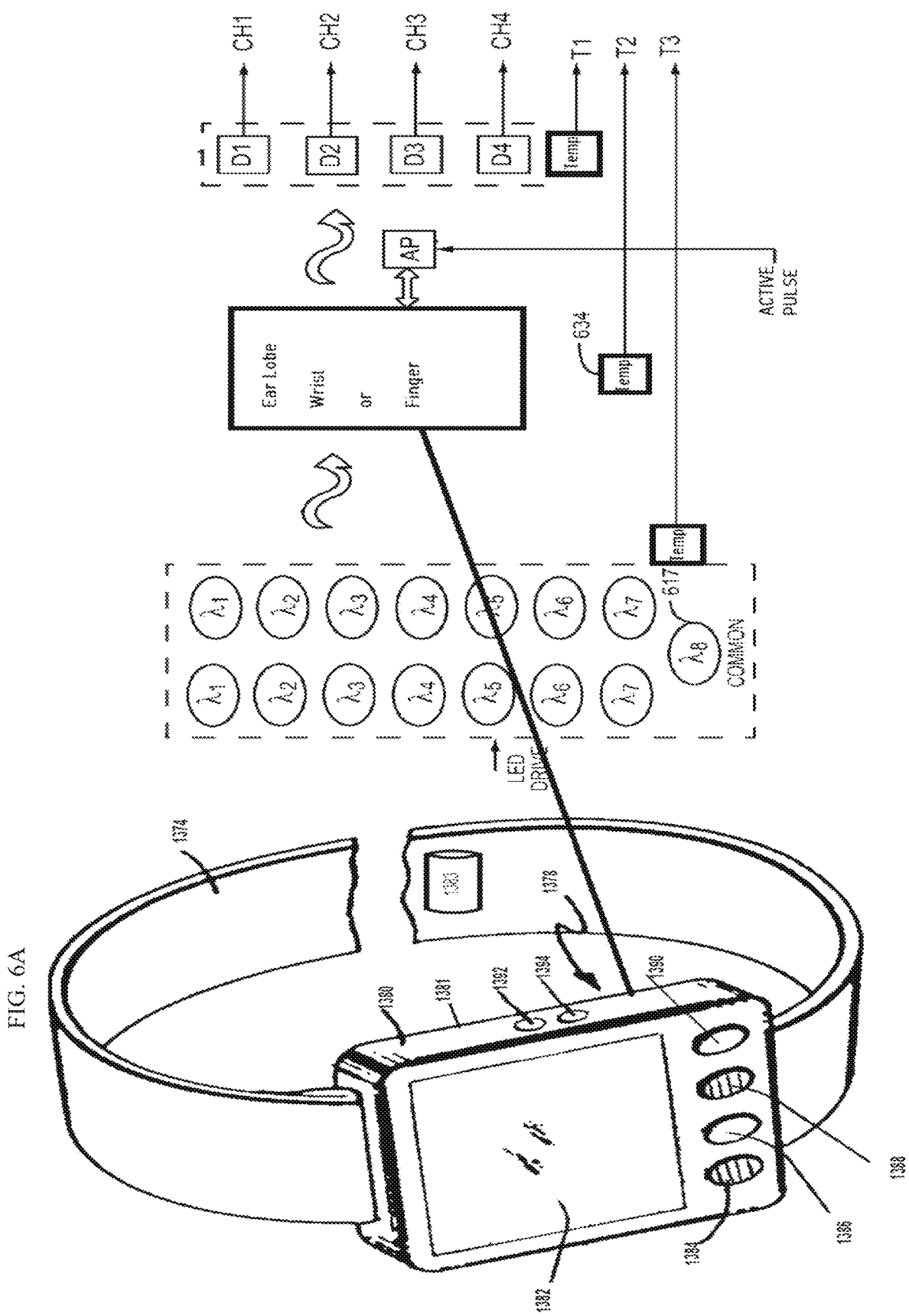

FIG. 6A shows a portable embodiment of the present invention where the voice recognizer is housed in a wristwatch. As shown in FIG. 6A, the device includes a wristwatch sized case 1380 supported on a wrist band 1374. The case 1380 may be of a number of variations of shape but can be conveniently made a rectangular, approaching a box-like configuration. The wrist-band 1374 can be an expansion band or a wristwatch strap of plastic, leather or woven material. The processor or CPU of the wearable appliance is connected to a radio frequency (RF) transmitter/receiver (such as a Bluetooth device, a Zigbee device, a WiFi device, a WiMAX device, or an 802.X transceiver, among others.

In one embodiment, the back of the device is a conductive metal electrode 1381 that in conjunction with a second electrode 1383 mounted on the wrist band 1374, enables differential EKG or ECG to be measured. The electrical signal derived from the electrodes is typically 1 mV peak-peak. In one embodiment where only one electrode 1381 or 1383 is available, an amplification of about 1000 is necessary to render this signal usable for heart rate detection. In the embodiment with electrodes 1381 and 1383 available, a differential amplifier is used to take advantage of the identical common mode signals from the EKG contact points, the common mode noise is automatically cancelled out using a matched differential amplifier. The wrist band 1374 can also contain other electrical devices such as ultrasound transducer, optical transducer or electromagnetic sensors, among others. In one embodiment, the transducer is an ultrasonic transducer that generates and transmits an acoustic wave upon command from the CPU during one period and listens to the echo returns during a subsequent period. In use, the transmitted bursts of sonic energy are scattered by red blood cells flowing through the subject's radial artery, and a portion of the scattered energy is directed back toward the ultrasonic transducer 84. The time required for the return energy to reach the ultrasonic transducer varies according to the speed of sound in the tissue and according to the depth of the artery. Typical transit times are in the range of 6 to 7 microseconds. The ultrasonic transducer is used to receive the reflected ultrasound energy during the dead times between the successive transmitted bursts. The frequency of the ultrasonic transducer's transmit signal will differ from that of the return signal, because the scattering red blood cells within the radial artery are moving. Thus, the return signal, effectively, is frequency modulated by the blood flow velocity.

A driving and receiving circuit generates electrical pulses which, when applied to the transducer, produce acoustic energy having a frequency on the order of 8 MHz, a pulse width or duration of approximately 8 microseconds, and a pulse repetition interval (PRI) of approximately 16 μs, although other values of frequency, pulse width, and PRI may be used. In one embodiment, the transducer 84 emits an 8 microsecond pulse, which is followed by an 8 microsecond "listen" period, every 16 microseconds. The echoes from these pulses are received by the ultrasonic transducer 84 during the listen period. The ultrasonic transducer can be a ceramic piezoelectric device of the type well known in the art, although other types may be substituted.

An analog signal representative of the Doppler frequency of the echo is received by the transducer and converted to a digital representation by the ADC, and supplied to the CPU for signal processing. Within the CPU, the digitized Doppler frequency is scaled to compute the blood flow velocity within the artery based on the Doppler frequency. Based on the real time the blood flow velocity, the CPU applies the vital model to the corresponding blood flow velocity to produce the estimated blood pressure value.

Prior to operation, calibration is done using a calibration device and the monitoring device to simultaneously collect blood pressure values (systolic, diastolic pressures) and a corresponding blood flow velocity generated by the monitoring device. The calibration device is attached to the base station and measures systolic and diastolic blood pressure using a cuff-based blood pressure monitoring device that includes a motor-controlled pump and data-processing electronics. While the cuff-based blood pressure monitoring device collects patient data, the transducer collects patient data in parallel and through the watch's radio transmitter, blood flow velocity is sent to the base station for generating a computer model that converts the blood flow velocity information into systolic and diastolic blood pressure values and this information is sent wirelessly from the base station to the watch for display and to a remote server if needed. This process is repeated at a later time (e.g., 15 minutes later) to collect a second set of calibration parameters. In one embodiment, the computer model fits the blood flow velocity to the systolic/diastolic values. In another embodiment, the computer trains a neural network or HMM to recognize the systolic and diastolic blood pressure values.

After the computer model has been generated, the system is ready for real-time blood pressure monitoring. In an acoustic embodiment, the transducer directs ultrasound at the patient's artery and subsequently listens to the echos therefrom. The echoes are used to determine blood flow, which is fed to the computer model to generate the systolic and diastolic pressure values as well as heart rate value. The CPU's output signal is then converted to a form useful to the user such as a digital or analog display, computer data file, or audible indicator. The output signal can drive a speaker to enable an operator to hear a representation of the Doppler signals and thereby to determine when the transducer is located approximately over the radial artery. The output signal can also be wirelessly sent to a base station for subsequent analysis by a physician, nurse, caregiver, or treating professional. The output signal can also be analyzed for medical attention and medical treatment.

It is noted that while the above embodiment utilizes a preselected pulse duration of 8 microseconds and pulse repetition interval of 16 microseconds, other acoustic sampling techniques may be used in conjunction with the invention. For example, in a second embodiment of the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 84) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to be equivalent.

In one optical embodiment, the transducer can be an optical transducer. The optical transducer can be a light source and a photo-detector embedded in the wrist band portions 1374. The light source can be light-emitting diodes that generate red ($\lambda\sim 630$ nm) and infrared ($\lambda\sim 900$ nm) radiation, for example. The light source and the photo-detector are slidably adjustable and can be moved along the wrist band to optimize beam transmission and pick up. As the heart pumps blood through the patient's finger, blood cells absorb and transmit varying amounts of the red and infrared radiation depending on how much oxygen binds to the cells' hemoglobin. The photo-detector detects transmission at the predetermined wavelengths, for example red and infrared wavelengths, and provides the detected transmission to a pulse-oximetry circuit embedded within the wristwatch. The output of the pulse-oximetry circuit is digitized into a time-dependent optical waveform, which is then sent back to the pulse-oximetry circuit and analyzed to determine the user's vital signs.

In the electromagnetic sensor embodiment, the wrist band 1374 is a flexible plastic material incorporated with a flexible magnet. The magnet provides a magnetic field, and one or more electrodes similar to electrode 1383 are positioned on the wrist band to measure voltage drops which are proportional to the blood velocity. The electromagnetic embodiment may be mounted on the upper arm of the patient, on the ankle or on the neck where peripheral blood vessels pass through and their blood velocity may be measured with minimal interruptions. The flexible magnet produces a pseudo-uniform (non-gradient) magnetic field. The magnetic field can be normal to the blood flow direction when wrist band 1374 is mounted on the user's wrist or may be a rotative pseudo-uniform magnetic field so that the magnetic field is in a transversal direction in respect to the blood flow direction. The electrode output signals are processed to obtain a differential measurement enhancing the signal to noise ratio. The flow information is derived based on the periodicity of the signals. The decoded signal is filtered over several periods and then analyzed for changes used to estimate artery and vein blood flow. Systemic stroke volume and cardiac output may be calculated from the peripheral SV index value.

The wrist-band 1374 further contains an antenna 1376 for transmitting or receiving radio frequency signals. The wrist-band 1374 and the antenna 1376 inside the band are mechanically coupled to the top and bottom sides of the wrist-watch housing 1380. Further, the antenna 1376 is electrically coupled to a radio frequency transmitter and receiver for wireless communications with another computer or another user. Although a wrist-band is disclosed, a number of substitutes may be used, including a belt, a ring holder, a brace, or a bracelet, among other suitable substitutes known to one skilled in the art. The housing 1380 contains the processor and associated peripherals to provide the human-machine interface. A display 1382 is located on the front section of the housing 1380. A speaker 1384, a microphone 1388, and a plurality of push-button switches 1386 and 1390 are also located on the front section of housing 1380.

The electronic circuitry housed in the watch case 1380 detects adverse conditions such as falls or seizures. In one implementation, the circuitry can recognize speech, namely utterances of spoken words by the user, and converting the utterances into digital signals. The circuitry for detecting and processing speech to be sent from the wristwatch to the base station 20 over the mesh network includes a central processing unit (CPU) connected to a ROM/RAM memory via a bus. In one embodiment, speech recognition such as a speech recognizer is discussed in U.S. Pat. No. 6,070,140 by the inventor of the instant invention, the content of which is incorporated by reference. Energy harvesters can be based on piezoelectric devices, solar cells or electromagnetic devices that convert mechanical vibrations as detailed in U.S. Pat. No. 9,820,658 to Tran, the content of which is incorporated by reference.

Figure 6B:
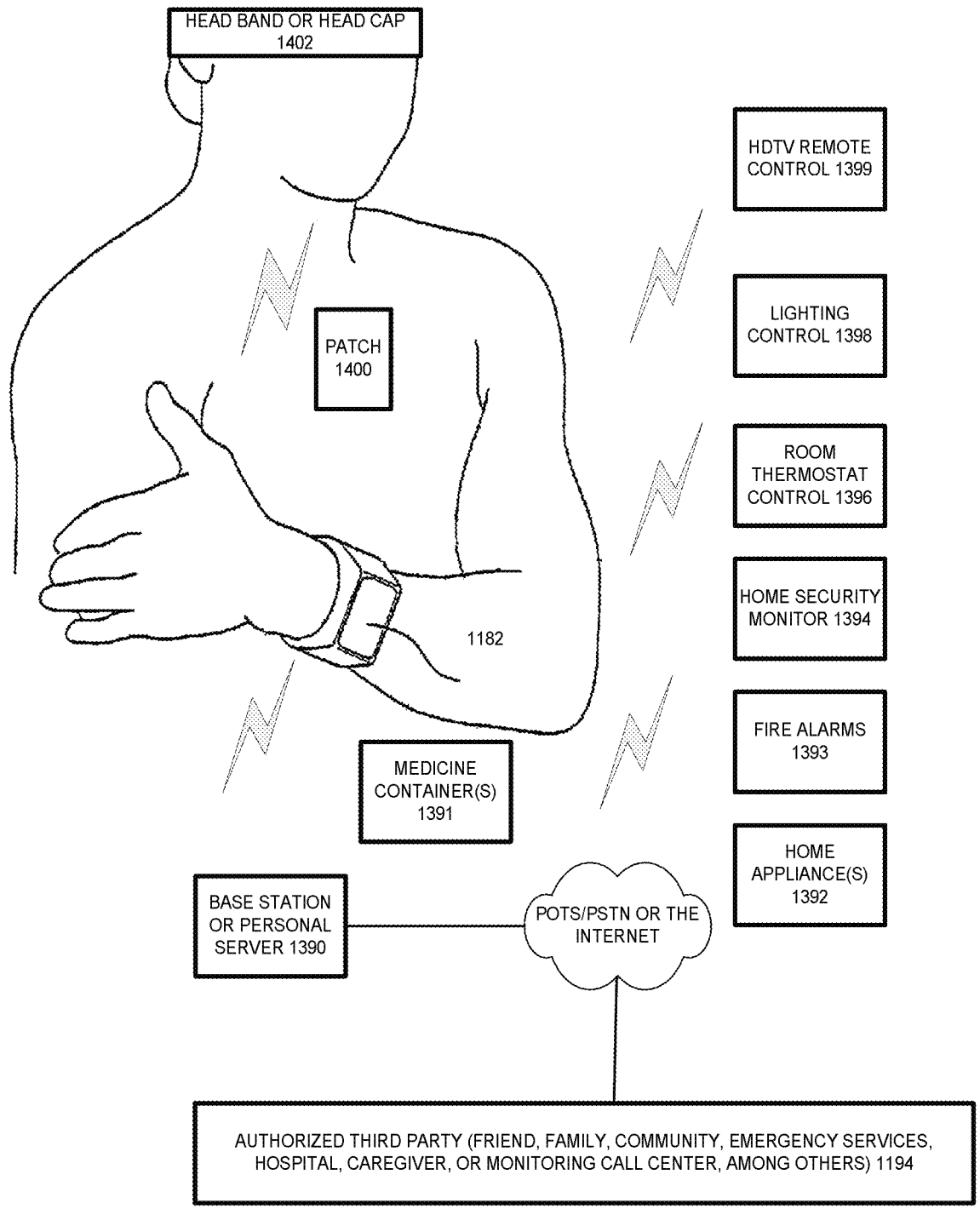
FIG. 6B shows the watch operating in a house or hospital in conjunction with other appliances.

FIG. 6B shows an exemplary mesh network working with the wearable appliance of FIG. 6A. Data collected and communicated on the display 1382 of the watch as well as voice is transmitted to a base station 1390 for communicating over a network to an authorized party 1394. The watch and the base station is part of a mesh network that may communicate with a medicine cabinet to detect opening or to each medicine container 1391 to detect medication compliance. Other devices include mesh network thermometers, scales, or exercise devices. The mesh network also includes a plurality of home/room appliances 1392-1399. The ability to transmit voice is useful in the case the patient has fallen down and cannot walk to the base station 1390 to request help. Hence, in one embodiment, the watch captures voice from the user and transmits the voice over the Zigbee mesh network to the base station 1390. The base station 1390 in turn dials out to an authorized third party to allow voice communication and at the same time transmits the collected patient vital parameter data and identifying information so that help can be dispatched quickly, efficiently and error-free. In one embodiment, the base station 1390 is a POTS telephone base station connected to the wired phone network. In a second embodiment, the base station 1390 can be a cellular telephone connected to a cellular network for voice and data transmission. In a third embodiment, the base station 1390 can be a WiMAX or 802.16 standard base station that can communicate VOIP and data over a wide area network. I one implementation, Zigbee or 802.15 appliances communicate locally and then transmits to the wide area network (WAN) such as the Internet over WiFi or WiMAX. Alternatively, the base station can communicate with the WAN over POTS and a wireless network such as cellular or WiMAX or both.

One embodiment of FIG. 6B includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist watch or wrist band are used to apply AC or DC constant current into the body or body segment. The voltage signal from the surface of the body is measured in terms of impedance using the same or an additional two electrodes on the watch or wrist band. In a bipolar implementation, one electrode on the wrist watch or wrist band is used to apply AC or DC constant current into the body or body segment. The voltage signal from the surface of the body is measured in terms of impedance using the same or an alternative electrode on the watch or wrist band. The system of FIG. 6B may include a BI patch 1400 that wirelessly communicates BI information with the wrist watch. Other patches 1400 can be used to collect other medical information or vital parameter and communicate with the wrist watch or base station or the information could be relayed through each wireless node or appliance to reach a destination appliance such as the base station, for example. The system of FIG. 6B can also include a head-cap 1402 that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes (I1, I2) is used as current electrodes to introduce a low intensity constant current at high frequency into the body. A pair of electrodes (E1, E2) measures changes accompanying physiological events. Voltage measured across E1-E2 is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodes in these embodiments can be the same, adjacent to one another, or at significantly different locations. The electrode(s) can apply current levels from 20 uA to 10 mA rms at a frequency range of 20-100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower—body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyperhydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor include detecting and/or monitoring hypovolemia, hemorrhage or blood loss. The impedance measurements can be made sequentially over a period of in time; and the system can determine whether the subject is externally or internally bleeding based on a change in measured impedance. The watch can also report temperature, heat flux, vasodilation and blood pressure along with the BI information.

In one embodiment, in addition to monitoring glucose level using high frequency/low frequency signals as detailed above, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity p of blood and the length L of the chest, the impedance change $\Delta Z$ and base impedance (Zo) to the volume change $\Delta V$ of the tissue under measurement can be determined. The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

Once SV has been determined, CO can be determined according to the following expression:

CO=SV*HR, where HR=heart rate

CO can be determined for every heart-beat. Thus, the system can determine SV and CO on a beat-to-beat basis, in addition to glucose levels.

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetrapolar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurement procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 911 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Po2 (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near 40% of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

Additional sensors such as thermocouples or thermistors and/or heat flux sensors can also be provided to provide measured values useful in analysis. In general, skin surface temperature will change with changes in blood flow in the vicinity of the skin surface of an organism. Such changes in blood flow can occur for a number of reasons, including thermal regulation, conservation of blood volume, and hormonal changes. In one implementation, skin surface measurements of temperature or heat flux are made in conjunction with hydration monitoring so that such changes in blood flow can be detected and appropriately treated.

In one embodiment, the patch includes a sound transducer such as a microphone or a piezoelectric transducer to pick up sound produced by bones or joints during movement. If bone surfaces are rough and poorly lubricated, as in an arthritic knee, they will move unevenly against each other, producing a high-frequency, scratching sound. The high-frequency sound from joints is picked up by wide-band acoustic sensor(s) or microphone(s) on a patient's body such as the knee. As the patient flexes and extends their knee, the sensors measure the sound frequency emitted by the knee and correlate the sound to monitor osteoarthritis, for example.

In another embodiment, the patch includes a Galvanic Skin Response (GSR) sensor. In this sensor, a small current is passed through one of the electrodes into the user's body such as the fingers and the CPU calculates how long it takes for a capacitor to fill up. The length of time the capacitor takes to fill up allows us to calculate the skin resistance: a short time means low resistance while a long time means high resistance. The GSR reflects sweat gland activity and changes in the sympathetic nervous system and measurement variables. Measured from the palm or fingertips, there are changes in the relative conductance of a small electrical current between the electrodes. The activity of the sweat glands in response to sympathetic nervous stimulation (Increased sympathetic activation) results in an increase in the level of conductance. Fear, anger, startle response, orienting response and sexual feelings are all among the emotions which may produce similar GSR responses.

In yet another embodiment, measurement of lung function such as peak expiratory flow readings is done though a sensor such as Wright's peak flow meter. In another embodiment, a respiratory estimator is provided that avoids the inconvenience of having the patient breathing through the flow sensor. In the respiratory estimator embodiment, heart period data from EKG/ECG is used to extract respiratory detection features. The heart period data is transformed into time-frequency distribution by applying a time-frequency transformation such as short-term Fourier transformation (STFT). Other possible methods are, for example, complex demodulation and wavelet transformation. Next, one or more respiratory detection features may be determined by setting up amplitude modulation of time-frequency plane, among others. The respiratory recognizer first generates a math model that correlates the respiratory detection features with the actual flow readings. The math model can be adaptive based on pre-determined data and on the combination of different features to provide a single estimate of the respiration. The estimator can be based on different mathematical functions, such as a curve fitting approach with linear or polynomial equations, and other types of neural network implementations, non-linear models, fuzzy systems, time series models, and other types of multivariate models capable of transferring and combining the information from several inputs into one estimate. Once the math model has been generated, the respirator estimator provides a real-time flow estimate by receiving EKG/ECG information and applying the information to the math model to compute the respiratory rate. Next, the computation of ventilation uses information on the tidal volume. An estimate of the tidal volume may be derived by utilizing different forms of information on the basis of the heart period signal. For example, the functional organization of the respiratory system has an impact in both respiratory period and tidal volume. Therefore, given the known relationships between the respiratory period and tidal volume during and transitions to different states, the information inherent in the heart period derived respiratory frequency may be used in providing values of tidal volume. In specific, the tidal volume contains inherent dynamics which may be, after modeling, applied to capture more closely the behavioral dynamics of the tidal volume. Moreover, it appears that the heart period signal, itself, is closely associated with tidal volume and may be therefore used to increase the reliability of deriving information on tidal volume. The accuracy of the tidal volume estimation may be further enhanced by using information on the subjects vital capacity (i.e., the maximal quantity of air that can be contained in the lungs during one breath). The information on vital capacity, as based on physiological measurement or on estimates derived from body measures such as height and weight, may be helpful in estimating tidal volume, since it is likely to reduce the effects of individual differences on the estimated tidal volume. Using information on the vital capacity, the mathematical model may first give values on the percentage of lung capacity in use, which may be then transformed to liters per breath. The optimizing of tidal volume estimation can based on, for example, least squares or other type of fit between the features and actual tidal volume. The minute ventilation may be derived by multiplying respiratory rate (breaths/min) with tidal volume (liters/breath).

In another embodiment, inductive plethysmography can be used to measure a cross-sectional area of the body by determining the self-inductance of a flexible conductor closely encircling the area to be measured. Since the inductance of a substantially planar conductive loop is well known to vary as, inter alia, the cross-sectional area of the loop, a inductance measurement may be converted into a plethysmographic area determination. Varying loop inductance may be measured by techniques known in the art, such as, e.g., by connecting the loop as the inductance in a variable frequency LC oscillator, the frequency of the oscillator then varying with the cross-sectional area of the loop inductance varies. Oscillator frequency is converted into a digital value, which is then further processed to yield the physiological parameters of interest. Specifically, a flexible conductor measuring a cross-sectional area of the body is closely looped around the area of the body so that the inductance, and the changes in inductance, being measured results from magnetic flux through the cross-sectional area being measured. The inductance thus depends directly on the cross-sectional area being measured, and not indirectly on an area which changes as a result of the factors changing the measured cross-sectional area. Various physiological parameters of medical and research interest may be extracted from repetitive measurements of the areas of various cross-sections of the body. For example, pulmonary function parameters, such as respiration volumes and rates and apneas and their types, may be determined from measurements of, at least, a chest transverse cross-sectional area and also an abdominal transverse cross-sectional area. Cardiac parameters, such central venous pressure, left and right ventricular volumes waveforms, and aortic and carotid artery pressure waveforms, may be extracted from repetitive measurements of transverse cross-sectional areas of the neck and of the chest passing through the heart. Timing measurements can be obtained from concurrent ECG measurements, and less preferably from the carotid pulse signal present in the neck. From the cardiac-related signals, indications of ischemia may be obtained independently of any ECG changes. Ventricular wall ischemia is known to result in paradoxical wall motion during ventricular contraction (the ischemic segment paradoxically "balloons" outward instead of normally contracting inward). Such paradoxical wall motion, and thus indications of cardiac ischemia, may be extracted from chest transverse cross-section area measurements. Left or right ventricular ischemia may be distinguished where paradoxical motion is seen predominantly in left or right ventricular waveforms, respectively. For another example, observations of the onset of contraction in the left and right ventricles separately may be of use in providing feedback to bi-ventricular cardiac pacing devices. For a further example, pulse oximetry determines hemoglobin saturation by measuring the changing infrared optical properties of a finger. This signal may be disambiguated and combined with pulmonary data to yield improved information concerning lung function.

In one embodiment to monitor and predict stroke attack, a cranial bioimpedance sensor is applied to detect fluids in the brain. The brain tissue can be modeled as an electrical circuit where cells with the lipid bilayer act as capacitors and the intra and extra cellular fluids act as resistors. The opposition to the flow of the electrical current through the cellular fluids is resistance. The system takes 50-kHz single-frequency bioimpedance measurements reflecting the electrical conductivity of brain tissue. The opposition to the flow of the current by the capacitance of lipid bilayer is reactance. In this embodiment, microamps of current at 50 kHz are applied to the electrode system. In one implementation, the electrode system consists of a pair of coaxial electrodes each of which has a current electrode and a voltage sensing electrode. For the measurement of cerebral bioimpedance, one pair of gel current electrodes is placed on closed eyelids and the second pair of voltage electrodes is placed in the suboccipital region projecting towards the foramen magnum. The electrical current passes through the orbital fissures and brain tissue. The drop in voltage is detected by the suboccipital electrodes and then calculated by the processor to bioimpedance values. The bioimpedance value is used to detect brain edema, which is defined as an increase in the water content of cerebral tissue which then leads to an increase in overall brain mass. Two types of brain edema are vasogenic or cytotoxic. Vasogenic edema is a result of increased capillary permeability. Cytotoxic edema reflects the increase of brain water due to an osmotic imbalance between plasma and the brain extracellular fluid. Cerebral edema in brain swelling contributes to the increase in intracranial pressure and an early detection leads to timely stroke intervention.

In another example, a cranial bioimpedance tomography system contructs brain impedance maps from surface measurements using nonlinear optimization. A nonlinear optimization technique utilizing known and stored constraint values permits reconstruction of a wide range of conductivity values in the tissue. In the nonlinear system, a Jacobian Matrix is renewed for a plurality of iterations. The Jacobian Matrix describes changes in surface voltage that result from changes in conductivity. The Jacobian Matrix stores information relating to the pattern and position of measuring electrodes, and the geometry and conductivity distributions of measurements resulting in a normal case and in an abnormal case. The nonlinear estimation determines the maximum voltage difference in the normal and abnormal cases.

In one embodiment, an electrode array sensor can include impedance, bio-potential, or electromagnetic field tomography imaging of cranial tissue. The electrode array sensor can be a geometric array of discrete electrodes having an equally-spaced geometry of multiple nodes that are capable of functioning as sense and reference electrodes. In a typical tomography application the electrodes are equally-spaced in a circular configuration. Alternatively, the electrodes can have non-equal spacing and/or can be in rectangular or other configurations in one circuit or multiple circuits. Electrodes can be configured in concentric layers too. Points of extension form multiple nodes that are capable of functioning as an electrical reference. Data from the multiple reference points can be collected to generate a spectrographic composite for monitoring over time.

The patient's brain cell generates an electromagnetic field of positive or negative polarity, typically in the millivolt range. The sensor measures the electromagnetic field by detecting the difference in potential between one or more test electrodes and a reference electrode. The bio-potential sensor uses signal conditioners or processors to condition the potential signal. In one example, the test electrode and reference electrode are coupled to a signal conditioner/processor that includes a lowpass filter to remove undesired high frequency signal components. The electromagnetic field signal is typically a slowly varying DC voltage signal. The lowpass filter removes undesired alternating current components arising from static discharge, electromagnetic interference, and other sources.

In one embodiment, the impedance sensor has an electrode structure with annular concentric circles including a central electrode, an intermediate electrode and an outer electrode, all of which are connected to the skin. One electrode is a common electrode and supplies a low frequency signal between this common electrode and another of the three electrodes. An amplifier converts the resulting current into a voltage between the common electrode and another of the three electrodes. A switch switches between a first circuit using the intermediate electrode as the common electrode and a second circuit that uses the outer electrode as a common electrode. The sensor selects depth by controlling the extension of the electric field in the vicinity of the measuring electrodes using the control electrode between the measuring electrodes. The control electrode is actively driven with the same frequency as the measuring electrodes to a signal level taken from one of the measuring electrodes but multiplied by a complex number with real and imaginary parts controlled to attain a desired depth penetration. The controlling field functions in the manner of a field effect transistor in which ionic and polarization effects act upon tissue in the manner of a semiconductor material.

With multiple groups of electrodes and a capability to measure at a plurality of depths, the system can perform tomographic imaging or measurement, and/or object recognition. In one embodiment, a fast reconstruction technique is used to reduce computation load by utilizing prior information of normal and abnormal tissue conductivity characteristics to estimate tissue condition without requiring full computation of a non-linear inverse solution.

In another embodiment, the bioimpedance system can be used with electro-encephalograph (EEG) or ERP. Since this embodiment collects signals related to blood flow in the brain, collection can be concentrated in those regions of the brain surface corresponding to blood vessels of interest. A headcap with additional electrodes placed in proximity to regions of the brain surface fed by a blood vessel of interest, such as the medial cerebral artery enables targeted information from the regions of interest to be collected. The headcap can cover the region of the brain surface that is fed by the medial cerebral artery. Other embodiments of the headcap can concentrate electrodes on other regions of the brain surface, such as the region associated with the somatosensory motor cortex. In alternative embodiments, the headcap can cover the skull more completely. Further, such a headcap can include electrodes throughout the cap while concentrating electrodes in a region of interest. Depending upon the particular application, arrays of 1-16 head electrodes may be used, as compared to the International 10/20 system of 19-21 head electrodes generally used in an EEG instrument.

In one implementation, each amplifier for each EEG channel is a high quality analog amplifier device. Full bandwidth and ultra-low noise amplification are obtained for each electrode. Low pass, high pass, hum notch filters, gain, un-block, calibration and electrode impedance check facilities are included in each amplifier. All 8 channels in one EEG amplifier unit have the same filter, gain, etc. settings. Noise figures of less than 0.1 uV r.m.s. are achieved at the input and optical coupling stages. These figures, coupled with good isolation/common mode rejection result in signal clarity. Nine high pass filter ranges include 0.01 Hz for readiness potential measurement, and 30 Hz for EMG measurement.

In one embodiment, stimulations to elicit EEG signals are used in two different modes, i.e., auditory clicks and electric pulses to the skin. The stimuli, although concurrent, are at different prime number frequencies to permit separation of different evoked potentials (EPs) and avoid interference. Such concurrent stimulations for EP permit a more rapid, and less costly, examination and provide the patient's responses more quickly. Power spectra of spontaneous EEG, waveshapes of Averaged Evoked Potentials, and extracted measures, such as frequency specific power ratios, can be transmitted to a remote receiver. The latencies of successive EP peaks of the patient may be compared to those of a normal group by use of a normative template. To test for ischemic stroke or intracerebral or subarachnoid hemorrhage, the system provides a blood oxygen saturation monitor, using an infra-red or laser source, to alert the user if the patient's blood in the brain or some brain region is deoxygenated.

The cranial bioimpedance sensor can be applied singly or in combination with a cranial blood flow sensor, which can be optical, ultrasound, electromagnetic sensor(s) as described in more details below. In an ultrasound imaging implementation, the carotid artery is checked for plaque build-up. Atherosclerosis is systemic—meaning that if the carotid artery has plaque buildup, other important arteries, such as coronary and leg arteries, might also be atherosclerotic.

In another embodiment, an epicardial array monopolar ECG system converts signals into the multichannel spectrum domain and identifies decision variables from the autospectra. The system detects and localizes the epicardial projections of ischemic myocardial ECGs during the cardiac activation phase. This is done by transforming ECG signals from an epicardial or torso sensor array into the multichannel spectral domain and identifying any one or more of a plurality of decision variables. The ECG array data can be used to detect, localize and quantify reversible myocardial ischemia.

In yet another embodiment, a trans-cranial Doppler velocimetry sensor provides a non-invasive technique for measuring blood flow in the brain. An ultrasound beam from a transducer is directed through one of three natural acoustical windows in the skull to produce a waveform of blood flow in the arteries using Doppler sonography. The data collected to determine the blood flow may include values such as the pulse cycle, blood flow velocity, end diastolic velocity, peak systolic velocity, mean flow velocity, total volume of cerebral blood flow, flow acceleration, the mean blood pressure in an artery, and the pulsatility index, or impedance to flow through a vessel. From this data, the condition of an artery may be derived, those conditions including stenosis, vasoconstriction, irreversible stenosis, vasodilation, compensatory vasodilation, hyperemic vasodilation, vascular failure, compliance, breakthrough, and pseudo-normalization.

In addition to the above techniques to detect stroke attack or out of control glucose level, the system can detect numbness or weakness of the face, arm or leg, especially on one side of the body. The system detects sudden confusion, trouble speaking or understanding, sudden trouble seeing in one or both eyes, sudden trouble walking, dizziness, loss of balance or coordination, or sudden, severe headache with no known cause.

In one embodiment to detect heart attack, the system detects discomfort in the center of the chest that lasts more than a few minutes, or that goes away and comes back. Symptoms can include pain or discomfort in one or both arms, the back, neck, jaw or stomach. The system can also monitor for shortness of breath which may occur with or without chest discomfort. Other signs may include breaking out in a cold sweat, nausea or lightheadedness.

In order to best analyze a patient's risk of stroke attack or out of control glucose level, additional patient data is utilized by a risk analyzer. This data may include personal data, such as date of birth, ethnic group, sex, physical activity level, and address. The data may further include clinical data such as a visit identification, height, weight, date of visit, age, blood pressure, pulse rate, respiration rate, and so forth. The data may further include data collected from blood work, such as the antinuclear antibody panel, B-vitamin deficiency, C-reactive protein value, calcium level, cholesterol levels, entidal $CO_2$, fibromogin, amount of folic acid, glucose level, hematocrit percentage, H-pylori antibodies, hemocysteine level, hypercapnia, magnesium level, methyl maloric acid level, platelets count, potassium level, sedrate (ESR), serum osmolality, sodium level, zinc level, and so forth. The data may further include the health history data of the patient, including alcohol intake, autoimmune diseases, caffeine intake, carbohydrate intake, carotid artery disease, coronary disease, diabetes, drug abuse, fainting, glaucoma, head injury, hypertension, lupus, medications, smoking, stroke, diabetes, family history of stroke/diabetes, surgery history, for example.

In one embodiment, data driven analyzers may be used to track the patient's risk of stroke or heart attack or out of control glucose level. These data driven analyzers may incorporate a number of models such as parametric statistical models, non-parametric statistical models, clustering models, nearest neighbor models, regression methods, and engineered (artificial) neural networks. Prior to operation, data driven analyzers or models of the patient stoke patterns are built using one or more training sessions. The data used to build the analyzer or model in these sessions are typically referred to as training data. As data driven analyzers are developed by examining only training examples, the selection of the training data can significantly affect the accuracy and the learning speed of the data driven analyzer. One approach used heretofore generates a separate data set referred to as a test set for training purposes. The test set is used to avoid overfitting the model or analyzer to the training data. Overfitting refers to the situation where the analyzer has memorized the training data so well that it fails to fit or categorize unseen data. Typically, during the construction of the analyzer or model, the analyzer's performance is tested against the test set. The selection of the analyzer or model parameters is performed iteratively until the performance of the analyzer in classifying the test set reaches an optimal point. At this point, the training process is completed. An alternative to using an independent training and test set is to use a methodology called cross-validation. Cross-validation can be used to determine parameter values for a parametric analyzer or model for a non-parametric analyzer. In cross-validation, a single training data set is selected. Next, a number of different analyzers or models are built by presenting different parts of the training data as test sets to the analyzers in an iterative process. The parameter or model structure is then determined on the basis of the combined performance of all models or analyzers. Under the cross-validation approach, the analyzer or model is typically retrained with data using the determined optimal model structure.

In general, multiple dimensions of a user's EEG, EKG, BI, ultrasound, optical, acoustic, electromagnetic, or electrical parameters are encoded as distinct dimensions in a database. A predictive model, including time series models such as those employing autoregression analysis and other standard time series methods, dynamic Bayesian networks and Continuous Time Bayesian Networks, or temporal Bayesian-network representation and reasoning methodology, is built, and then the model, in conjunction with a specific query makes target inferences. Bayesian networks provide not only a graphical, easily interpretable alternative language for expressing background knowledge, but they also provide an inference mechanism; that is, the probability of arbitrary events can be calculated from the model. Intuitively, given a Bayesian network, the task of mining interesting unexpected patterns can be rephrased as discovering item sets in the data which are much more—or much less—frequent than the background knowledge suggests. These cases are provided to a learning and inference subsystem, which constructs a Bayesian network that is tailored for a target prediction. The Bayesian network is used to build a cumulative distribution over events of interest.

In another embodiment, a genetic algorithm (GA) search technique can be used to find approximate solutions to identifying the user's stroke risks or heart attack risks. Genetic algorithms are a particular class of evolutionary algorithms that use techniques inspired by evolutionary biology such as inheritance, mutation, natural selection, and recombination (or crossover). Genetic algorithms are typically implemented as a computer simulation in which a population of abstract representations (called chromosomes) of candidate solutions (called individuals) to an optimization problem evolves toward better solutions. Traditionally, solutions are represented in binary as strings of 0s and 1s, but different encodings are also possible. The evolution starts from a population of completely random individuals and happens in generations. In each generation, the fitness of the whole population is evaluated, multiple individuals are stochastically selected from the current population (based on their fitness), modified (mutated or recombined) to form a new population, which becomes current in the next iteration of the algorithm. Other types of learning system or process may be employed to determine the stroke or heart attack patterns so that unusual events can be flagged.

In one embodiment, clustering operations are performed to detect patterns in the data. In another embodiment, a neural network is used to recognize each pattern as the neural network is quite robust at recognizing user habits or patterns. Once the treatment features have been characterized, the neural network then compares the input user information with stored templates of treatment vocabulary known by the neural network recognizer, among others. The recognition models can include a Hidden Markov Model (HMM), a dynamic programming model, a neural network, a fuzzy logic, or a template matcher, among others. These models may be used singly or in combination, and such details are in the Tran U.S. Pat. No. 9,820,658.

The sensor can be used for drug delivery system, e.g. when patient has abdomen pain, soothing drug can be applied, based on the level of pain the sensor detects, different dose of drugs will be applied.

The array of sensors may allow the selection and analysis of zones of sensors in the areas of interest such as the abdomen area. Each sensor array has a low spatial resolution:
approximately 10 cm between each sensor. In addition to lower cost due to the low number of sensors, it is also possible to modify the data collection rate from certain sensors that are providing high-quality data. Other sensors may include those worn on the body, such as in watch bands, finger rings, or adhesive sensors, but telemetry, not wires, would be used to communicate with the controller.

The sensor can be passive device such as a reader, which mounted near the crib can active it from time to time. In any emergency situation, the sensor automatically signals a different state which the reader can detect.

The sensor can be active and powered by body motion or body heat. The sensor can detect low battery situation and warn the user to provide a replacement battery.

In one embodiment, a plurality of sensors attached to the infant collects the vital parameters. For example, the sensors can be attached to the infant's clothing (shirt or pant), diaper, undergarment or bed sheet, bed linen, or bed spread.

The patient may wear one or more sensors, for example devices for sensing EMG, EKG, blood pressure, sugar level, weight, temperature and pressure, among others. In one embodiment, an optical temperature sensor can be used. In another embodiment, a temperature thermistor can be used to sense patient temperature. In another embodiment, a fat scale sensor can be used to detect the patient's fat content. In yet another embodiment, a pressure sensor such as a MEMS sensor can be used to sense pressure on the patient.

In one embodiment, the sensors are mounted on the patient's wrist (such as a wristwatch sensor) and other convenient anatomical locations. Exemplary sensors include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to the server 20 using wired or wireless transmission. Alternatively, all sensors can be fed through a common bus into a single transceiver for wired or wireless transmission. The transmission can be done using a magnetic medium such as a floppy disk or a flash memory card, or can be done using infrared or radio network link, among others.

In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

In an optical heartbeat detector embodiment, an optical transducer is positioned on a finger, wrist, or ear lobe. The ear, wrist or finger pulse oximeter waveform is then analyzed to extract the beat-to-beat amplitude, area, and width (half height) measurements. The oximeter waveform is used to generate heartbeat rate in this embodiment. In one implementation, a reflective sensor such as the Honeywell HLC1395 can be used. The device emits lights from a window in the infrared spectrum and receives reflected light in a second window. When the heart beats, blood flow increases temporarily and more red blood cells flow through the windows, which increases the light reflected back to the detector. The light can be reflected, refracted, scattered, and absorbed by one or more detectors. Suitable noise reduction is done, and the resulting optical waveform is captured by the CPU.

In another optical embodiment, blood pressure is estimated from the optical reading using a mathematical model such as a linear correlation with a known blood pressure reading. In this embodiment, the pulse oximeter readings are compared to the blood-pressure readings from a known working blood pressure measurement device during calibration. Using these measurements the linear equation is developed relating oximeter output waveform such as width to blood-pressure (systolic, mean and pulse pressure). In one embodiment, a transform (such as a Fourier analysis or a Wavelet transform) of the oximeter output can be used to generate a model to relate the oximeter output waveform to the blood pressure. Other non-linear math model or relationship can be determined to relate the oximeter waveform to the blood pressure.

In an ultrasonic embodiment, a piezo film sensor element is placed on the wristwatch band. The sensor can be the SDT1-028K made by Measurement Specialties, Inc. The sensor should have features such as: (a) it is sensitive to low level mechanical movements, (b) it has an electrostatic shield located on both sides of the element (to minimize 50/60 Hz AC line interference), (c) it is responsive to low frequency movements in the 0.7-12 Hz range of interest. A filter/amplifier circuit has a three-pole low pass filter with a lower (−3 dB) cutoff frequency at about 12-13 Hz. The low-pass filter prevents unwanted 50/60 Hz AC line interference from entering the sensor. However, the piezo film element has a wide band frequency response so the filter also attenuates any extraneous sound waves or vibrations that get into the piezo element. The DC gain is about +30 dB.

Waveform averaging can be used to reduce noise. It reinforces the waveform of interest by minimizing the effect of any random noise. These pulses were obtained when the arm was motionless. If the arm was moved while capturing the data the waveform did not look nearly as clean. That's because motion of the arm causes the sonic vibrations to enter the piezo film through the arm or by way of the cable. An accelerometer is used to detect arm movement and used to remove inappropriate data capture.

In one embodiment that can determine blood pressure, two piezo film sensors and filter/amplifier circuits can be configured as a non-invasive velocity type blood pressure monitor. One sensor can be on the wrist and the other can be located on the inner left elbow at the same location where Korotkoff sounds are monitored during traditional blood pressure measurements with a spygmometer. The correlation between pulse delay and blood pressure is well known in the art of non-invasive blood pressure monitors.

In yet another embodiment, an ultrasonic transducer generates and transmits an acoustic wave into the user's body such as the wrist or finger. The transducer subsequently receives pressure waves in the form of echoes resulting from the transmitted acoustic waves. In one embodiment, an ultrasonic driving and receiving circuit generates electrical pulses which, when applied to the transducer produce acoustic energy having a frequency on the order of 8 MHz, a pulse width or duration of approximately 8 microseconds, and a pulse repetition interval (PM) of approximately 16 microseconds, although other values of frequency, pulse width, and PM may be used. Hence, the transducer emits an 8 microsecond ultrasonic pulse, which is followed by an 8 microsecond "listen" period, every 16 microseconds. The echoes from these pulses are received by the ultrasonic transducer during the listen period. The ultrasonic transducer can be a ceramic piezoelectric device of the type well known in the art, although other types may be substituted. The transducer converts the received acoustic signal to an electrical signal, which is then supplied to the receiving section of the ultrasonic driver and receiver circuit 616, which contains two receiver circuits. The output of the first receiver circuit is an analog signal representative of the Doppler frequency of the echo received by the transducer which is digitized and supplied to the CPU. Within the CPU, the digitized Doppler frequency is scaled to compute the blood velocity within the artery based on the Doppler frequency. The time-frequency distribution of the blood velocity is then computed. Finally, the CPU maps in time the peak of the time-frequency distribution to the corresponding pressure waveform to produce the estimated mean arterial pressure (MAP). The output of the ultrasonic receiver circuit is an analog echo signal proportional to absorption of the transmitted frequencies by blood or tissue. This analog signal is digitized and process so that each group of echoes, generated for a different transversal position, is integrated to determine a mean value. The mean echo values are compared to determine the minimum value, which is caused by direct positioning over the artery. In one embodiment, the device includes an accelerometer or alternative motion-detecting device to determine when the patient' hand is at rest, thereby reducing motion-related artifacts introduced to the measurement.

In yet another ultrasonic embodiment, a transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the system includes a pair of piezoelectric crystals at an angle to each other, wherein the angle is determined by the depth of the object being monitored. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the user's wrist and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow. Ultrasonic energy is delivered to one of the two piezoelectric elements in the module by the power amplifier. The other element picks up the reflected ultrasonic signal as Doppler frequencies.

In a digital stethoscope embodiment, a microphone or a piezoelectric transducer is placed near the wrist artery to pick up heart rate information. In one embodiment, the microphone sensor and optionally the EKG sensor are place on the wrist band 1374 of the watch to analyze the acoustic signal or signals emanating from the cardiovascular system and, optionally can combine the sound with an electric signal (EKG) emanating from the cardiovascular system and/or an acoustic signal emanating from the respiratory system. The system can perform automated auscultation of the cardiovascular system, the respiratory system, or both. For example, the system can differentiate pathological from benign heart murmurs, detect cardiovascular diseases or conditions that might otherwise escape attention, recommend that the patient go through for a diagnostic study such as an echocardiography or to a specialist, monitor the course of a disease and the effects of therapy, decide when additional therapy or intervention is necessary, and providing a more objective basis for the decision(s) made. In one embodiment, the analysis includes selecting one or more beats for analysis, wherein each beat comprises an acoustic signal emanating from the cardiovascular system; performing a time-frequency analysis of beats selected for analysis so as to provide information regarding the distribution of energy, the relative distribution of energy, or both, over different frequency ranges at one or more points in the cardiac cycle; and processing the information to reach a clinically relevant conclusion or recommendation. In another implementation, the system selects one or more beats for analysis, wherein each beat comprises an acoustic signal emanating from the cardiovascular system; performs a time-frequency analysis of beats selected for analysis so as to provide information regarding the distribution of energy, the relative distribution of energy, or both, over different frequency ranges at one or more points in the cardiac cycle; and present information derived at least in part from the acoustic signal, wherein the information comprises one or more items selected from the group consisting of: a visual or audio presentation of a prototypical beat, a display of the time-frequency decomposition of one or more beats or prototypical beats, and a playback of the acoustic signal at a reduced rate with preservation of frequency content.

In an electromagnetic embodiment where the wrist band incorporates a flexible magnet to provide a magnetic field and one or more electrodes positioned on the wrist band to measure voltage drops which are proportional to the blood velocity, instantaneously variation of the flow can be detected but not artery flow by itself. To estimate the flow of blood in the artery, the user or an actuator such as motorized cuff temporarily stops the blood flow in the vein by applying external pressure or by any other method. During the period of time in which the vein flow is occluded, the decay of the artery flow is measured. This measurement may be used for zeroing the sensor and may be used in a model for estimating the steady artery flow. The decay in artery flow due to occlusion of veins is measured to arrive at a model the rate of artery decay. The system then estimates an average artery flow before occlusion. The blood flow can then be related to the blood pressure.

In another embodiment, an ionic flow sensor is used with a driving electrode that produces a pulsatile current. The pulsatile current causes a separation of positive and negative charges that flows in the blood of the arteries and veins passing in the wrist area. Using electrophoresis principle, the resistance of the volume surrounded by the source first decreases and then increases. The difference in resistance in the blood acts as a mark that moves according to the flow of blood so that marks are flowing in opposite directions by arteries and veins.

In the above embodiments, accelerometer information is used to detect that the patient is at rest prior to making a blood pressure measurement and estimation. Further, a temperature sensor may be incorporated so that the temperature is known at any minute. The processor correlates the temperature measurement to the blood flow measurement for calibration purposes.

In another embodiment, the automatic identification of the first, second, third and fourth heart sounds (S1, S2, S3, S4) is done. In yet another embodiment, based on the heart sound, the system analyzes the patient for mitral valve prolapse. The system performs a time-frequency analysis of an acoustic signal emanating from the subject's cardiovascular system and examines the energy content of the signal in one or more frequency bands, particularly higher frequency bands, in order to determine whether a subject suffers from mitral valve prolapse.

FIG. 7 shows an exemplary mesh network that includes the wrist-watch of FIG. 6 in communication with a mesh network including a telephone such as a wired telephone as well as a cordless telephone. In one embodiment, the mesh network is an IEEE 802.15.4 (ZigBee) network. One embodiment supports a multicluster-multihop network assembly to enable communication among every node in a distribution of nodes. The algorithm should ensure total connectivity, given a network distribution that will allow total connectivity. One such algorithm of an embodiment is described in U.S. Pat. No. 6,832,251, the content of which is incorporated by referenced. A mesh network appliance can be connected to a power line to communicate X10 data to and from the mesh network. X10 is a communication protocol that allows up to 256 X10 products to talk to each other using the existing electrical wiring in the home. Typically, the installation is simple, a transmitter plugs (or wires) in at one location in the home and sends its control signal (on, off, dim, bright, etc.) to a receiver which plugs (or wires) into another location in the home. The mesh network appliance translates messages intended for X10 device to be relayed over the ZigBee wireless network, and then transmitted over the power line using a ZigBee to X10 converter appliance.

Figure 8:
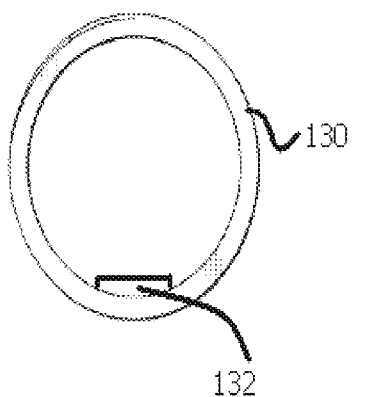
FIGS. 8-14 show various exemplary wearable appliances to monitor a patient.

Turning now to FIGS. 8-13, various exemplary monitoring devices are shown. In FIG. 8, a ring 130 has an opening 132 for transmitting and receiving acoustic energy to and from the sensor 84 in an acoustic implementation. In an optical implementation, a second opening (not shown) is provided to emit an optical signal from an LED, for example, and an optical detector can be located at the opening 132 to receive the optical signal passing through the finger wearing the ring 130. In another implementation, the ring has an electrically movable portion 134 and rigid portions 136-138 connected thereto. The electrically movable portion 134 can squeeze the finger as directed by the CPU during an applanation sweep to determine the arterial blood pressure.

Figure 9:
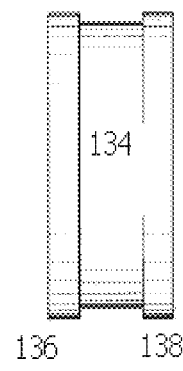

FIG. 9 shows an alternate finger cover embodiment where a finger-mounted module housing the photo-detector and light source. The finger mounted module can be used to measure information that is processed to determine the user's blood pressure by measuring blood flow in the user's finger and sending the information through a wireless connection to the base station. In one implementation, the housing is made from a flexible polymer material.

Figure 10:
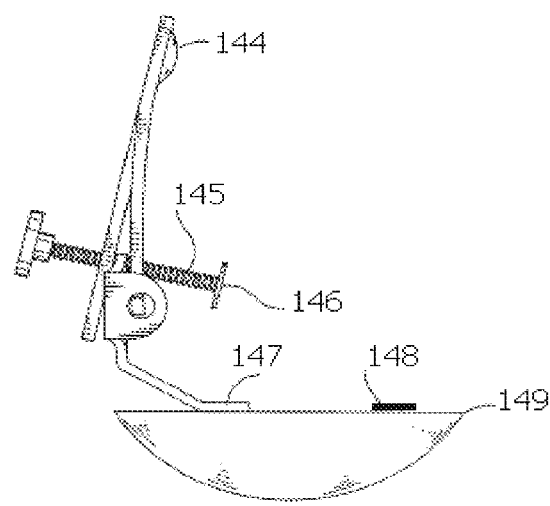

In an embodiment to be worn on the patient's ear lobe, the monitoring device can be part of an earring jewelry clipped to the ear lobe. In the implementation of FIG. 10, the monitoring device has a jewelry body 149 that contains the monitoring electronics and power source. The surface of the body 149 is an ornamental surface such as jade, ivory, pearl, silver, or gold, among others. The body 149 has an opening 148 that transmits energy such as optical or acoustic energy through the ear lobe to be detected by a sensor 144 mounted on a clamp portion that is secured to the body 149 at a base 147. The energy detected through the sensor 144 is communicated through an electrical connector to the electronics in the jewelry body 149 for processing the received energy and for performing wireless communication with a base station.

Figure 11:
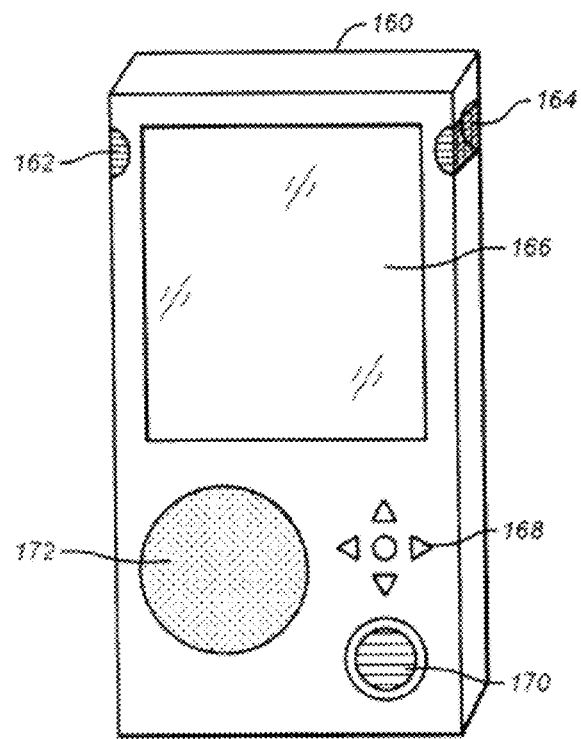

In FIG. 11, a monitoring device has a body 160 comprising microphone ports 162, 164 and 170 arranged in a first order noise cancelling microphone arrangement. The microphones 162 and 164 are configured to optimally receive distant noises, while the microphone 170 is optimized for capturing the user's speech. A touch sensitive display 166 and a plurality of keys 168 are provided to capture hand inputs. Further, a speaker 172 is provided to generate a verbal feedback to the user.

Figure 12:
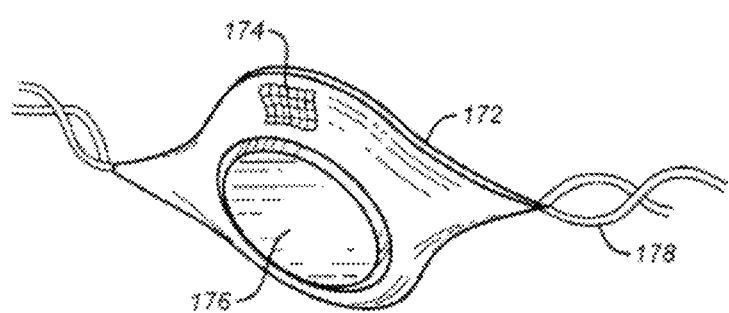

Turning now to FIG. 12, a jewelry-sized monitoring device is illustrated. In this embodiment, a body 172 houses a microphone port 174 and a speaker port 176. The body 172 is coupled to the user via the necklace 178 so as to provide a personal, highly accessible personal computer. Due to space limitations, voice input/output is an important user interface of the jewelry-sized computer. Although a necklace is disclosed, one skilled in the art can use a number of other substitutes such as a belt, a brace, a ring, or a band to secure the jewelry-sized computer to the user.

Figure 13:
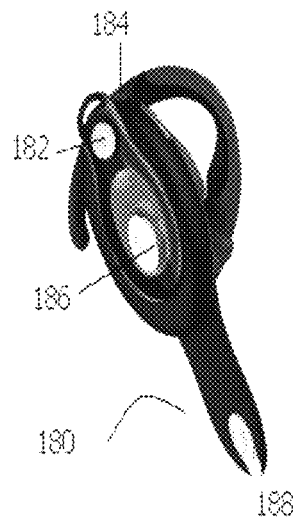

FIG. 13 shows an exemplary ear phone embodiment 180. The ear phone 180 has an optical transmitter 182 which emits LED wavelengths that are received by the optical receiver 184. The blood oximetry information is generated and used to determine blood pulse or blood pressure. Additionally, a module 186 contains mesh network communication electronics, accelerometer, and physiological sensors such as bioimpedance/ECG sensors or temperature sensors or ultrasonic sensors. The ear phone optionally has an ear canal temperature sensor for sensing temperature in a human.

Figure 14B:
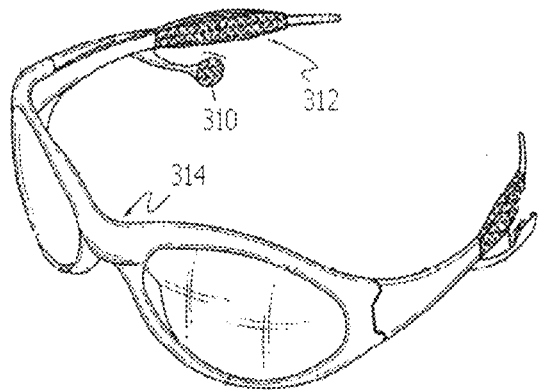
Figure 14A:
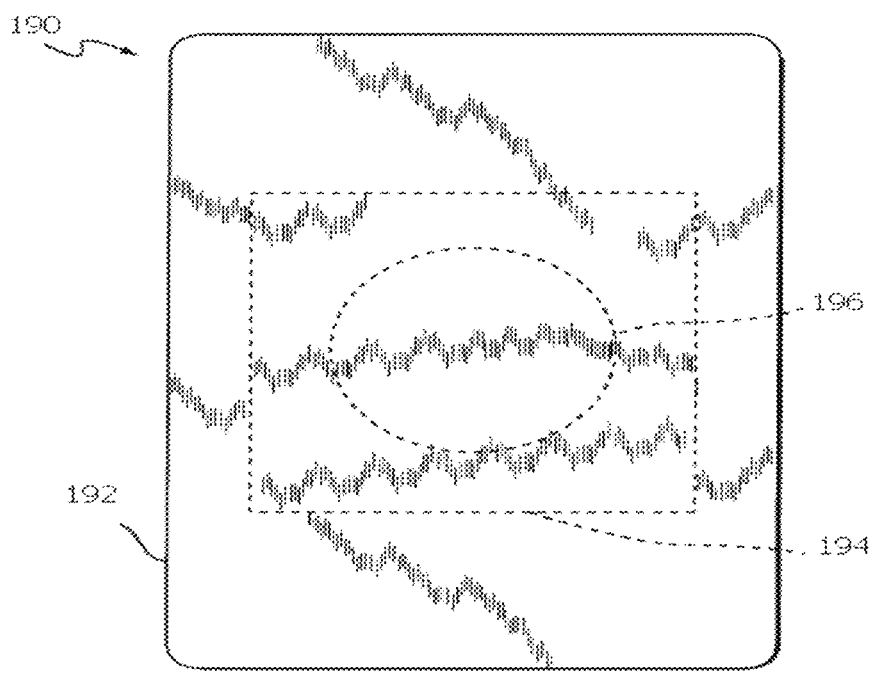
Figure 17:
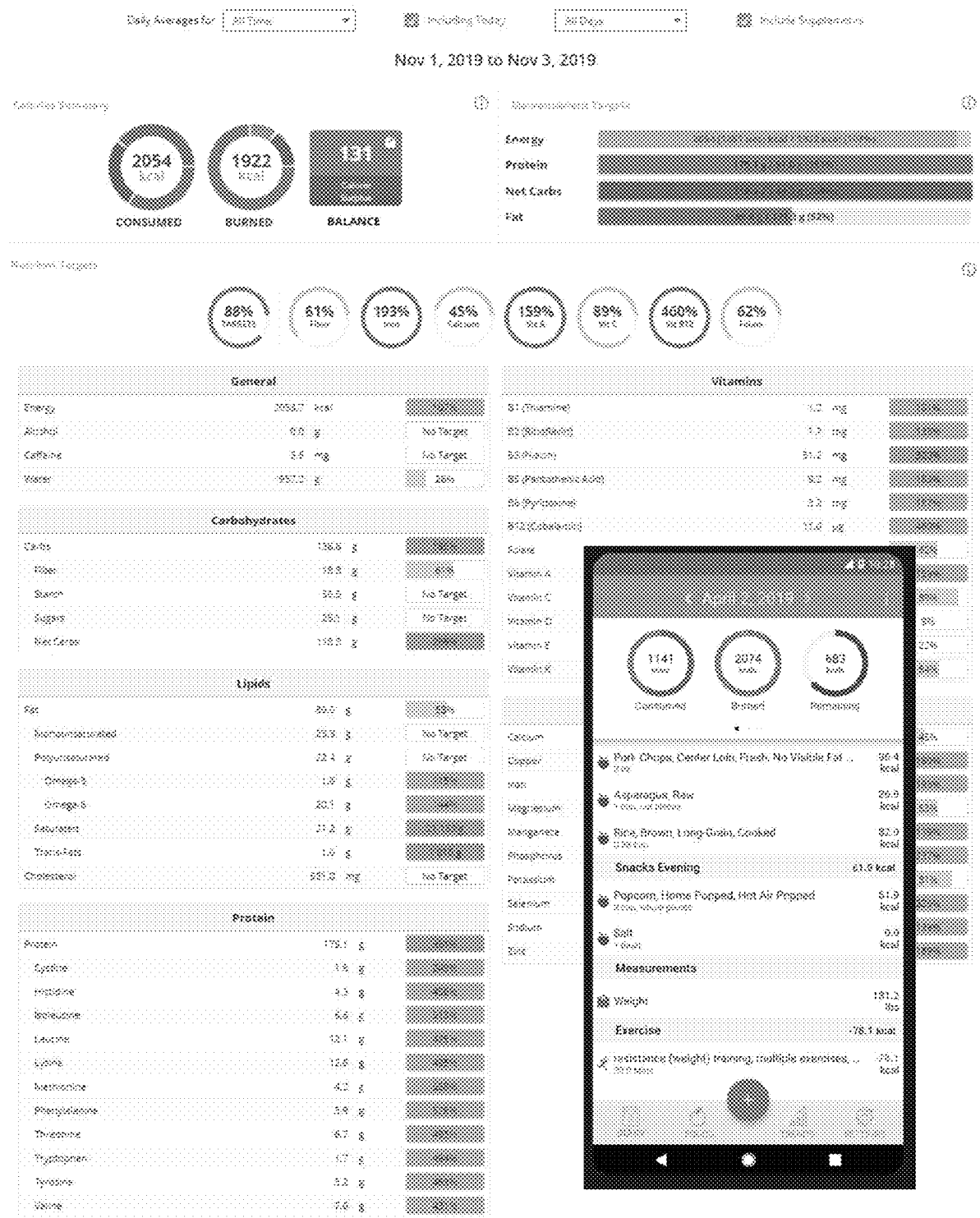
FIG. 17 shows an exemplary food logging system that records in depth the amount of food and the macronutrients consumed.

FIG. 14A shows an exemplary adhesive patch embodiment. The adhesive patch is shown generally at 190 having a gauze pad 194 attached to one side of a backing 192, preferably of plastic, and wherein the pad can have an impermeable side 194 coating with backing 192 and a module 196 which contains electronics for communicating with the mesh network and for sensing acceleration and bioimpedance, EKG/ECG, heart sound, microphone, optical sensor, or ultrasonic sensor in contacts with a wearer's skin.

FIG. 14B shows a sunglass or eyeglass embodiment which contains electronics for communicating with the mesh network and for sensing acceleration and bioimpedance, EKG/ECG, EMG, heart sound, microphone, optical sensor, or ultrasonic sensor in contacts with a wearer's skin. In one embodiment, the ear module 310 contains optical sensors to detect temperature, blood flow and blood oxygen level as well as a speaker to provide wireless communication or hearing aid. The blood flow or velocity information can be used to estimate blood pressure. The side module 312 can contain an array of bioimpedance sensors such as bipolar or tetrapolar bioimpedance probes to sense fluids in the brain. Additional bioimpedance electrodes can be positioned around the rim of the glasses as well as the glass handle or in any spots on the eyewear that contacts the user. The side module 312 or 314 can also contain one or more EKG electrodes to detect heart beat parameters and to detect heart problems. The side module 312 or 314 can also contain piezoelectric transducers or microphones to detect heart activities near the brain. The side module 312 or 314 can also contain ultrasound transmitter and receiver to create an ultrasound model of brain fluids.

As shown in FIG. 15A, a differential instrumentation amplifier is employed as an EMG sensor that works in concert with the glucose and cardiovascular sensors. In one embodiment, a housing (such as a strap, a wrist-band, or a patch) provides a plurality of sensor contacts for BioImpedance, EKG and/or EMG. The same contacts can be used for detecting BioImpedance, EKG or EMG and can be placed as two parallel contacts (linear or spot shape) on opposite sides of the band, two adjacent parallel contacts on the inner surface of the band, two parallel adjacent contacts on the back of the wrist-watch, or alternatively one contact on the back of the watch and one contact on the wrist-band. The outputs of the differential contacts are filtered to remove motion artifacts. The differential signal is captured, and suitably filtered using high pass/low pass filters to remove noise, and digitized for signal processing. In one embodiment, separate amplifiers are used to detect bioimpedance, EKG (between 50 mHz and 200 Hz) and for EMG (between 10 Hz and 500 Hz). In another embodiment, one common amp is used for EKG/EMG/bioimpedance sensing, and software filter is applied to the digitized signal to extract EKG and EMG signals, respectively. The unit can apply Wavelet processing to convert the signal into the frequency domain and apply neural network recognizers or Bayesian, NN or HMM to pull the bioimpedance, EMG or EKG signals from noise. Direct EMG pre-amplification at the skin surface provides the best myoelectric signal quality for accurate, reliable EMG signal detection and eliminates cable motion artifact. The double-differential instrumentation pre-amplifier design attenuates unwanted common-mode bioelectric signals to reduce cross-talk from adjacent muscle groups. The system can detect dominant symptoms of stroke can include weakness or paralysis of the arms and/or legs, incoordination (ataxia), numbness in the arms/legs using accelerometers or EMG sensors. The EMG sensors can detect muscle fatigue and can warn the patient to get to a resting area if necessary, to prevent a fall. The system can detect partial/total loss of vision by asking the patient to read a predetermined phrase and detect slur using speech recognizer. The system can detect loss of consciousness/coma by detecting lack of movement. Voice/speech disturbances are not initially the dominant symptoms in stroke, and the disturbances can be detected by a speech recognizer. In one implementation, the system uses PNL (probabilistic networks library) to detect unusual patient movement/ambulatory activities that will lead to a more extensive check for stroke attack or out of control glucose level occurrence. Neural network learning can be divided along many axes: parameter or structure, directed or undirected, fully observed or partially observed, batch or online, discriminative or maximum likelihood, among others. First, the system performs data normalization and filtering for the accelerometers and EMG sensors that detect patient movements and muscle strength. The data can include in-door positioning information, 3D acceleration information, or EMG/EKG/EEG data, for example. The data can be processed using wavelet as discussed above or using any suitable normalization/filtering techniques. Next, the system performs parameterization and discretization. The Bayesian network is adapted in accordance with a predefined network topology. The system also defines conditional probability distributions. The system then generates the probability of event P(y), under various scenarios. Training data is acquired and a training method is built for the Bayesian network engine. Next, the system tunes model parameters and performs testing on the thus formed Bayesian network.

FIGS. 15B and 15C shows exemplary sEMG outputs from a differential amplifier to detect muscle strength. FIG. 15B shows the left and right body EMG signals for the patient in a normal state, while FIG. 15C illustrates a patient with degraded muscle capability. The system can also determine muscle fatigue through the analysis of the frequency spectrum of the signal. The system can also assess neurological diseases which affect the fiber typing or the fiber cross-sectional area of the muscle. Various mathematical techniques and Artificial Intelligence (AI) analyzer can be applied. Mathematical models include wavelet transform, time-frequency approaches, Fourier transform, Wigner-Ville Distribution (WVD), statistical measures, and higher-order statistics. AI approaches towards signal recognition include Artificial Neural Networks (ANN), dynamic recurrent neural networks (DRNN), fuzzy logic system, Genetic Algorithm (GA), and Hidden Markov Model (HMM).

In addition to stroke detection, EMG can be used to sense isometric muscular activity (type of muscular activity that does not translate into movement). This feature makes it possible to define a class of subtle motionless gestures to control interface without being noticed and without disrupting the surrounding environment. Using EMG, the user can react to the cues in a subtle way, without disrupting their environment and without using their hands on the interface. The EMG controller does not occupy the user's hands, and does not require them to operate it; hence it is "hands free". The system can be used in interactive computer gaming which would have access to heart rate, galvanic skin response, and eye movement signals, so the game could respond to a player's emotional state or guess his or her level of situation awareness by monitoring eye movements. EMG/EEG signal can be used for man-machine interfaces by directly connecting a person to a computer via the human electrical nervous system. Based on EMG and EEG signals, the system applies pattern recognition system to interpret these signals as computer control commands. The system can also be used for Mime Speech Recognition which recognizes speech by observing the muscle associated with speech and is not based on voice signals but EMG. The MSR realizes unvoiced communication and because voice signals are not used, MSR can be applied in noisy environments; it can support people without vocal cords and aphasics. In another embodiment, EMG and/or electroencephalogram (EEG) features are used for predicting behavioral alertness levels. EMG and EEG features were derived from temporal, frequency spectral, and statistical analyses. Behavioral alertness levels were quantified by correct rates of performance on an auditory and a visual vigilance task, separately. A subset of three EEG features, the relative spectral amplitudes in the alpha (alpha %, 8-13 Hz) and theta (theta %, 4-8 Hz) bands, and the mean frequency of the EEG spectrum (MF) can be used for predicting the auditory alertness level.

In yet a further embodiment for performing motor motion analysis, an HMM is used to determine the physical activities of a patient, to monitor overall activity levels and assess compliance with a prescribed exercise regimen and/or efficacy of a treatment program. The HMM may also measure the quality of movement of the monitored activities. For example, the system may be calibrated or trained in the manner previously described, to recognize movements of a prescribed exercise program. Motor function information associated with the recognized movements may be sent to the server for subsequent review. A physician, clinician, or physical therapist with access to patient data may remotely monitor compliance with the prescribed program or a standardized test on motor skill. For example, patients can take the Wolf Motor Function test and acceleration data is captured on the following tasks: placing the forearm on a table from the side; moving the forearm from the table to a box on the table from the side; extending the elbow to the side; extending the elbow to the side against a light weight; placing the hand on a table from the front; moving the hand from table to box; flexing the elbow to retrieve a light weight; lifting a can of water; lifting a pencil, lifting a paper clip; stacking checkers, flipping cards; turning a key in a lock; folding a towel; lifting a basket from the table to a shelf above the table.

FIG. 16A shows an exemplary process to continuously determine blood pressure of a patient. The process generates a blood pressure model of a patient (2002); determines a blood flow velocity using a noninvasive sensor (2004); and provides the blood flow velocity to the blood pressure model to continuously estimate blood pressure (2006).

FIG. 16B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and the SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: Decimation method, and the wavelet method. Classification of the heart diseases is done using Hidden Markov Models (HMMs).

In yet another embodiment, a wavelet transform is applied to a window of two periods of heart sounds. In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur. In one embodiment, the time intervals between the ECG R-waves are detected using an envelope detection process. In yet another embodiment, the S2 is identified and a normalized splitting interval between A2 and P2 is determined. In another embodiment, the first heart sound (S1) is detected using a time-delayed neural network (TDNN). In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise. In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network. In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination, as detailed in Tran U.S. Pat. No. 9,820,658, the content of which is incorporated by reference.

In one implementation, an HMM is used to track patient motor skills or patient movement patterns. The muscular groups attached at various locations along the skeletal structure often have multiple functions. The majority of energy expended during walking is for vertical motion of the body. Wireless sensors with tri-axial accelerometers are mounted to the patient on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others. The sequence of human motions can be classified into several groups of similar postures and represented by mathematical models called model-states. In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the patient through additional tests to confirm a stroke attack, and if a stroke attack is suspected, the system prompts the user to seek medical attention immediately and preferably within the 3 hour for receiving TPA.

One exemplary process for determining weakness in the left or right half of the body. The process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others. The system can ask the patient to squeeze a strength gauge, piezoelectric sensor, or force sensor to determine force applied during squeeze. The system can detect hemiparesis, a very common symptom of stroke, by detecting muscular weakness or partial paralysis to one side of the body. Additionally, the accelerometers can detect ataxia, which is an impaired ability to perform smooth coordinated voluntary movements. Additionally, the system can detect aphasia, including receptive aphasia and expressive aphasia. Aphasia is a cognitive disorder marked by an impaired ability to comprehend (receptive aphasia) or express (expressive aphasia) language. Exemplary embodiments are disclosed for detecting receptive aphasia by displaying text or playing verbal instructions to the user, followed by measuring the correctness and/or time delay of the response from the user.

Depending on the severity of the stroke attack or out of control glucose level, patients can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. Patients with pure motor hemiparesis present with face, arm, and leg weakness. This condition usually affects the extremities equally, but in some cases it affects one extremity more than the other. The most common stroke location in affected patients is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. Patients with clumsy-hand dysarthria syndrome experience unilateral hand weakness and dysarthria. The dysarthria is often severe, whereas the hand involvement is more subtle, and patients may describe their hand movements as "awkward." This syndrome is usually caused by an infarct in the pons.

Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)-suggest hemispheric dysfunction with involvement of a superficial territory from an atherothrombotic or embolic occlusion of a mainstem vessel or peripheral branch.

The system can detect a pattern of motor weakness. Ischemia of the cortex supplied by the middle cerebral artery typically causes weakness that (1) is more prominent in the arm than in the leg and (2) involves the distal muscles more than the proximal muscles. Conversely, involvement of an area supplied by the superficial anterior cerebral artery results in weakness that (1) is more prominent in the leg than the arm and (2) involves proximal upper extremity (shoulder) muscles more than distal upper extremity muscles. Flaccid paralysis of both the arm and leg (unilateral) suggests ischemia of the descending motor tracts in the basal ganglia or brainstem. This is often caused by an occlusion of a penetrating artery as a result of small-vessel disease. Once the stroke is detected, intravenous (IV) tissue plasminogen activator (t-PA) needs to be given within 3 hours of symptom onset. An accurate assessment of the timing of the stroke is also crucial. The system keeps track of the timing off the onset of the stroke for this purpose.

One major symptom of a stroke is unexplained weakness or numbness in the muscle. To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the patient is at rest so that EMG data can be accurately captured or to compensate for motion artifacts in the EMG data in accordance with a linear or non-linear compensation table. In yet another embodiment, the EMG data is used to detect muscle fatigue and to generate a warning to the patient to get to a resting place or a notification to a nurse or caregiver to render timely assistance.

The amplitude of the EMG signal is stochastic (random) in nature and can be reasonably represented by a Gaussian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In the above embodiments, the base station can perform the bioelectric signal processing to extract patient parameters from data captured by the contacts. In this case, the base station may need a DSP or powerful CPU to perform the calculations. Alternatively, in an ASP model, the base station can simply compress the data and upload the data to a central server or server farm for processing and the result of the signal processing are sent back to the base station for relay to the patient interface which can be a wrist-watch, a pad, or a band, among others, for notification of any warning signs.

FIG. 19 shows a learning system architecture for determining glucose, heart rate, blood pressure, among others. The same architecture can also recommend treatment based on sensor data captured over time and based on treatment data for a population of users. For example, during examination, a doctor uses a smartphone to review sensor data from a biologic such as a human or an animal. Feature extraction is done on the data as detailed herein. In parallel, clinical information such as sex, age, temperature, medical history, among others, are provided to feature extraction. As the data is text, the feature extraction can be done by extracting feature windows around a particular word of interest. The description can be vectorized into a sparse two-dimensional matrix suitable for feeding into a classifier. Feature hashing, where instead of building a hash table of the features encountered in training, as the vectorizers do, instances of FeatureHasher apply a hash function to the features to determine their column index in sample matrices directly. Since the hash function might cause collisions between (unrelated) features, a signed hash function is used and the sign of the hash value determines the sign of the value stored in the output matrix for a feature. This way, collisions are likely to cancel out rather than accumulate error, and the expected mean of any output feature's value is zero.

In one embodiment, the neural network can apply data for monitoring a subject by coupling one or more noninvasive glucose sensors to the subject; calibrating the one or more noninvasive glucose sensors with a clinical grade data to track a subject glucose or insulin level during one or more subject physical activity condition; and in real time detecting a current subject physical activity level and applying the calibration to estimate a subject glucose or insulin level. Insulin is a peptic hormone which has an absorption spectrum in the mid-IR region that also corresponds to glucose. The absorption spectrum is found in the same region for both glucose and insulin (1100-900 cm-1). Even though they correspond to different vibrational modes, their absorption magnitude is on the same range. Thus, blood glucose quantification based in mid-IR spectroscopy such as wavelengths between 9 and 11 μm are useful for the proper measurement. In one embodiment, various combinations of bioimpedance, body heat, PPG, ECG, and absorption spectroscopy can be used to estimate glucose/insulin level at different physical activity. The subject physical activity condition includes sleep, exercise, walk, or run condition. The method includes collecting a plurality of vital signs from the subject; determining food intake effect on glucose or insulin level; determining physical activity effect on glucose or insulin level; applying a neural network to estimate a glucose level or insulin level from the subject; and advising the subject to perform a physical activity to control glucose or insulin level. An invasive monitor can be used to generate the clinical grade data. The neural network estimates against a continuous glucose monitoring (CGM) or a blood-based glucose meter output. The sensor can collect ECG, PPG, and body heat. Other data capturing includes collecting food intake or heat generated through metabolism. Various combinations of data to be captured can be used. For example, ECG, PPG, bioimpedance, and body heat can be done by themselves. ECG, bioimpedance, and body heat can be done. ECG, PPG, bioimpedance, and food intake can be done. ECG, PPG, bioimpedance, body heat, and absorption spectroscopy can be done. Other combinations include: ECG, PPG, body heat, and absorption spectroscopy; ECG, PPG, bioimpedance, food intake, and absorption spectroscopy; ECG, PPG, bioimpedance, bioimpedance, and absorption spectroscopy. Not all sensors are required for operation. For example, two or more of the following can be used by themselves: ECG, PPG, bioimpedance, bioimpedance, and absorption spectroscopy. Three or more of the following can be used by themselves: ECG, PPG, bioimpedance, bioimpedance, and absorption spectroscopy. The system can determine glycemic index (GI) from the subject glucose level.

One embodiment uses photoplethysmogram (PPG) to estimate glucose/insulin level. The insulin resistance in adipocytes caused by the increasing levels of free fatty acids in plasma can result in an exaltation of blood viscosity, which alters the blood flow in the capillaries, thus changing the shape of the PPG pulse. PPG from non-invasive sensor and from blood glucose meters are captured for training, and raw PPG data is filtered, sampled, and processed into a plurality of different variables for processing by a neural network. Data filtering is done to remove outliers and movement noise. Neural network is used for classification of "high" and "normal" glucose/insulin level. Another neural network predicts actual blood glucose levels based on personal and processed PPG data.

In addition, prior examination data can be featurized. At the time of a given exam, relevant information for predicting the diagnosis or prognosis may come not only from the current exam, but also from the results of past exams. The system combines information from the current and past exams when making a prediction of diagnosis or prognosis. If all users/patients received regular exams, for example, annually, it would be possible to simply generate one feature vector for the current exam, another for the exam from 1 year ago, another for the exam from 2 years ago, etc. Those feature vectors could then be combined via simple concatenation (possibly followed by dimensionality reduction) using the same procedure described herein to combine features within a single exam to form a combined feature vector. However, in general, patients may not be expected to all have had regular past exams on the same schedule. For example, patient A may have had annual exams, patient B may have had exams every other year, and patient C may have only had exams during periods of illness, which occurred at irregular intervals. Therefore, there is a need for a consistent method of converting information from past exams into a feature vector in a way that does not depend on the frequency or interval between past exams. One possible method for combining information from past exams is to combine features from past exams via a weighted average that takes into account the time from the current exam, with more recent exams weighted higher. For example, a linear weighting function could be used which linearly runs from 0 at birth to 1 at the present time. For an example patient of age 10 who had exams at ages 3 months, 9 months, and 6 years, each feature would be averaged together across exams (excluding the present exam), with weights of 0.025, 0.075 and 0.6. Weighting functions other than linear could be used (e.g., logarithmic, power law, etc.) and weights could also be normalized to add up to 1. Features from the current exam would also be included separately in the feature vector, concatenated together with the weighted features from past exams. Alternatively, one could include the current exam's features in the weighted feature vector from past exams, instead of including it separately. The generated feature vectors are then provided to a deep learning system.

One embodiment uses a conditional-GAN (cGAN) as a deep learning machine. The cGAN consists of two major parts: generator G and discriminator D. The task of generator is to produce an image indistinguishable from a real image and "fool" the discriminator. The task of the discriminator is to distinguish between real image and fake image from the generator, given the reference input image.

The objective of a conditional-GAN is composed of two parts: adversarial loss and LI loss. The adversarial loss can be: where L1 distance is added to generated image. L1 distance is preferred over L2 distance as it produces images with less blurring.

The ResNet-50 network by He et al. can be used as the generator, while the discriminator can be a convolutional "PatchGAN" classifier with architecture similar to the classifier in pix2pix as our discriminator.

In addition to cGAN, other neural networks can be used. Exemplary alternatives include 1. AlexNet—AlexNet is the first deep architecture which can be introduced by one of the pioneers in deep learning—Geoffrey Hinton and his colleagues. It is a simple yet powerful network architecture, which helped pave the way for groundbreaking research in Deep Learning as it is now.

2. VGG Net—The VGG Network can be introduced by the researchers at Visual Graphics Group at Oxford (hence the name VGG). This network is specially characterized by its pyramidal shape, where the bottom layers which are closer to the image are wide, whereas the top layers are deep. VGG contains subsequent convolutional layers followed by pooling layers. The pooling layers are responsible for making the layers narrower. In their paper, they proposed multiple such types of networks, with change in deepness of the architecture.

3. GoogleNet—In this architecture, along with going deeper (it contains 22 layers in comparison to VGG which had 19 layers), the Inception module is used. In a single layer, multiple types of "feature extractors" are present. This indirectly helps the network perform better, as the network at training itself has many options to choose from when solving the task. It can either choose to convolve the input, or to pool it directly. The final architecture contains multiple of these inception modules stacked one over the other. Even the training is slightly different in GoogleNet, as most of the topmost layers have their own output layer. This nuance helps the model converge faster, as there is a joint training as well as parallel training for the layers itself.

4. ResNet—ResNet is one of the monster architectures which truly define how deep a deep learning architecture can be. Residual Networks (ResNet in short) consists of multiple subsequent residual modules, which are the basic building block of ResNet architecture. ResNet uses of standard SGD instead of a fancy adaptive learning technique. This is done along with a reasonable initialization function which keeps the training intact; Changes in preprocessing the input, where the input is first divided into patches and then feeded into the network. The main advantage of ResNet is that hundreds, even thousands of these residual layers can be used to create a network and then trained. This is a bit different from usual sequential networks, where you see that there is reduced performance upgrades as you increase the number of layers.

5. ResNeXt—ResNeXt is said to be the current state-of-the-art technique for object recognition. It builds upon the concepts of inception and resnet to bring about a new and improved architecture.

6. RCNN (Region Based CNN)—Region Based CNN architecture is said to be the most influential of all the deep learning architectures that have been applied to object detection problem. To solve detection problem, what RCNN does is to attempt to draw a bounding box over all the objects present in the image, and then recognize what object is in the image.

7. YOLO (You Only Look Once)—YOLO is a real time system built on deep learning for solving image detection problems. As seen in the below given image, it first divides the image into defined bounding boxes, and then runs a recognition algorithm in parallel for all of these boxes to identify which object class do they belong to. After identifying this classes, it goes on to merging these boxes intelligently to form an optimal bounding box around the objects. All of this is done in parallely, so it can run in real time; processing upto 40 images in a second.

8. SqueezeNet—The squeezeNet architecture is one more powerful architecture which is extremely useful in low bandwidth scenarios like mobile platforms. This architecture has occupies only 4.9 MB of space, on the other hand, inception occupies ~100 MB! This drastic change is brought up by a specialized structure called the fire module which is good for mobile phone.

9. SegNet—SegNet is a deep learning architecture applied to solve image segmentation problem. It consists of sequence of processing layers (encoders) followed by a corresponding set of decoders for a pixelwise classification. Below image summarizes the working of SegNet. One key feature of SegNet is that it retains high frequency details in segmented image as the pooling indices of encoder network is connected to pooling indices of decoder networks. In short, the information transfer is direct instead of convolving them. SegNet is one the best model to use when dealing with image segmentation problems.

With accelerometers and gyroscopes, the system can analyze user locomotion, which requires the measurement and analysis of the following: Temporal characteristics, Electromyographic signals, Kinematics of limb segments, and Kinetics of the foot-floor and joint resultants. Temporal analysis of gait in the person provides some norms for the average velocity of walking as well as time durations for the two phases of gait: the stance phase and the swing phase. The symmetry and asymmetry of gait can be captured by the accelerometer.

The system can model the kinematics or relative motion that exists between rigid bodies, known as links between the body and the legs. Kinematic analysis of gait involves accelerometers positioned at different body parts to capture the displacement, velocity, and acceleration of various body segments. A model of the links and their movements can be created for diagnosis and also for real time assistance if needed. The model can also be used for energy consumption analysis, athletic training, and predictive health for particular tasks.

In one embodiment, the gaits of the user are commonly used patterns of locomotion that can be divided into two main groups: symmetric and asymmetric. With symmetric gaits such as the walk, trot, and pace, the movement of the limbs on one side of the user body repeats the motion of the limbs on the opposite side with the intervals between foot falls being nearly evenly spaced. With asymmetric gaits such as the competitive running for person or gallop for a horse, the limb movements of one side do not repeat those of the other and the intervals between foot falls are unevenly spaced. When considering gaits, one full cycle is referred to as a stride. The system can detect neurologic problems, as almost every neurologic condition will be associated in some way with an abnormality of gait, such as an inability to gait, knuckling, lameness, unsteadiness, or development of a protective mode of walking evidencing severe pain.

There is no intention to limit the system to the specific form or forms disclosed herein, but on the contrary, the intention is to cover all modifications, alternative constructions, and equivalents falling within the spirit and scope of the above system.

What is claimed is:

1. A method for monitoring a subject, comprising:
placing a watch with one or more noninvasive glucose sensors coupled to the subject and directing light on the subject and sensing light reflected from the subject with the one or more noninvasive glucose sensors;
calibrating the one or more noninvasive glucose sensors with a clinical grade data to track a subject glucose or insulin level during one or more subject physical activity conditions; and
in real time, detecting a current subject physical activity level and applying the calibration to the output of the one or more glucose sensors worn on the subject to estimate a subject glucose or insulin level.

2. The method of claim 1, wherein the one or more subject physical activity conditions includes sleep, exercise, walk, or run condition.

3. The method of claim 1, comprising:
collecting a plurality of vital signs from the subject;
determining food intake effect on glucose or insulin level;
determining physical activity effect on glucose or insulin level;

applying a neural network to estimate a glucose level or insulin level from the subject; and advising the subject to perform a physical activity to control glucose or insulin level.

4. The method of claim 1, comprising using an invasive monitor to generate the clinical grade data.

5. The method of claim 1, comprising applying a neural network estimate against a continuous glucose monitoring (CGM) or a blood-based glucose meter output.

6. The method of claim 1, comprising collecting ECG, PPG, and body heat for calibrating the glucose sensors.

7. The method of claim 1, comprising collecting food intake or heat generated through metabolism for calibrating the glucose sensors.

8. The method of claim 1, comprising collecting ECG, PPG, bioimpedance, and body heat for calibrating the glucose sensors.

9. The method of claim 1, comprising collecting ECG, bioimpedance, and body heat for calibrating the glucose sensors.

10. The method of claim 1, comprising collecting ECG, PPG, bioimpedance, and food intake for calibrating the glucose sensors.

11. The method of claim 1, comprising collecting ECG, PPG, bioimpedance, body heat, and absorption spectroscopy for calibrating the glucose sensors.

12. The method of claim 1, comprising collecting ECG, PPG, body heat, and absorption spectroscopy for calibrating the glucose sensors.

13. The method of claim 1, comprising collecting ECG, PPG, bioimpedance, food intake, and absorption spectroscopy for calibrating the glucose sensors.

14. The method of claim 1, comprising collecting ECG, PPG, bioimpedance, bioimpedance, and absorption spectroscopy for calibrating the glucose sensors.

15. The method of claim 1, comprising collecting two or more of: ECG, PPG, bioimpedance, bioimpedance, and absorption spectroscopy for calibrating the glucose sensors.

16. The method of claim 1, comprising determining glycemic index (GI) from the subject glucose level.

17. The method of claim 16, comprising determining carbohydrate content of consumed food with one or more given food items, and determining a proportion of carbohydrate content in a given food item in a consumed nutritional load, and summing the GI of each food item based on the proportion, and determining a total nutritional load GI.

18. The method of claim 16, comprising recording food intake or taking a picture of food and then determining constituent food ingredients, and correlating the food intake to the GI.

19. The method of claim 1, comprising detecting heart rate or electrocardiogram (ECG) to use with the noninvasive glucose sensor output to improve glucose determination.

20. The method of claim 19, comprising calibrating at least an ECG sensor to medical grade ECG data; and using the sensor's ECG data to track glucose or insulin level.

21. The method of claim 1, comprising:
directing a plurality of LEDs at different wavelengths toward subject skin and detecting the light with one or more photodiode detectors;
clinically capturing one or more blood constituents including blood urea nitrogen (BUN), high-density lipoprotein (HDL), low-density lipoprotein (LDL), total hemoglobin (TUB), creatine (CRE);
deriving composite parameters from the photodiode detector and providing the blood constituent data and the composite parameters to a neural network or statistical analyzer during training; and
during operation, applying the neural network or statistical analyzer to the photodetector to determine a particular blood constituent.

22. A method for monitoring a subject, comprising:
using a glucose monitor with a probe in the subject to generate clinical grade data;
coupling noninvasive glucose sensors including an optical sensor and an electrical sensor in a watch to the subject;
using the optical sensor, directing a plurality of LEDs at different wavelengths toward subject skin and detecting the light with one or more photodiode detectors;
calibrating the noninvasive glucose sensors and the electrical sensor with the clinical grade data to track a subject glucose level during one or more subject conditions;
generating a calibration curve based on the one or more subject conditions; and
in real time detecting a current subject condition and applying the calibration curve to accurately estimate the subject glucose level.

* * * * *